(12) United States Patent
Reisman et al.

(10) Patent No.: US 11,926,589 B2
(45) Date of Patent: Mar. 12, 2024

(54) PROCESS FOR THE SYNTHESIS OF NON-RACEMIC CYCLOHEXENES

(71) Applicants: BASF CORPORATION, Florham Park, NJ (US); California Institute of Technology, Pasadena, CA (US)

(72) Inventors: Sarah Reisman, Pasadena, CA (US); Michael Rombola, Pasadena, CA (US); Carolyn L. Ladd, Pasadena, CA (US); Martin John McLaughlin, Ludwigshafen (DE); Stephan Zuend, Hayward, CA (US); Roland Goetz, Ludwigshafen (DE)

(73) Assignees: BASF CORPORATION, Florham Park, NJ (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 93 days.

(21) Appl. No.: 17/625,414

(22) PCT Filed: Jul. 6, 2020

(86) PCT No.: PCT/US2020/040856
§ 371 (c)(1),
(2) Date: Jan. 7, 2022

(87) PCT Pub. No.: WO2021/007141
PCT Pub. Date: Jan. 14, 2021

(65) Prior Publication Data
US 2022/0267247 A1 Aug. 25, 2022

Related U.S. Application Data

(60) Provisional application No. 62/871,838, filed on Jul. 9, 2019.

(30) Foreign Application Priority Data

Sep. 6, 2019 (EP) .................................. 19195787

(51) Int. Cl.
*C07C 67/293* (2006.01)
*C07B 53/00* (2006.01)

(52) U.S. Cl.
CPC ............ *C07C 67/293* (2013.01); *C07B 53/00* (2013.01); *C07B 2200/07* (2013.01)

(58) Field of Classification Search
CPC ..... C07C 67/293; C07C 205/57; C07B 53/00; C07B 2200/07; C07D 401/14
See application file for complete search history.

(56) References Cited

U.S. PATENT DOCUMENTS 6,211,370 B1 * 4/2001 Jacobsen ................ C07B 37/02
546/25

OTHER PUBLICATIONS

Bhor, S., et al., Synthesis of a new chiral N,N,N-tridentate pyridinebisimidazoline ligand library and its application in Ru-catalyzed asymmetric epoxidation, Organic Letters, Vo, 7, No. 16, pp. 3393-3396 (Year: 2005).*
Anguilar, R., et al., Regioselectivity of Diels-Alder additions of 1-acetylvinyl arenecarboxylates, Tetrahedron Lett., vol. 28, No. 8, pp. 865-868 (Year: 1987).*
Ochoa, M., et al., Captodative Olefin 3-p-nitrobenzoyloxy-3-buten-2-one as a Diels-Alder Ketene equivalent for the synthesis of gamma-hydroxycyclohexenones, Tetrahedron, vol. 55, No. 51, pp. 14535-14546 (Year: 1999).*
Reyes, A.., et al., Highly selective Diels-Alder cycloadditions of captodative dienophiles 1-acetylvinyl arenecarboxylates to unsymmetrically substituted butadienes, J. Org. Chem., vol. 55, pp. 1024-1034 (Year: 1990).*
Aguilar et al., Regioselectivity of Diels-Alder additions of 1-acetylvinyl arenecarboxylates, Tetrahedron Lett., 28(8):865-8 (1987).
International Application No. PCT/US2020/040856, International Preliminary Report on Patentability, dated Jun. 18, 2021.
International Application No. PCT/US2020/040856, International Search Report and Written Opinion, dated Oct. 5, 2020.
Ochoa et al., Captodative Olefin 3-p-Nitrobenzoyloxy-3-buten-2-one as a Diels-Alder Ketene Equivalent for the Synthesis of gamma-Hydroxycyclohexenones, Tetrahedron, 55(51):14535-46 (1999).
Reyes et al., Highly selective diels-alder cycloadditions of captodative dienophiles 1-acetylvinyl arenecarboxylates to unsymmetrically substituted butadienes, J. Org. Chem., 55:1024-34 (1990).

* cited by examiner

*Primary Examiner* — Yate' K Cutliff
(74) *Attorney, Agent, or Firm* — MARSHALL, GERSTEIN & BORUN LLP

(57) ABSTRACT

This invention relates to a process for the synthesis of a non-racemic cyclohexene compound of formula (I) by a Diels-Alder reaction of a compound of formula (II) with a compound of formula (III) wherein $R^1$, $R^2$, $R^3$, $R^4$, $R^5$, $R^6$, $R^7$, $R^8$, $R^9$ and Y have the meanings as defined in the description in the presence of a catalyst comprising at least one m-valent metal cation $M^{m+}$ wherein the metal M is selected from Scandium (Sc), Yttrium (Y), Lanthanum (La), Cerium (Ce), Praseodymium (Pr), Neodymium (Nd), Promethium (Pm), Samarium (Sm), Europium (Eu), Gadolinium 15 (Gd), Terbium (Tb), Dysprosium (Dy), Holmium (Ho), Erbium (Er), Thulium (Tm), Ytterbium (Yb), Lutetium (Lu), Gallium (Ga) and Indium (In), and m is an integer of 1, 2 or 3, and a chiral ligand of the formula (IV) wherein $R^{10a}$, $R^{10b}$, $R^{10c}$, $R^{10d}$, $R^{10a'}$, $R^{10b'}$, $R^{10c'}$, $R^{10d'}$, Z and Z' have the meanings as defined in the description.

33 Claims, No Drawings

PROCESS FOR THE SYNTHESIS OF NON-RACEMIC CYCLOHEXENES

CROSS-REFERENCE TO RELATED APPLICATIONS

This is the U.S. national phase of International Application No. PCT/US2020/040856, filed Jul. 6, 2020, which claims the benefit of U.S. patent application Ser. No. 62/871,838, filed Jul. 9, 2019, and which claims priority to European Patent Application No. 19195787.7, filed Sep. 6, 2019.

This invention relates to a process for the synthesis of a non-racemic cyclohexene compound of formula (I) by a Diels-Alder reaction of a compound of formula (II) (herein also referred to as the "dienophile") with a compound of formula (III) (herein also referred to as the "diene")

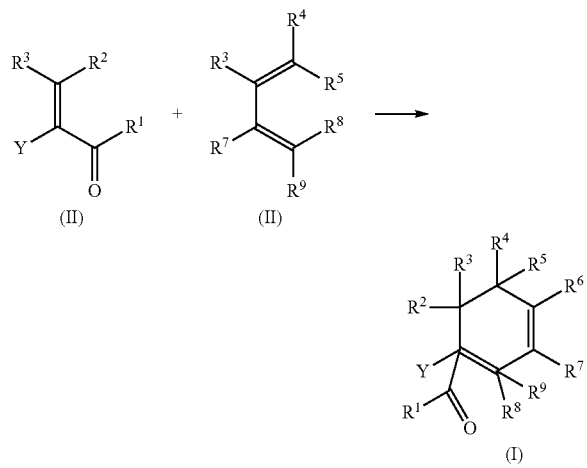

wherein $R^1$, $R^2$, $R^3$, $R^4$, $R^5$, $R^6$, $R^7$, $R^8$, $R^9$ and Y have the meanings indicated below in the presence of a chiral catalyst.

BACKGROUND OF THE INVENTION

Chiral cyclohexene derivatives of formula (I) in which Y is O—X (X=e.g., acyl) and $R^1$ is alkyl, cycloalkyl, aryl, or hetaryl are useful intermediates for the chemical synthesis of cyclohexenols such as, for example, limonene-4-ol (herein also referred to as "1-Isopropenyl-4-methyl-cyclohex-3-en-1-ol" or "p-mentha-1,8-diene-4-ol"). Limonene-4-ol and related cyclohexenols are in turn used as intermediates in the chemical synthesis of terpene compounds. In some contexts, access to non-racemic compounds of formula (I) is desirable, as these would give access to non-racemic cyclohexenols (e.g. limonene-4-ol).

Reyes et al. (Journal of Organic Chemistry, 1990, 55, 1024-1034) describes regioselective Diels-Alder cycloadditions of captodative olefins 1-acetylvinyl arenecarboxylates, $CH_2=C(COCH_3)OCOAr$ with $Ar=C_6H_4pNO_2$, α-naphthyl, and β-naphthyl (dienophiles 1a-c) with isoprene (diene 2) by using achiral Lewis acids catalysis ($ZnCl_2$, $BF_3.Et_2O$), with the para adduct being the main isomer. In order to determine the ratio of the resulting mixtures of adducts, it was necessary to convert them to the corresponding alcohols by ester cleavage of the mixtures and calculating the proportions of the corresponding alcohols by gas chromatography (GLC). The cycloaddition of dienophile 1a to 1-substituted dienes, i.e. 1-acetoxybutadiene (3), 1-methoxybutadiene (4), and 1-(methoxycarbonyl)-1,3-butadiene (6), and the 1,3-disubstituted butadiene 1-methoxy-3-[(trimethylsilyl)oxy]butadiene) (5) was reported to be highly regioselective too, with the ortho isomer being the only observed adduct. Further, Reyes et al. describes that, for all of these dienes including 1,4-diacetoxybutadiene (7), the endo stereoisomer was obtained in a high proportion (>80%).

Andrade et al. (Synthetic Communications, 1992, 22, 1603-1609) describes the synthesis of racemic limonene-4-ol (also referred to as "p-mentha-1,8-diene-4-ol (1)") by using 1-Acetyl-4-methyl-3-cyclohexen-1-ol (7) as a precursor. First, the achiral Lewis acid catalyzed cycloaddition of 3-p-Nitrobenzoyloxy-3-buten-2-one (8) with isoprene (9) gives the para adduct (10) with a high regioselectivity. 1-Acetyl-4-methyl-3-cyclohexen-1-ol (7) was prepared by cleavage of the ester of the para adduct (10) using $K_2CO_3$ and methanol, and then subjected to a Wittig reaction with a reagent generated from methyltriphenylphosphonium bromide and n-butyllithium to give limonene-4-ol (1).

Ochoa et al. (Tetrahedron 55 (1999) 14535-14546) describes a regioselective synthesis of γ-hydroxycyclohexenones, using 3-p-nitrobenzoyloxy-3-buten-2-one as a ketene equivalent in Diels-Alder reactions with substituted dienes.

Aguilar et al. (Tetrahedron Letters, Vol. 28, No. 8, pp 865-868, 1987) describes that the DielsAlder-addition of "captodative" dienophiles 1-acetylvinyl arenecarboxylates to 1- and 2-substituted dienes was found highly regioselective by using Lewis acid catalysis.

However, the methods described in Reyes et al., Andrade et al., Ochoa et al. and Aguilar et al. neither allow access to non-racemic compounds of formula (I) nor do they enable efficient synthesis of non-racemic cyclohexenols, such as in particular limonene-4-ol.

Rickerby et al. (Chemistry A European Journal, 2007, 13, 3354-3368) describes asymmetric Diels-Alder reactions between certain dienes (cyclopentadiene, methylcyclopentadiene, isoprene, 2,3-dimethylbutadiene) and certain α,β-unsaturated ketones (methyl vinyl ketone, ethyl vinyl ketone, divinyl ketone, α-bromovinyl methyl ketone and α-chlorovinyl methyl ketone) by using the complex [Ru(cyclopentadiene)(R,R-BIPHOP-F)(acetone)][$SbF_6$] as catalyst. The cycloaddition products were obtained in yields of 50-90% and with enantioselectivities up to 96% ee (enantiomeric excess).

Evans et al. (Journal of the American Chemical Society, 1999, 121, 7582-7594) describes that the Diels-Alder reaction between 3-propenoyl-2-oxazolidinone (2) and a range of substituted dienes catalyzed by bis(oxazoline)copper complexes, in particular [Cu((S,S)-tert-butyl-box)]($SbF_6$)$_2$ or [Cu((S,S)-tert-butyl-box)](OTf)$_2$ results in cycloaddition products in 60-95% yield and 60-97% ee.

However, neither Rickerby et al. nor Evans et al. is concerned with the synthesis of non-racemic formula I compounds in which Y is O—X (with X=e.g., acyl). Further, the conversion of the reported non-racemic formula I compounds in which Y is H or halogen to Y=O—X (with X=e.g., acyl) or Y =O—H is not expected to be readily achievable. Thus, neither do these methods enable the synthesis of non-racemic cyclohexenols.

Ishihara and Nakano (Journal of the American Chemical Society, 2005, 127, 10504-10505) describes the enantioselective Diels-Alder reaction of cyclic and acyclic dienes, such as cyclopentadiene, cyclohexadiene, 5-(benzyloxymethyl)cyclopentadiene (BMCP), 2,3-dimethylbutadiene and isoprene with α-substituted acroleins by using a chiral amine catalyst. However, this method is only applied to the synthesis of formula (I) compounds in which $R_1$ is H, that is, where the dienophile contains an aldehyde functionality. Enantioenriched formula (I) compounds in which $R_1$ is H can only be converted to enantioenriched formula (I) compounds in which $R_1$ is different from H, such as e.g. alkyl, cycloalkyl, aryl, or hetaryl, via a laborious multistep procedure, involving for example Grignard addition followed by oxidation. Thus, this method does not enable a practical, general synthesis of non-racemic cyclohexenols, such as in particular limonene-4-ol.

OBJECT OF THE INVENTION

One object of the present invention is to provide an efficient process for the synthesis of non-racemic cyclohexene compounds of formula (I) in which Y is O—X (with X=e.g., acyl) and $R_1$ is alkyl, cycloalkyl, aryl, or hetaryl, that can be readily converted to non-racemic cyclohexenols such as in particular limonene-4-ol, starting from the corresponding compounds of formulae (II) and (III).

Another object of the present invention is to provide a process for the synthesis of non-racemic cyclohexene compounds of formula (I) in which Y is O—X (with X=e.g., acyl) and $R_1$ is alkyl, cycloalkyl, aryl, or hetaryl, starting from the corresponding compounds of formulae (II) and (III), which is safe, simple, economical and commercially viable.

Yet another object of this invention is to provide a process for the synthesis of non-racemic cyclohexene compounds of formula (I) in which Y is O—X (with X=e.g., acyl) and $R_1$ is alkyl, cycloalkyl, aryl, or hetaryl, starting from the corresponding compounds of formulae (II) and (III), with a high enantiomeric excess without compromising yield.

Yet another object of this invention is to provide a process for the synthesis of non-racemic cyclohexene compounds of formula (I) in which Y is O—X (with X=e.g., acyl) and $R_1$ is alkyl, cycloalkyl, aryl, or hetaryl, starting from the corresponding compounds of formulae (II) and (III), with an enantiomeric excess of at least 75%, preferably at least 80% and more preferably at least 85%.

SUMMARY OF THE INVENTION

These objects are in part or in whole achieved by a process for the synthesis of a non-racemic cyclohexene compound of formula (I)

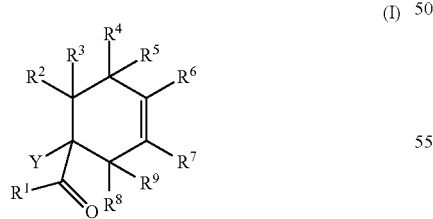

wherein
$R^1$ is selected from $C_1$-$C_8$-alkyl, $C_3$-$C_{12}$-cycloalkyl, unsubstituted or substituted $C_6$-$C_{20}$-aryl and unsubstituted or substituted $C_3$-$C_{20}$-heteroaryl,
$R^2$, $R^3$, $R^4$, $R^5$, $R^6$, $R^7$, $R^8$ and $R^9$ are each independently selected from hydrogen, $C_1$-$C_8$-alkyl, $C_3$-$C_6$-cycloalkyl, unsubstituted or substituted $C_6$-$C_{20}$-aryl and unsubstituted or substituted $C_3$-$C_{20}$-heteroaryl, or $R^5$ and $R^8$ together form a bridging moiety selected from —O—, —CH$_2$—, and —CH$_2$—CH$_2$— between the carbon atoms to which they are connected;
Y is OC(O)$R_A$ wherein $R_A$ is selected from $C_1$-$C_8$-alkyl, $C_3$-$C_{12}$-cycloalkyl, unsubstituted or substituted $C_6$-$C_{20}$-aryl, $C_6$-$C_{20}$-aryl-$C_1$-$C_4$-alkyl, di($C_6$-$C_{20}$-aryl)-$C_1$-$C_4$-alkyl, unsubstituted or substituted $C_3$-$C_{20}$-heteroaryl, $C_1$-$C_8$-alkoxy, $C_3$-$C_6$-cycloalkyloxy, $C_6$-$C_{20}$-aryloxy, and $NR_B R_{B'}$, where $R_B$ and $R_{B'}$ are independently selected from hydrogen, $C_1$-$C_8$-alkyl, and $C_3$-$C_{12}$-cycloalkyl; which process comprises reacting a compound of formula (II)

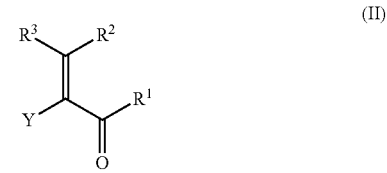

wherein $R^1$, $R^2$, $R^3$ and Y have the same meaning as in formula (I) with a compound of formula III,

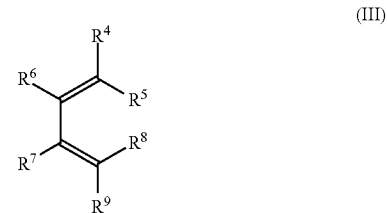

wherein $R^4$, $R^5$, $R^6$, $R^7$, $R^8$ and $R^9$ have the same meaning as in formula (I);
in the presence of a catalyst comprising at least one m-valent metal cation $M^{m+}$ wherein the metal M is selected from Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Gallium (Ga) and Indium (In), and m is an integer of 1, 2 or 3, and a chiral ligand of the formula (IV)

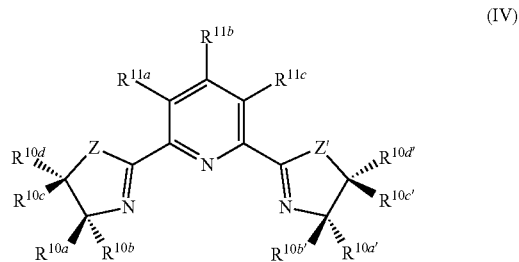

wherein $R^{10a}$, $R^{10b}$, $R^{10c}$, $R^{10d}$, $R^{10a'}$, $R^{10b'}$, $R^{10c'}$ and $R^{10d'}$ are each independently selected from hydrogen, $C_1$-$C_8$-alkyl, $C_3$-$C_6$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$-heteroaryl, or two or more of $R^{10a}$, $R^{10b}$, $R^{10c}$ and $R^{10d}$ and/or two or more of $R^{10a'}$, $R^{10b'}$, $R^{10c'}$ and $R^{10d'}$ together form an unsubstituted or substituted ring selected from $C_3$-$C_6$-cycloalkyl, $C_6$-$C_{20}$-aryl and $C_3$-$C_{20}$-heteroaryl;

provided that at least one of $R^{10a}$, $R^{10b}$, $R^{10c}$ and $R^{10d}$ and at least one of $R^{10a'}$, $R^{10b'}$, $R^{10c'}$ and $R^{10d'}$ are not hydrogen;

$R^{11a}$, $R^{11b}$ and $R^{11c}$ are each independently selected from hydrogen, halogen, cyano, $C_1$-$C_8$-alkyl, $C_1$-$C_4$-haloalkyl, $C_3$-$C_6$-cycloalkyl, unsubstituted or substituted $C_6$-$C_{20}$-aryl, unsubstituted or substituted $C_3$-$C_{20}$-heteroaryl, $C_1$-$C_8$-alkoxy, $C_3$-$C_6$-cycloalkyloxy, $C_6$-$C_{20}$-aryloxy, C(O)—O—$C_1$-$C_6$-alkyl and O—C(O)—$C_1$-$C_6$-alkyl, and Z and Z' are the same or different and selected from —O—, —O—CH$_2$—, or

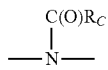

wherein $R_C$ is selected from $C_1$-$C_8$-alkyl, $C_3$-$C_3$-cycloalkyl, $C_1$-$C_8$-haloalkyl, and unsubstituted or substituted $C_6$-$C_{13}$ aryl.

It has surprisingly been found that the desired non-racemic cyclohexene compounds of formula (I) can be advantageously prepared by a Diels-Alder cycloaddition between the corresponding dienophile (II) and diene (III) in the presence of a specific chiral catalyst. The inventive process also has the advantage that the desired non-racemic cyclohexene compounds of formula (I) can be obtained with a high enantiomeric excess without compromising yield. The cycloaddition reaction involves the use of safe and cheap starting materials and low reaction temperatures which makes the process of this invention commercially viable. Further, the non-racemic cyclohexene compounds (I) prepared by the process of this invention can be readily converted to non-racemic cyclohexenols such as in particular limonene-4-ol.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

Non-racemic cyclohexene compounds of formula (I) are also called enantiomerically enriched compounds of the formula (I). For the purpose of this invention, the terms are equivalent, and mean that the ratio of the two enantiomers is at least 1.5:1, preferably 3:1, more preferably 4:1, especially preferably 10:1, and most preferably at least 20:1.

Preferably, the non-racemic cyclohexene compound of the formula (I) is the S-isomer, for example the S-isomer with an enantiomeric excess (ee) of preferably at least 75%, more preferably of at least 80%, even more preferably of at least 85%, yet more preferably of at least 90% and in particular of at least 95%, for example at least 97%.

In another preferred embodiment, the non-racemic cyclohexene compound of the formula (I) is the R-isomer, for example the R-isomer with an enantiomeric excess (ee) of preferably at least 75%, more preferably of at least 80%, even more preferably of at least 85%, yet more preferably of at least 90% and in particular of at least 95%, for example at least 97%.

The abbreviation "ee" is used herein to describe the enantiomeric excess. The term "enantiomeric excess" is used herein to describe the relative amount of an enantiomer in the non-racemic mixture of the cyclohexene compound of formula (I). The enantiomeric excess (ee) of the non-racemic cyclohexene compounds of formula (I) can be determined by means of common methods, for example by determining the optical rotation or by chromatography on a chiral phase, such as e.g. by supercritical fluid chromatography (SFC), high performance liquid chromatography (HPLC) or gas chromatography (GC) using chiral columns.

The term "halogen" as used herein in each case denotes fluorine, chlorine, bromine or iodine, preferably fluorine or chlorine.

The term "halide" as used herein in each case denotes a fluoride ion, a chloride ion, a bromide ion or an iodide ion, preferably a fluoride ion or chloride ion.

The organic moieties mentioned in the definition of the substituents as used herein, i.e. $R^1$, $R^2$, $R^3$, $R^4$, $R^5$, $R^6$, $R^7$, $R^8$, $R^9$, $R^{10a}$, $R^{10b}$, $R^{10c}$, $R^{10d}$, $R^{10a'}$, $R^{10b'}$, $R^{10c'}$, $R^{10d'}$, $R^{11a}$, $R^{11b}$, $R^{11c}$, $R^{12}$, $R^{13}$, $R^{14}$, $R_A$, $R_B$, $R_{B'}$, $R_C$, $R_D$, $R_{D'}$, $R_E$ and $R_{E'}$ are—like the terms halogen or halide—collective terms for individual enumerations of the individual group members. All hydrocarbon chains, i.e. all alkyl, can be straight-chain or branched, the prefix $C_n$-$C_m$ denoting in each case the possible number of carbon atoms in the group.

The term "alkyl" as used herein refers to a branched or unbranched saturated hydrocarbon group, for example, $C_1$-$C_4$-alkyl (including the $C_1$-$C_4$-alkyl moieties of $C_6$-$C_{20}$-aryl-$C_1$-$C_4$-alkyl and di($C_6$-$C_{20}$-aryl)-$C_1$-$C_4$-alkyl) or $C_1$-$C_6$-alkyl (including the $C_1$-$C_6$-alkyl moieties of C(O)—O-C1-$C_6$-alkyl and O—C(O)—$C_1$-$C_6$-alkyl), such as methyl, ethyl, n-propyl, iso-propyl (—CH(CH$_3$)$_2$), n-butyl, sec-butyl (—CH(CH$_3$)—C$_2$H$_5$), isobutyl (—CH$_2$—CH (CH$_3$)$_2$), tert-butyl (—C(CH$_3$)$_3$), n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or 2-ethylhexyl.

The term "cycloalkyl" as used herein refers to a monocyclic or polycyclic saturated hydrocarbon group, for example $C_3$-$C_6$-cycloalkyl (including the $C_3$-$C_6$-cycloalkyl moiety of $C_3$-$C_6$-cycloalkyloxy), $C_3$-$C_3$-cycloalkyl or $C_3$-$C_{12}$-cycloalkyl. Monocylic cycloalkyl groups include cyclopropyl, cyclobutyl, cyclopentyl, cyclohexyl, cycloheptyl, cyclooctyl, cyclononyl, cyclodecyl, cycloundecyl and cyclododecyl. Polycyclic cycloalkyl groups may be fused or spiro cycloalkyl groups. Examples of polycyclic cycloalkyl include adamantyl (including both 1-adamantyl and 2-adamantyl), norbornyl (including 1-norbornyl, 2-norbornyl and 7-norbornyl) and decalinyl (including 1-decalinyl, 2-decalinyl and 3-decalinyl).

The term "haloalkyl" as used herein refers to a straight-chain or branched alkyl groups, where some or all of the hydrogen atoms in these groups may be replaced by halogen atoms as mentioned above, for example $C_1$-$C_4$-haloalkyl or $C_1$-$C_8$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

The term "alkoxy" as used herein refers to straight-chain or branched alkyl groups bonded through oxygen linkages at any bond in the alkyl group such as $C_1$-$C_8$-alkoxy. Examples include methoxy, ethoxy, propoxy, isopropoxy, butoxy or isobutoxy.

The term "aryl" as used herein refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl), each of which may be unsubstituted or substituted, for example unsubstituted or substituted $C_6$-$C_{13}$ aryl or unsubstituted or substituted $C_6$-$C_{20}$-aryl (including the $C_6$-$C_{20}$-aryl moieties of $C_6$-$C_{20}$-aryl-$C_1$-$C_4$-alkyl, di($C_6$-$C_{20}$-aryl)-$C_1$-$C_4$-alkyl or $C_6$-$C_{20}$-aryloxy).

The term "heteroaryl" as used herein refers to a monocyclic or bicyclic heteroaromatic ring, which typically contains from five to ten atoms in the ring portion including one or more heteroatoms), each of which may be unsubstituted or substituted, such as a group being identified herein as unsubstituted or substituted $C_3$-$C_{20}$-heteroaryl. A heteroaryl group contains at least one heteroatom selected from N, O, S, S(O) and $S(O)_2$. It may contain, for example, one, two, three or four, e.g. one or two, heteroatoms. Examples of heteroaryl groups include indolyl, pyridyl, pyrazinyl, pyrimidinyl, pyridazinyl, furanyl, thienyl, pyrazolidinyl, pyrrolyl, tetrazolyl, oxazolyl, oxadiazolyl, isoxazolyl, thiadiazolyl, thiazolyl, isothiazolyl, imidazolyl, pyrazolyl, quinolyl and isoquinolyl.

The compound of formula (II), i.e. the dienophile, and the compound of formula (III), i.e. the diene, used as the starting materials are either commercially available or can be prepared according to known methods. For example, the dienophile (II) may be prepared by the procedure as described in J. Tamariz, P. Vogel, P. Helv. Chim. Acta 1981, 64, pages 2928-2930. Methods for the synthesis of the dienes (III) are described e.g. in Ullmann's Encyclopedia of Industrial Chemistry, Vol. 20, H. M. Weitz, P. E. Loser, "Isoprene," Wiley, 2012, p. 83.

The advantages of the process according to the invention become particularly apparent when, in the compounds of formulae (I), (II) and (III), the substituents are each independently defined as follows, more preferably in combination:
$R^1$ is $C_1$-$C_4$-alkyl, in particular methyl;
$R^2$ is hydrogen;
$R^3$ is hydrogen;
$R^4$ is hydrogen;
$R^5$ is hydrogen;
$R^6$ is hydrogen or $C_1$-$C_4$-alkyl, more preferably $C_1$-$C_4$-alkyl, in particular methyl;
$R^7$ is $C_1$-$C_4$-alkyl or hydrogen, more preferably methyl or hydrogen and in particular hydrogen;
$R^8$ is hydrogen;
$R^9$ is hydrogen; or
$R^5$ and $R^8$ together form a bridging moiety —$CH_2$—$CH_2$— between the carbon atoms to which they are connected;
Y is $OC(O)R_A$ wherein $R_A$ is selected from $C_1$-$C_8$-alkyl, $C_3$-$C_{12}$-cycloalkyl, unsubstituted or substituted $C_6$-$C_{20}$-aryl and di($C_6$-$C_{20}$-aryl)-$C_1$-$C_4$-alkyl, more preferably from $C_1$-$C_8$-alkyl, $C_3$-$C_{12}$-cycloalkyl, $C_6$-$C_{20}$-aryl and di($C_6$-$C_{20}$-aryl)-$C_1$-$C_4$-alkyl, even more preferably from $C_6$-$C_{20}$-aryl and di($C_6$-$C_{20}$-aryl)-$C_1$-$C_4$-alkyl, in particular phenyl and diphenylmethyl.

A particularly preferred embodiment relates to a process for the synthesis of a non-racemic cyclohexene compound of formula I wherein
$R^1$ and $R^6$ are both $C_1$-$C_4$-alkyl;
$R^2$, $R^3$, $R^4$, $R^5$, $R^7$, $R^8$ and $R^9$ are each hydrogen;
Y is $OC(O)R_A$ wherein $R_A$ is selected from $C_6$-$C_{20}$-aryl and di($C_6$-$C_{20}$-aryl)-$C_1$-$C_4$-alkyl.

An especially preferred embodiment relates to a process for the synthesis of a non-racemic cyclohexene compound of formula I wherein
$R^1$ and $R^6$ are both methyl;
$R^2$, $R^3$, $R^4$, $R^5$, $R^7$, $R^8$ and $R^9$ are each hydrogen;
Y is $OC(O)R_A$ wherein $R_A$ is phenyl or diphenylmethyl.

Such compounds correspond to 1-acetyl-4-methylcyclohex-3-en-1-yl benzoate of the formula (I1) and 1-acetyl-4-methylcyclohex-3-en-1-yl 2,2-diphenylacetate of the formula (I-2) as shown below

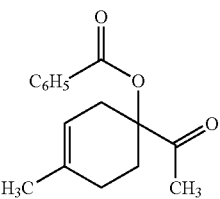

(I-1)

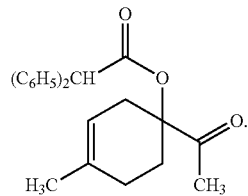

(I-2)

Another particularly preferred embodiment relates to a process for the synthesis of a non-racemic cyclohexene compound of formula I wherein
$R^1$ and $R^6$ are both $C_1$-$C_4$-alkyl;
$R^2$, $R^3$, $R^4$, $R^5$, $R^7$, $R^8$ and $R^9$ are each hydrogen;
Y is $OC(O)R_A$ wherein $R_A$ is selected from $C_1$-$C_8$-alkyl and $C_3$-$C_{12}$-cycloalkyl.

An especially preferred embodiment relates to a process for the synthesis of a non-racemic cyclohexene compound of formula I wherein
$R^1$ and $R^6$ are both methyl;
$R^2$, $R^3$, $R^4$, $R^5$, $R^7$, $R^8$ and $R^9$ are each hydrogen;
Y is $OC(O)R_A$ wherein $R_A$ is 1-adamantyl, methyl or tert-butyl.

Such compounds correspond to 1-acetyl-4-methylcyclohex-3-en-1-yl adamantane-2-carboxylate of the formula (I-3), 1-acetyl-4-methylcyclohex-3-en-1-yl acetate of the formula (I-4) and 1-acetyl-4-methylcyclohex-3-en-1-yl trimethylacetate of the formula (I-5) as shown below

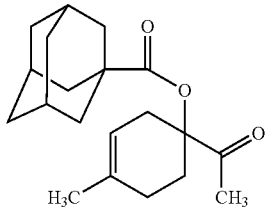

(I-3)

-continued

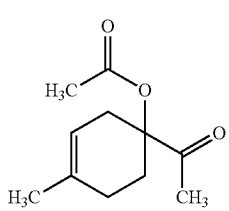

(I-4)

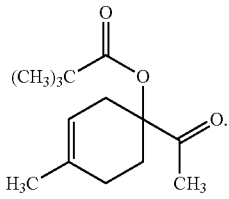

(I-5)

Another particularly preferred embodiment relates to a process for the synthesis of a non-racemic cyclohexene compound of formula I wherein
 $R^1$, $R^6$ and $R^7$ are each $C_1$-$C_4$-alkyl;
 $R^2$, $R^3$, $R^4$, $R^5$, $R^8$ and $R^9$ are each hydrogen;
 Y is $OC(O)R_A$ wherein $R_A$ is selected from $C_6$-$C_{20}$-aryl and di($C_6$-$C_{20}$-aryl)-$C_1$-$C_4$-alkyl.

An especially preferred embodiment relates to a process for the synthesis of a non-racemic cyclohexene compound of formula I wherein
 $R^1$, $R^6$ and $R^7$ are each methyl;
 $R^2$, $R^3$, $R^4$, $R^5$, $R^8$ and $R^9$ are each hydrogen;
 Y is $OC(O)R_A$ wherein $R_A$ is phenyl or diphenylmethyl.

Such compounds correspond to 1-acetyl-3,4-dimethylcyclohex-3-en-1-yl benzoate of the formula (I-6) and 1-acetyl-3,4-dimethylcyclohex-3-en-1-yl 2,2-diphenylacetate of the formula (I-7) as shown below

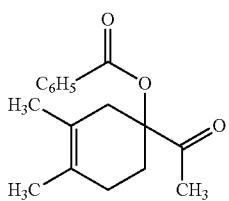

(I-6)

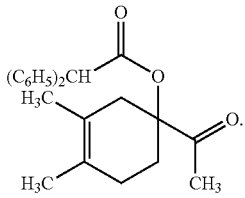

(I-7)

Another particularly preferred embodiment relates to a process for the synthesis of a non-racemic cyclohexene compound of formula I wherein
 $R^1$ is $C_1$-$C_4$-alkyl;
 $R^2$, $R^3$, $R^4$, $R^6$, $R^7$ and $R^9$ are each hydrogen;
 $R^5$ and $R^8$ together form a bridging moiety —$CH_2$—$CH_2$— between the carbon atoms to which they are connected;
 Y is $OC(O)R_A$ wherein $R_A$ is selected from $C_6$-$C_{20}$-aryl, di($C_6$-$C_{20}$-aryl)-$C_1$-$C_4$-alkyl and $C_3$-$C_{12}$-cycloalkyl.

An especially preferred embodiment relates to a process for the synthesis of a non-racemic cyclohexene compound of formula I wherein
 $R^1$ is methyl;
 $R^2$, $R^3$, $R^4$, $R^6$, $R^7$ and $R^9$ are each hydrogen;
 $R^5$ and $R^8$ together form a bridging moiety —$CH_2$—$CH_2$— between the carbon atoms to which they are connected;
 Y is $OC(O)R_A$ wherein $R_A$ is phenyl, diphenylmethyl or 1-adamantyl.

Such compounds correspond to 2-acetylbicyclo[2.2.2]oct-5-en-2-yl benzoate of the formula (I8), 2-acetylbicyclo[2.2.2]oct-5-en-2-yl 2,2-diphenylacetate of the formula (I-9) and 2-acetylbicyclo[2.2.2]oct-5-en-2-yl adamantane-2-carboxylate of the formula (I-10) as shown below

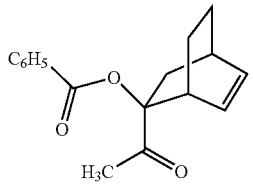

(I-8)

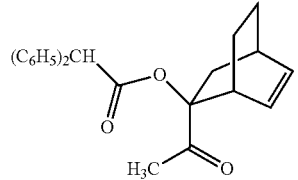

(I-9)

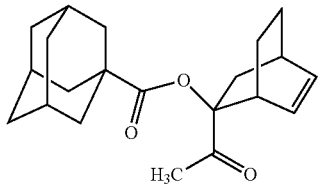

(I-10)

Another particularly preferred embodiment relates to a process for the synthesis of a non-racemic cyclohexene compound of formula I wherein
 $R^1$, $R^6$ and $R^7$ are each $C_1$-$C_4$-alkyl;
 $R^2$, $R^3$, $R^4$, $R^5$, $R^3$ and $R^9$ are each hydrogen;
 Y is $OC(O)R_A$ wherein $R_A$ is selected from $C_6$-$C_{20}$-aryl, preferably $C_{10}$-$C_{14}$-aryl.

An especially preferred embodiment relates to a process for the synthesis of a non-racemic cyclohexene compound of formula I wherein
 $R^1$, $R^6$ and $R^7$ are each methyl;
 $R^2$, $R^3$, $R^4$, $R^5$, $R^3$ and $R^9$ are each hydrogen;
 Y is $OC(O)R_A$ wherein $R_A$ is 1-naphthyl or 2-naphthyl.

Such compounds correspond to 1-acetyl-3,4-dimethylcyclohex-3-en-1-yl 1-naphthoate of the formula (I-11) and 1-acetyl-3,4-dimethylcyclohex-3-en-1-yl 2-naphthoate of the formula (I-12) as shown below (I-11)

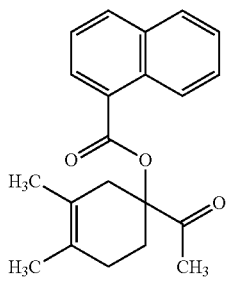

(I-12)

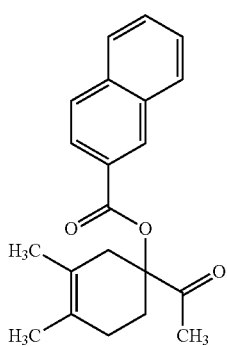

Another particularly preferred embodiment relates to a process for the synthesis of a non-racemic cyclohexene compound of formula I wherein $R^1$ and $R^6$ are both $C_1$-$C_4$-alkyl;

$R^2$, $R^3$, $R^4$, $R^5$, $R^7$, $R^8$ and $R^9$ are each hydrogen;

Y is OC(O)$R_A$ wherein $R_A$ is selected from $C_6$-$C_{20}$-aryl, preferably $C_{10}$-$C_{14}$-aryl.

An especially preferred embodiment relates to a process for the synthesis of a non-racemic cyclohexene compound of formula I wherein $R^1$ and $R^6$ are both methyl;

$R^2$, $R^3$, $R^4$, $R^5$, $R^7$, $R^8$ and $R^9$ are each hydrogen;

Y is OC(O)$R_A$ wherein $R_A$ is 1-naphthyl or 2-naphthyl.

Such compounds correspond to 1-acetyl-4-methylcyclohex-3-en-1-yl 1-naphthoate of the formula (I-13) and 1-acetyl-4-methylcyclohex-3-en-1-yl 2-naphthoate of the formula (I-14) as shown below (I-13)

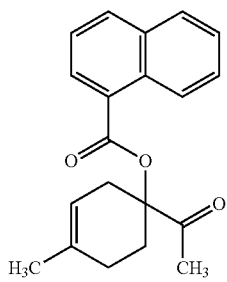

(I-14)

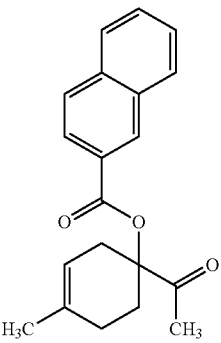

Another particularly preferred embodiment relates to a process for the synthesis of a non-racemic cyclohexene compound of formula I wherein $R^1$ and $R^6$ are both $C_1$-$C_4$-alkyl;

$R^2$, $R^3$, $R^4$, $R^5$, $R^7$, $R^8$ and $R^9$ are each hydrogen;

Y is OC(O)$R_A$ wherein $R_A$ is selected from substituted $C_6$-$C_{20}$-aryl, preferably substituted $C_6$-$C_{10}$-aryl.

An especially preferred embodiment relates to a process for the synthesis of a non-racemic cyclohexene compound of formula I wherein $R^1$ and $R^6$ are both methyl;

$R^2$, $R^3$, $R^4$, $R^5$, $R^7$, $R^8$ and $R^9$ are each hydrogen;

Y is OC(O)$R_A$ wherein $R_A$ is 2-bromophenyl, 4-tert-butylphenyl or 4-nitrophenyl.

Such compounds correspond to 1-acetyl-4-methylcyclohex-3-en-1-yl 2-bromobenzoate of the formula (I-15), 1-acetyl-4-methylcyclohex-3-en-1-yl 4-(tert-butyl)benzoate of the formula (I-16) and 1-acetyl-4-methylcyclohex-3-en-1-yl 4-nitrobenzoate of the formula (I-17) as shown below (I-15)

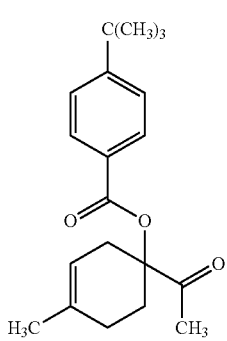

(I-16)

(I-17)

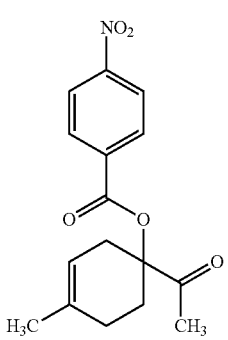

In another particularly preferred embodiment of the compounds of formulae (I) and (II), $R^1$ is $C_1$-$C_4$-alkyl and $R^2$ and $R^3$ are both hydrogen.

In yet another particularly preferred embodiment of the compounds of formulae (I) and (II), $R^1$ is methyl and $R^2$ and $R^3$ are both hydrogen.

In yet another particularly preferred embodiment of the compounds of formulae (I) and (III), $R^6$ is $C_1$-$C_4$-alkyl and $R^4$, $R^5$, $R^7$, $R^8$ and $R^9$ are each hydrogen.

In yet another particularly preferred embodiment of the compounds of formulae (I) and (III), $R^6$ is methyl and $R^4$, $R^5$, $R^7$, $R^3$ and $R^9$ are each hydrogen.

In yet another particularly preferred embodiment of the compounds of formulae (I) and (II), Y is $OC(O)R_A$ wherein $R_A$ is selected from $C_1$-$C_8$-alkyl, $C_3$-$C_{12}$-cycloalkyl, unsubstituted or substituted $C_6$-$C_{20}$-aryl and di($C_6$-$C_{20}$-aryl)-$C_1$-$C_4$-alkyl, more preferably from $C_1$-$C_8$-alkyl, $C_3$-$C_{12}$-cycloalkyl, $C_6$-$C_{20}$-aryl and di($C_6$-$C_{20}$-aryl)-$C_1$-$C_4$-alkyl, even more preferably from $C_3$-$C_{12}$-cycloalkyl, $C_6$-$C_{20}$-aryl and di($C_6$-$C_{20}$-aryl)-$C_1$-$C_4$-alkyl, in particular from $C_6$-$C_{20}$-aryl and di($C_6$-$C_{20}$-aryl)-$C_1$-$C_4$-alkyl.

In yet another particularly preferred embodiment of the compounds of formulae (I) and (II), Y is $OC(O)R_A$ wherein $R_A$ is selected from phenyl, diphenylmethyl, 1-adamantyl, 1-naphthyl, 2-naphthyl, 2-bromophenyl, 4-tert-butylphenyl, 4-nitrophenyl, methyl and tert-butyl, more preferably selected from phenyl, diphenylmethyl, 1-adamantyl, methyl and tert-butyl, even more preferably selected from phenyl, diphenylmethyl and 1-adamantyl and in particular selected from phenyl and diphenylmethyl.

Another particularly preferred embodiment relates to a process for the synthesis of a non-racemic cyclohexene compound of formula I wherein $R^1$ is $C_1$-$C_4$-alkyl;
$R^6$ and $R^7$ are hydrogen or $C_1$-$C_4$-alkyl;
$R^2$, $R^3$, $R^4$, $R^5$, $R^8$ and $R^9$ are each hydrogen; or
$R^2$, $R^3$, $R^4$ and $R^9$ are each hydrogen and $R^5$ and $R^8$ together form a bridging moiety —$CH_2$—$CH_2$—between the carbon atoms to which they are connected;
Y is $OC(O)R_A$ wherein $R_A$ is selected from $C_1$-$C_8$-alkyl, $C_3$-$C_{12}$-cycloalkyl, unsubstituted or substituted $C_6$-$C_{20}$-aryl, and di($C_6$-$C_{20}$-aryl)-$C_1$-$C_4$-alkyl.

An especially preferred embodiment relates to a process for the synthesis of a non-racemic cyclohexene compound of formula I wherein $R^1$ is methyl;
$R^6$ and $R^7$ are hydrogen or methyl;
$R^2$, $R^3$, $R^4$, $R^5$, $R^3$ and $R^9$ are each hydrogen; or
$R^2$, $R^3$, $R^4$ and $R^9$ are each hydrogen and $R^5$ and $R^8$ together form a bridging moiety —$CH_2$—$CH_2$—between the carbon atoms to which they are connected;

Y is $OC(O)R_A$ wherein $R_A$ is selected from phenyl, diphenylmethyl, 1-adamantyl, 1-naphthyl, 2-naphthyl, 2-bromophenyl, 4-tert-butylphenyl, 4-nitrophenyl, methyl and tert-butyl.

In another preferred embodiment, the non-racemic cyclohexene compound of formula (I) is selected from (S)-1-acetyl-4-methylcyclohex-3-en-1-yl benzoate of the formula ((S)-I-1)

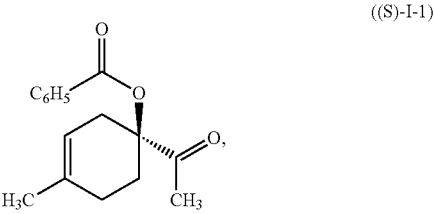

((S)-I-1)

(S)-1-acetyl-4-methylcyclohex-3-en-1-yl 2,2-diphenylacetate of the formula ((S)-1-2)

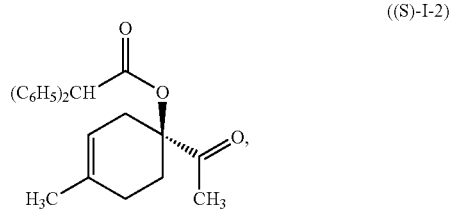

((S)-I-2)

(S)-1-acetyl-4-methylcyclohex-3-en-1-yl adamantane-2-carboxylate of the formula ((S)-1-3)

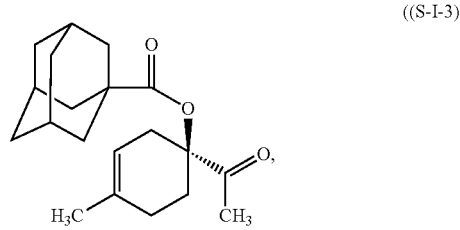 [SMILES: CC(=O)[C@@]1(OC(=O)C23CC4CC(CC(C4)C2)C3)CC=C(C)CC1]

((S-I-3)

(S)-1-acetyl-4-methylcyclohex-3-en-1-yl acetate of the formula ((S)-1-4)

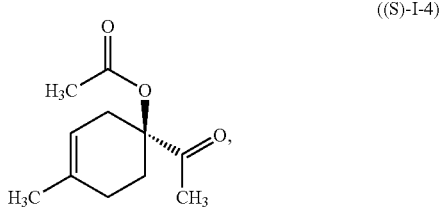

((S)-I-4)

and (S)-1-acetyl-4-methylcyclohex-3-en-1-yl trimethylacetate of the formula ((S)-I-5)

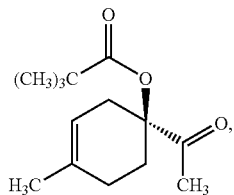

((S)-I-5)

In another embodiment, the non-racemic cyclohexene compound of formula (I) is selected from (S)-1-acetyl-4-methylcyclohex-3-en-1-yl benzoate of the formula ((S)-I-1), (S)-1-acetyl-4-methylcyclohex-3-en-1-yl 2,2-diphenylacetate of the formula ((S)-1-2), (S)-1-acetyl-4-methylcyclohex-3-en-1-yl adamantane-2-carboxylate of the formula ((S)-1-3), (S)-1-acetyl-4-methylcyclohex-3-en-1-yl acetate of the formula ((S)-1-4), and (S)-1-acetyl-4-methylcyclohex-3-en-1-yl trimethylacetate of the formula ((S)-1-5), in each case having an enantiomeric excess (ee) of preferably at least 75%, more preferably of at least 80%, even more preferably of at least 85%, yet more preferably of at least 90% and in particular of at least 95%, for example at least 97%.

In yet another preferred embodiment, the non-racemic cyclohexene compound of formula (I) is selected from (R)-1-acetyl-4-methylcyclohex-3-en-1-yl benzoate of the formula ((R)-I-1)

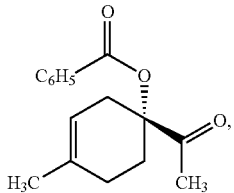

((R)-I-1)

(R)-1-acetyl-4-methylcyclohex-3-en-1-yl 2,2-diphenylacetate of the formula ((R)-I-2)

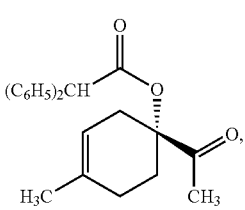

((R)-I-2)

(R)-1-acetyl-4-methylcyclohex-3-en-1-yl adamantane-2-carboxylate of the formula ((R)-I-3)

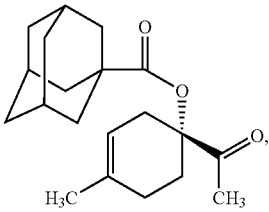

((R)-I-3)

(R)-1-acetyl-4-methylcyclohex-3-en-1-yl acetate of the formula ((R)-I-4)

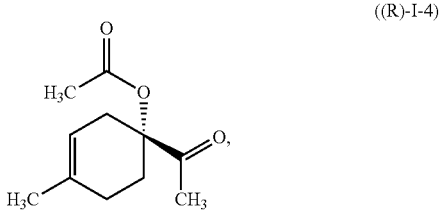

((R)-I-4)

and (R)-1-acetyl-4-methylcyclohex-3-en-1-yl trimethylacetate of the formula ((R)-I-5)

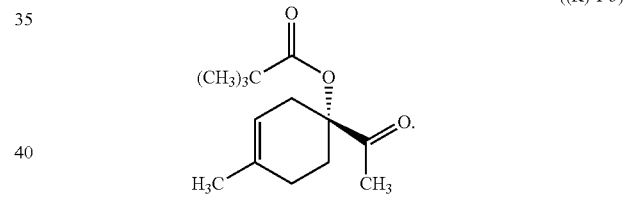

((R)-I-5)

In another embodiment, the non-racemic cyclohexene compound of formula (I) is selected from (R)-1-acetyl-4-methylcyclohex-3-en-1-yl benzoate of the formula ((R)-I-1), (R)-1-acetyl-4-methylcyclohex-3-en-1-yl 2,2-diphenylacetate of the formula ((R)-I-2), (R)-1-acetyl-4-methylcyclohex-3-en-1-yl adamantane-2-carboxylate of the formula ((R)-I-3), (R)-1-acetyl-4-methylcyclohex-3-en-1-yl acetate of the formula ((R)-I-4), and (R)-1-acetyl-4-methylcyclohex-3-en-1-yl trimethylacetate of the formula ((R)-I-5), in each case having an enantiomeric excess (ee) of preferably at least 75%, more preferably of at least 80%, even more preferably of at least 85%, yet more preferably of at least 90% and in particular of at least 95%, for example at least 97%.

In a preferred embodiment, the substituents $R^1$, $R^2$, $R^3$ and Y in the compound of formula (II) have the following meanings:
  $R^1$ is methyl;
  $R^2$ and $R^3$ are both hydrogen; and
  Y is $OC(O)R_A$ wherein $R_A$ is from selected from phenyl, diphenylmethyl, 1-adamantyl, methyl and tert-butyl.

In an especially preferred embodiment, the substituents $R^1$, $R^2$, $R^3$ and Y in the compound of formula (II) have the following meanings:

$R^1$ is methyl;

$R^2$ and $R^3$ are both hydrogen; and

Y is $OC(O)R_A$ wherein $R_A$ is selected from phenyl, diphenylmethyl and 1-adamantyl.

Such compounds correspond to 3-oxobut-1-en-2-yl benzoate of the formula (II-1), 3-oxobut-1-en-2-yl 2,2-diphenylacetate of the formula (II-2) and oxobut-1-en-2-yl adamantane-2-carboxylate of the formula (II-3)

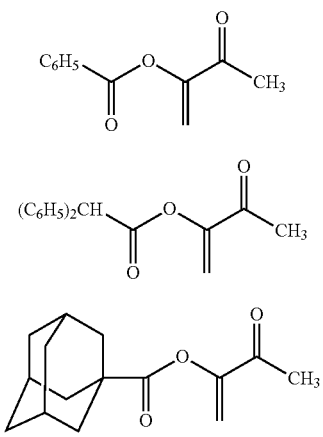

In another especially preferred embodiment, the substituents $R^1$, $R^2$, $R^3$ and Y in the compound of formula (II) have the following meanings:

$R^1$ is methyl;

$R^2$ and $R^3$ are both hydrogen; and

Y is $OC(O)R_A$ wherein $R_A$ is selected from 1-naphthyl, 2-naphthyl, tert-butyl, 2-bromophenyl, 4-tert-butylphenyl and 4-nitrophenyl.

Such compounds correspond to 3-oxobut-1-en-2-yl 1-naphthoate of the formula (II-4), 3-oxobut-1-en-2-yl 2-naphthoate of the formula (II-5), (1-methylene-2-oxo-propyl) 2,2-diphenylacetate of the formula (II-6), (1-methylene-2-oxo-propyl) 2-bromobenzoate of the formula (II-7), (1-methylene-2-oxo-propyl) 4-tert-butylbenzoate of the formula (II-8) and 3-oxobut-1-en-2-yl 4-nitrobenzoate of the formula (II-9).

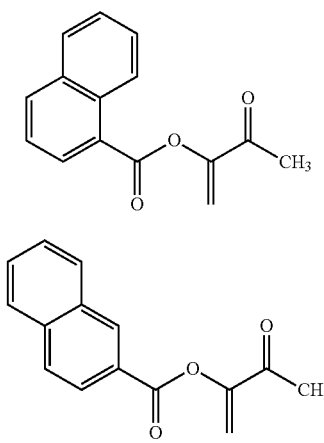

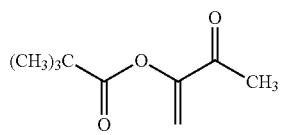

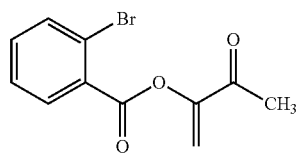

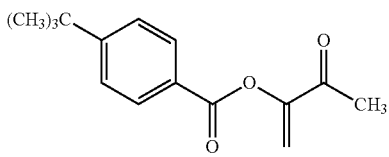

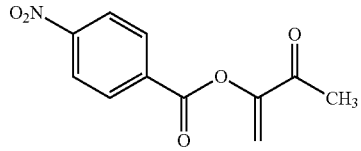

In another especially preferred embodiment, the substituents $R^1$, $R^2$, $R^3$ and Y in the compound of formula (II) have the following meanings:

$R^1$ is $C_1$-$C_4$-alkyl;

$R^2$ and $R^3$ are both hydrogen; and

Y is $OC(O)R_A$ wherein $R_A$ is selected from $C_1$-$C_8$-alkyl, $C_3$-$C_{12}$-cycloalkyl, unsubstituted or substituted $C_6$-$C_{20}$-aryl, and di($C_6$-$C_{20}$-aryl)-$C_1$-$C_4$-alkyl.

In another especially preferred embodiment, the substituents $R^1$, $R^2$, $R^3$ and Y in the compound of formula (II) have the following meanings:

$R^1$ is methyl;

$R^2$ and $R^3$ are both hydrogen; and

Y is $OC(O)R_A$ wherein $R_A$ is selected from phenyl, diphenylmethyl, 1-adamantyl, 1-naphthyl, 2-naphthyl, 2-bromophenyl, 4-tert-butylphenyl, 4-nitrophenyl, methyl and tert-butyl.

In a particularly preferred embodiment, the substituents $R^4$, $R^5$, $R^6$, $R^7$, $R^3$ and $R^9$ in the compound of formula (III) have the following meanings:

$R^4$, $R^5$, $R^3$ and $R^9$ are each hydrogen;

$R^6$ is hydrogen or methyl, $R^7$ is hydrogen or methyl; or $R^5$ and $R^8$ together form a bridging moiety —$CH_2$—$CH_2$— between the carbon atoms to which they are connected.

In an especially preferred embodiment, the substituents $R^4$, $R^5$, $R^6$, $R^7$, $R^3$ and $R^9$ in the compound of formula (III) have the following meanings:

$R^4$, $R^5$, $R^7$, $R^3$ and $R^9$ are each hydrogen; and $R^6$ is methyl.

Such a compound corresponds to 2-methyl-1,3-butadiene of the formula (III-1) (also known under the common name isoprene)

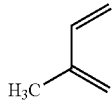

(III-1)

In another especially preferred embodiment, the substituents $R^4$, $R^5$, $R^6$, $R^7$, $R^8$ and $R^9$ in the compound of formula (III) have the following meanings:
$R^4$, $R^5$, $R^8$ and $R^9$ are each hydrogen; and
$R^6$ and $R^7$ are both methyl.

Such a compound corresponds to 2,3-dimethyl-1,3-butadiene of the formula (III-2)

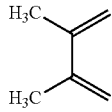

(III-2)

In another especially preferred embodiment, the substituents $R^4$, $R^5$, $R^6$, $R^7$, $R^8$ and $R^9$ in the compound of formula (III) have the following meanings:
$R^4$, $R^6$, $R^7$ and $R^9$ are each hydrogen; and
$R^5$ and $R^8$ together form a bridging moiety —$CH_2$—$CH_2$— between the carbon atoms to which they are connected.

Such a compound corresponds to 1,3-cyclohexadiene of the formula (III-3)

(III-3)

The compound of the formula (II) can be reacted with the compound of the formula (III) in essentially equimolar amounts, or one of the compounds (II) or (III) is used in a slight excess. In a preferred embodiment, the molar ratio of the compound of the formula (II) to the compound of the formula (III) is from 1:1 to 1:40, more preferably from 1:2 to 1:30, even more preferably from 1:5 to 1:20 and in particular from 1:10 to 1:20. In one embodiment, unreacted compound of the formula (III) is recovered from the crude reaction mixture, preferably by rectification, and recycled.

The process of this invention is conducted in the presence of a catalyst comprising at least one m-valent metal cation $M^{m+}$ wherein the metal M is selected from Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Gallium (Ga) and Indium (In), and m is an integer of 1, 2 or 3, and a chiral ligand of the formula (IV) as depicted hereinabove.

Preferably, the metal M in the m-valent metal cation $M^{m+}$ is selected from Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb) and Lutetium (Lu), even more preferably from Scandium (Sc), Yttrium (Y), Terbium (Tb) and Ytterbium (Yb), yet more preferably from Yttrium (Y) and Ytterbium (Yb) and is in particular Ytterbium (Yb). In another particularly preferred embodiment, the metal M in the m-valent metal cation $M^{m+}$ is Yttrium (Y).

In another preferred embodiment, m is an integer of 2 or 3, in particular 3. Thus, the m-valent metal cation $M^{m+}$ is preferably $M^{2+}$ or $M^{3+}$, in particular $M^{3+}$.

In yet another preferred embodiment, the metal M and m in the m-valent metal cation $M^{m+}$ have the following meanings:
M is selected from Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb) and Lutetium (Lu), even more preferably from Scandium (Sc), Yttrium (Y), Terbium (Tb) and Ytterbium (Yb), yet more preferably from Yttrium (Y) and Ytterbium (Yb) and is in particular Ytterbium (Yb); and
m is an integer of 2 or 3, in particular 3.

In yet another particularly preferred embodiment, the metal M and m in the m-valent metal cation $M^{m+}$ have the following meanings:
M is Yttrium (Y); and
m is an integer of 2 or 3, in particular 3.

In an especially preferred embodiment, the m-valent metal cation $M^{m+}$ is selected from $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$, even more preferably from $Sc^{3+}$, $Y^{3+}$, $Tb^{3+}$ and $Yb^{3+}$, yet more preferably from $Y^{3+}$ and $Yb^{3+}$ and is in particular $Yb^{3+}$. In another particularly preferred embodiment, the m-valent metal cation $M^{m+}$ is $Y^{3+}$.

In another preferred embodiment, the catalyst additionally comprises at least one n-valent anion $A^{n-}$ wherein n is an integer of 1, 2 or 3 and is in particular 1. More preferably, the catalyst additionally comprises one, two or three n-valent anions $A^{n-}$ wherein n is an integer of 1, 2 or 3, even more preferably one, two or three n-valent anions $A^{n-}$ wherein n is an integer of 1 (i.e. $A^-$). In cases in which the catalyst comprises two or three n-valent anions $A^{n-}$, the anions can be the same or different.

In a preferred embodiment, the n-valent anion $A^{n-}$ is independently selected from halide, tetrafluoroborate ($BF_4^-$), tetrakis[3,5-bis(trifluoromethyl)phenyl]borate ([{3,5-$(CF_3)_2C_6H_3$}$_4$B]$^-$), perchlorate ($ClO_4^-$), hexafluorophosphate ($PF_6^-$), antimony hexafluoride ($SbF_6^-$), nitrate ($NO_3^-$), a sulfonate anion of the formula $R^{12}SO_3^-$ wherein $R^{12}$ is selected from $C_1$-$C_4$-alkyl, $C_1$-$C_4$-haloalkyl and unsubstituted or substituted $C_6$-$C_{20}$-aryl, a carboxylate ion of the formula $R^{13}COO^-$ wherein $R^{13}$ is selected from hydrogen, $C_1$-$C_8$-alkyl, $C_3$-$C_{12}$-cycloalkyl, $C_1$-$C_8$-haloalkyl and unsubstituted or substituted $C_6$-$C_{20}$-aryl, sulfate ($SO_4^{2-}$), and a bis(sulfonyl)imide anion of the formula ($R^{14}SO_2$)$_2$N$^-$, wherein $R^{14}$ is selected from $C_1$-$C_4$-alkyl, $C_1$-$C_4$-haloalkyl and unsubstituted or substituted $C_5$-$C_{20}$-aryl.

Examples of halides include fluoride, chloride, bromide or iodide, preferably fluoride or chloride and in particular chloride.

Examples of a sulfonate anion of the formula $R^{12}SO_3^-$ wherein $R^{12}$ is selected from $C_1$-$C_4$-alkyl include mesylate (methanesulfonate), esylate (ethanesulfonate), n-propylsulfonate, iso-propylsulfonate, n-butylsulfonate, iso-butylsulfonate, sec-butylsulfonate and tert-butylsulfonate.

Examples of a sulfonate anion of the formula $R^{12}SO_3^-$ wherein $R^{12}$ is selected from $C_1$-$C_4$-haloalkyl include triflate (trifluoromethanesulfonate), trichloromethanesulfonate and 1,1,2,2,3,3,4,4-nonafluorobutane-sulfonate.

Examples of a sulfonate anion of the formula $R^{12}SO_3^-$ wherein $R^{12}$ is selected from unsubstituted or substituted $C_6$-$C_{20}$-aryl include tosylate (p-toluenesulfonate), besylate (benzenesulfonate), 2-naphtyl sulfonate and nosylate.

Preferred substituents for $R^{12}$ are selected from methyl, trifluoromethyl and p-tolyl, more preferably trifluoromethyl. Thus, the sulfonate anion of the formula $R^{12}SO_3^-$ is preferably selected from mesylate, triflate and tosylate, and is in particular triflate.

Examples of a carboxylate ion of the formula $R^{13}COO^-$ wherein $R^{13}$ is selected from $C_1$-$C_8$-alkyl include formate, acetate, propionate, butyrate, pentanoate, hexanoate, heptanoate and octanoate.

Examples of a carboxylate ion of the formula $R^{13}COO^-$ wherein $R^{13}$ is selected from $C_3$-$C_{12}$-cycloalkyl include cyclohexanoate and cyclopropylnoate.

Examples of a carboxylate ion of the formula $R^{13}COO^-$ wherein $R^{13}$ is selected from $C_1$-$C_8$-haloalkyl include trifluoroacetate, chloroacetate and 2,2,3,3,4,4,5,5,5-nonafluoropentoate.

Examples of a carboxylate ion of the formula $R^{13}COO^-$ wherein $R^{13}$ is selected from unsubstituted or substituted $C_6$-$C_{20}$-aryl include benzoate, chlorobenzoate, o-toluate, p-toluate, 1-naphthoate and 2-naphthoate.

Preferred substituents for $R^{13}$ are selected from methyl and phenyl, in particular methyl. Thus, the carboxylate ion of the formula $R^{13}COO^-$ is preferably selected from acetate and benzoate, and is in particular acetate.

Examples of a bis(sulfonyl)imide anion of the formula $(R^{14}SO_2)_2N^-$, wherein $R^{14}$ is selected from $C_1$-$C_4$-alkyl (in particular methyl or ethyl) include N-methylsulfonylmethanesulfonamide and N-ethylsulfonylethanesulfonamide.

Examples of a bis(sulfonyl)imide anion of the formula $(R^{14}SO_2)_2N^-$, wherein $R^{14}$ is selected from $C_1$-$C_4$-haloalkyl (in particular trifluoromethyl) include bistriflimide (bis(trifluoromethane)sulfonimide).

Examples of a bis(sulfonyl)imide anion of the formula $(R^{14}SO_2)_2N^-$, wherein $R^{14}$ is selected from unsubstituted or substituted $C_6$-$C_{20}$-aryl (in particular p-tolyl) include bis(4-methylbenzene)sulfonimide.

Preferred substituents for $R^{14}$ are selected from trifluoromethyl and p-tolyl, in particular trifluoromethyl. Thus, the bis(sulfonyl)imide anion of the formula $(R^{14}SO_2)_2N^-$ is preferably bistriflimide (bis(trifluoromethane)sulfonimide) and bis(4-methylbenzene)sulfonimide, in particular bistriflimide (bis(trifluoromethane)sulfonimide).

In a particularly preferred embodiment, the n-valent anion $A^{n-}$ is selected from halide and a sulfonate anion of the formula $R^{12}SO_3^-$ wherein $R^{12}$ is selected from $C_1$-$C_4$-alkyl and $C_1$-$C_4$-haloalkyl, more preferably from chloride, mesylate (methanesulfonate) and triflate (trifluoromethanesulfonate), and in particular is triflate (trifluoromethanesulfonate). In another particularly preferred embodiment, the n-valent anion $A^{n-}$ is selected from halide and is in particular chloride.

In another especially preferred embodiment, the metal salt of the formula $[M^{m+}]_n[A^{n-}]_m$ is selected from Scandium(II) chloride, Yttrium(III) chloride, Lanthanum(II) chloride, Cerium(II) chloride, Praseodymium(III) chloride, Neodymium(III) chloride, Promethium(III) chloride, Samarium(IIII) chloride, Europium(III) chloride, Gadolinium(III) chloride, Terbium(II) chloride, Dysprosium(III) chloride, Holmium (III) chloride, Erbium(III) chloride, Thulium(III) chloride, Ytterbium(III) chloride, Lutetium(III) chloride, Scandium (III) triflate, Yttrium(III) triflate, Lanthanum(III) triflate, Cerium(III) triflate, Praseodymium(II) triflate, Neodymium (III) triflate, Promethium(III) triflate, Samarium(III) triflate, Europium(III) triflate, Gadolinium(III) triflate, Terbium(II) triflate, Dysprosium(III) triflate, Holmium(III) triflate, Erbium(III) triflate, Thulium(II) triflate, Ytterbium(III) triflate and Lutetium(III) triflate, more preferably from Scandium(II) triflate, Terbium(II) triflate, Yttrium(III) triflate and Ytterbium(III) triflate, even more preferably from Yttrium (III) triflate and Ytterbium(III) triflate and is in particular Ytterbium(III) triflate. In another especially preferred embodiment, the metal salt of the formula $[M^{m+}]_n[A^{n-}]_m$ is Yttrium(III) chloride or Ytterbium(III) chloride. In one embodiment, the metal salt of the formula $[M^{m+}]_n[A^{n-}]_m$ is Yttrium(III) chloride. In another embodiment, the metal salt of the formula $[M^{m+}]_n[A^{n-}]_m$ is Ytterbium(II) chloride.

The aforementioned metal salts are commercially available or can be prepared by methods known in the art.

The molar ratio of the metal salt of the formula $[M^{m+}]_n[A^{n-}]_m$ (V) to the compound of the formula (II) can vary widely and depends on the reactants and reaction conditions used, but is generally from 1:5 to 1:10000, preferably 1:10 to 1:1000, more preferably from 1:10 to 1:200.

Each of the chiral ligands of formula (IV) as described herein may be an S isomer or R isomer. In a preferred embodiment, it is an S isomer. In another preferred embodiment, it is an R isomer. Further, a non-racemic mixture of an S isomer and an R isomer may be used. In this regard, the term "non-racemic mixture" as used herein means that one of the S- or R-isomers is contained in a larger amount in the mixture than that of the other isomer. Preferably, the ratio of the two isomers is at least 1.5:1, preferably at least 3:1, more preferably at least 10:1, especially preferably at least 50:1, and most preferably at least 100:1.

In a preferred embodiment of the chiral ligand of formula (IV), $R^{10a}$ and $R^{10a'}$ are independently selected from $C_1$-$C_8$-alkyl, $C_3$-$C_6$-cycloalkyl, unsubstituted or substituted $C_6$-$C_{20}$-aryl, $C_6$-$C_{20}$-aryl$C_1$-$C_4$-alkyl and unsubstituted or substituted $C_3$-$C_{20}$-heteroaryl, and $R^{10b}$, $R^{10c}$, $R^{10d}$, $R^{10b'}$, $R^{10c'}$ and $R^{10d'}$ are each hydrogen. In another preferred embodiment, $R^{10a}$ and $R^{10a'}$ are the same and are selected from $C_1$-$C_8$-alkyl, $C_3$-$C_6$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$-heteroaryl, and $R^{10b}$, $R^{10c}$, $R^{10d}$, $R^{10b'}$, $R^{10c'}$ and $R^{10d'}$ are each hydrogen.

In another preferred embodiment of the chiral ligand of formula (IV), $R^{10b}$ and $R^{10b'}$ are independently selected from $C_1$-$C_8$-alkyl, $C_3$-$C_5$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$-heteroaryl, and $R^{10a}$, $R^{10c}$, $R^{10d}$, $R^{10a'}$, $R^{10c'}$ and $R^{10d'}$ are each hydrogen. In another preferred embodiment, $R^{10b}$ and $R^{10b'}$ are the same and are selected from $C_1$-$C_8$-alkyl, $C_3$-$C_6$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$-heteroaryl, and $R^{10a}$, $R^{10c}$, $R^{10d}$, $R^{10b'}$, $R^{10c'}$ and $R^{10d'}$ are each hydrogen.

In another preferred embodiment, $R^{10a}$ and $R^{10a'}$ are the same, $R^{10b}$ and $R^{10b'}$ are the same, $R^{10c}$ and $R^{10c'}$ are the same, and $R^{10d}$ and $R^{10d'}$ are the same, and each of $R^{10a}/R^{10a'}$, $R^{10b}/R^{10b'}$, $R^{10c}/R^{10c'}$, and $R^{10d}/R^{10d'}$ are independently selected from hydrogen, $C_1$-$C_8$-alkyl, $C_3$-$C_6$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$- heteroaryl, provided that at least one pair of $R^{10a}/R^{10a'}$, $R^{10b}/R^{10b'}$, $R^{10c}/R^{10c'}$, and $R^{10d}/R^{10d'}$ is not hydrogen, and at least one pair of $R^{10a}/R^{10a'}$, $R^{10b}/R^{10b'}$, $R^{10c}/R^{10c'}$, and $R^{10d}/R^{10d'}$ is hydrogen.

In another preferred embodiment of the chiral ligand of formula (IV), $R^{11a}$, $R^{11b}$ and $R^{11c}$ are each hydrogen.

In another preferred embodiment of the chiral ligand of formula (IV), $R^{11a}$ and $R^{11c}$ are both hydrogen, and $R^{11b}$ is selected from halogen, cyano, $C_1$-$C_8$-alkyl, $C_1$-$C_4$-haloalkyl and $C_1$-$C_8$-alkoxy, more preferably from halogen, $C_1$-$C_8$-alkyl and $C_1$-$C_8$-alkoxy. In an especially preferred embodiment of the chiral ligand of formula (IV), $R^{11a}$ and $R^{11c}$ are both hydrogen, and $R^{11b}$ is selected from chlorine, cyano, methyl, ethyl, n-propyl, isopropyl, trifluoromethyl and methoxy and even more preferably from chlorine, methyl and methoxy.

In another preferred embodiment of the chiral ligand of formula (IV), Z and Z' are the same and selected from —O—, —O—CH$_2$—,

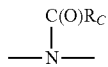

wherein $R_C$ is selected from $C_1$-$C_8$-alkyl, $C_3$—C-cycloalkyl, $C_1$-$C_8$-haloalkyl, and unsubstituted or substituted $C_6$-$C_{13}$ aryl.

More preferably, Z and Z' in the chiral ligand of formula (IV) are the same and selected from —O— and

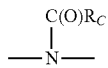

wherein $R_C$ is selected from unsubstituted or substituted $C_6$-$C_{13}$ aryl. Even more preferably, Z and Z' in the chiral ligand of formula (IV) are the same and selected from —O— and

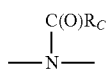

wherein $R_C$ is selected from unsubstituted $C_6$-$C_{13}$ aryl. Even more preferably, Z and Z' in the chiral ligand of formula (IV) are the same and selected from —O— and

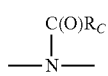

wherein $R_C$ is 1-naphthyl. Still more preferably, Z and Z' in the chiral ligand of formula (IV) are both —O—.

In another preferred embodiment of the chiral ligand of formula (IV), Z and Z' are the same and selected from

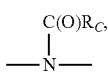

and $R^{10a}$, $R^{10b}$, $R^{10c}$, $R^{10d}$, $R^{10a'}$, $R^{10b'}$, $R^{10c'}$ and $R^{10d'}$ are each independently selected from hydrogen or unsubstituted or substituted $C_6$-$C_{20}$-aryl.

In another preferred embodiment of the chiral ligand of formula (IV), Z and Z' are the same and selected from

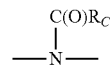

and $R_C$ is selected from unsubstituted or substituted $C_6$-$C_{13}$ aryl.

In another preferred embodiment of the chiral ligand of formula (IV), Z and Z' are the same and selected from

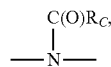

and $R^{10a}$, $R^{10b}$, $R^{10c}$, $R^{10d}$, $R^{10a'}$ $R^{10b'}$, $R^{10c'}$ and $R^{10d'}$ are each independently selected from hydrogen or unsubstituted or substituted $C_6$-aryl.

In another preferred embodiment of the chiral ligand of formula (IV), Z and Z' are the same and selected from

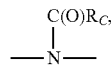

and $R^{10a}$, $R^{10b}$, $R^{10c}$, $R^{10d}$, $R^{10a'}$ $R^{10b'}$, $R^{10c'}$ and $R^{10d'}$ are each independently selected from hydrogen or phenyl.

In another preferred embodiment of the chiral ligand of formula (IV), Z and Z' are the same and selected from

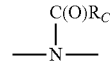

and $R_C$ is 1-Naphthyl.

In another preferred embodiment of the chiral ligand of formula (IV), Z and Z' are the same and selected from

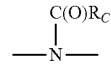

and $R^{11b}$ is halogen.

In another preferred embodiment of the chiral ligand of formula (IV), Z and Z' are the same and selected from

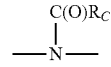

and $R^{11b}$ is chlorine.

In another preferred embodiment of the chiral ligand of formula (IV), $R^{11a}$ and $R^{11c}$ are both hydrogen, and $R^{11b}$ is halogen, in particular chlorine.

In another preferred embodiment of the chiral ligand of formula (IV), $R^{11a}$ and $R^{11c}$ are both hydrogen, and $R^{11b}$ is chlorine.

In another preferred embodiment of the chiral ligand of formula (IV), $R^{10a}$ and $R^{10a'}$ are both phenyl and $R^{10b}$, $R^{10c}$, $R^{10d}$, $R^{10b'}$ $R^{10c'}$ $R^{10d'}$, $R^{11a}$, $R^{11b}$ and $R^{11c}$ are each hydrogen.

In another preferred embodiment of the chiral ligand of formula (IV), $R^{10b}$ and $R^{10b'}$ are both phenyl and $R^{10a}$, $R^{10c}$, $R^{10d}$, $R^{10a'}$, $R^{10c'}$ $R^{10d'}$, $R^{11a}$, $R^{11b}$ and $R^{11c}$ are each hydrogen.

In another preferred embodiment of the chiral ligand of formula (IV), $R^{10a}$, $R^{10a'}$, $R^{10d}$ and $R^{10d'}$ are the same and are selected from $C_1$-$C_8$-alkyl, $C_3$-$C_6$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$-heteroaryl, and $R^{10b}$, $R^{10c}$, $R^{10b'}$, and $R^{10c'}$ are each hydrogen.

In another preferred embodiment of the chiral ligand of formula (IV), $R^{10b}$, $R^{10b'}$, $R^{10c}$, and $R^{10c'}$ are the same and are selected from $C_1$-$C_8$-alkyl, $C_3$-$C_6$-cycloalkyl, unsubstituted or substituted $C_6$-$C_{20}$-aryl, $C_6$-$C_{20}$-aryl-$C_1$-$C_4$-alkyl and unsubstituted or substituted $C_3$-$C_{20}$-heteroaryl, and $R^{10a}$, $R^{10d}$, $R^{10a'}$ and $R^{10d'}$ are each hydrogen.

Further preferred embodiments of the chiral ligand of formula (IV) are as follows:

a chiral ligand of the formula (IVa)

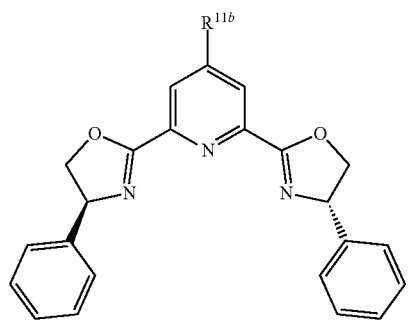

(IVa)

wherein $R^{11b}$ is selected from hydrogen, halogen, $C_1$-$C_8$-alkyl and $C_1$-$C_8$-alkoxy, preferably from hydrogen, chlorine, methyl and methoxy.

a chiral ligand of the formula (IVb)

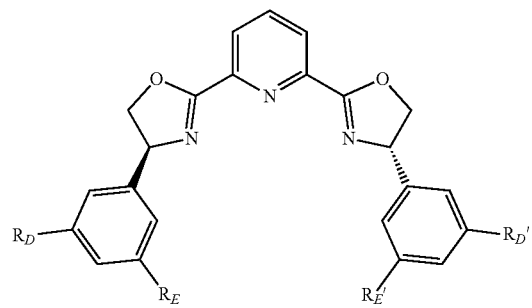

(IVb)

wherein $R_D$, $R_E$, $R_{D'}$ and $R_{E'}$ are each independently selected from and $C_1$-$C_4$-alkyl and $C_1$-$C_4$-alkoxy, preferably from methyl or methoxy. In an especially preferred embodiment of the ligand of formula (IVb), $R_D$, $R_E$, $R_{D'}$ and $R_{E'}$ are each $C_1$-$C_4$-alkyl, in particular methyl. In another especially preferred embodiment of the ligand of formula (IVb), $R_D$, $R_E$, $R_{D'}$ and $R_{E'}$ are each $C_1$-$C_4$-alkoxy, in particular methoxy. Such compounds correspond to the chiral ligands of formulae (IV-4) and (IV-5) as shown hereinbelow.

a chiral ligand of the formula (IVc)

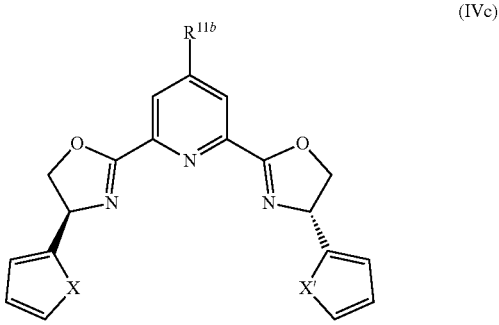

(IVc)

wherein $R^{11b}$ is selected from hydrogen, halogen, $C_1$-$C_8$-alkyl and $C_1$-$C_8$-alkoxy (preferably from hydrogen, chlorine, methyl and methoxy) and X and X' are each independently selected from O and S.

a chiral ligand of the formula (IVd)

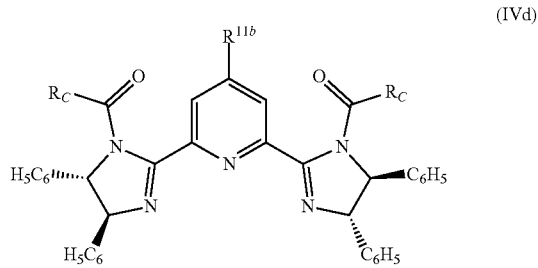

(IVd)

wherein $R^{11b}$ is selected from hydrogen or halogen (in particular chlorine) and both $R_C$ are selected from unsubstituted or substituted $C_6$-$C_{13}$ aryl (preferably 1-naphthyl).

Further preferred chiral ligands of the formula (IV) used in the process of this invention are selected from the chiral ligands of the formulae (IV-1) to (IV-15) as shown hereinbelow:

a chiral ligand of the formula (IV-1), i.e. 2,6-bis((S)-4-phenyl-4,5-dihydrooxazol-2-yl)pyridine of the formula (IV-1)

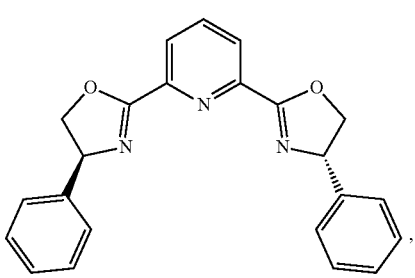

(IV-1)

a chiral ligand of the formula (IV-2), i.e. 2,6-bis((S)-4-(4-bromophenyl)-4,5-dihydrooxazol-2-yl)pyridine of the formula (IV-2)

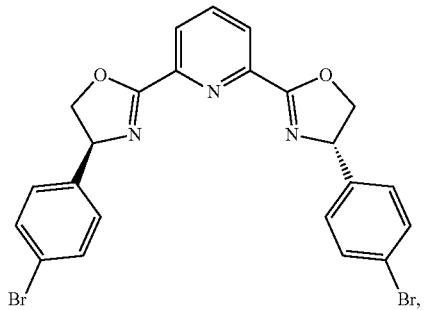

(IV-2)

a chiral ligand of the formula (IV-3), i.e. 2,6-bis((S)-4-(4-methoxyphenyl)-4,5-dihydrooxazol-2-yl)pyridine of the formula (IV-3)

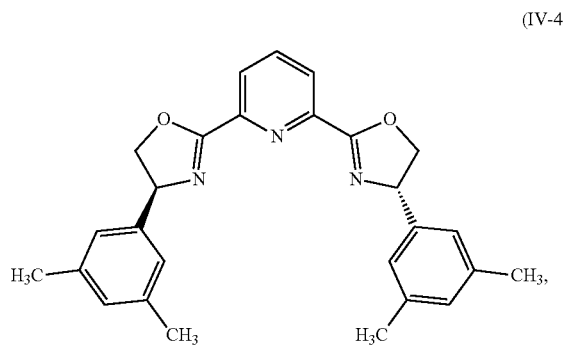 [SMILES: Cc1cc(C)cc([C@H]2COC(c3cccc(C4=N[C@@H](c5cc(C)cc(C)c5)CO4)n3)=N2)c1]

(IV-3)

a chiral ligand of the formula (IV-4), i.e. 2,6-bis((S)-4-(3,5-dimethylphenyl)-4,5-dihydrooxazol-2-yl)pyridine of the formula (IV-4)

(IV-4)

a chiral ligand of the formula (IV-5), i.e. 2,6-bis((S)-4-(3,5-dimethoxyphenyl)-4,5-dihydrooxazol2-yl)pyridine of the formula (IV-5)

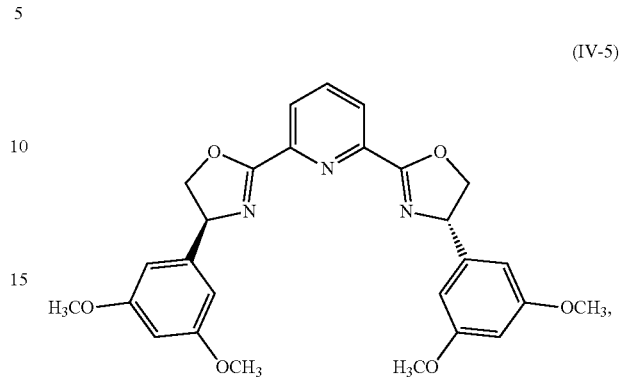

(IV-5)

a chiral ligand of the formula (IV-6), i.e. 2,6-bis((S)-4-mesityl-4,5-dihydrooxazol-2-yl)pyridine of the formula (IV-6)

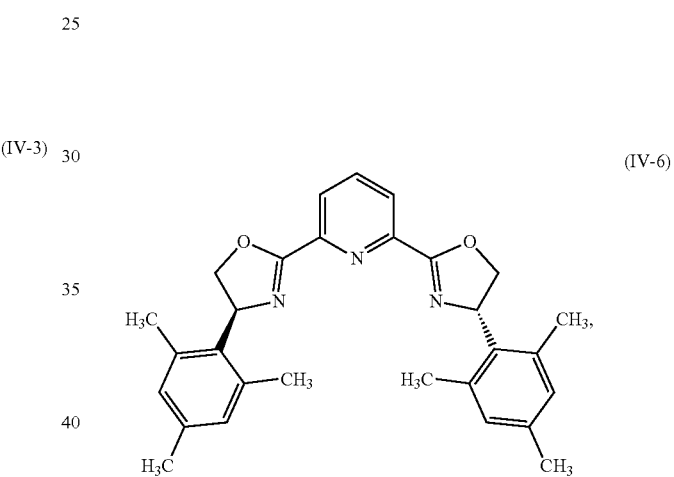

(IV-6)

a chiral ligand of the formula (IV-7), i.e. 2,6-bis((S)-4-(naphthalen-1-yl)-4,5-dihydrooxazol-2-yl)pyridine of the formula (IV-7)

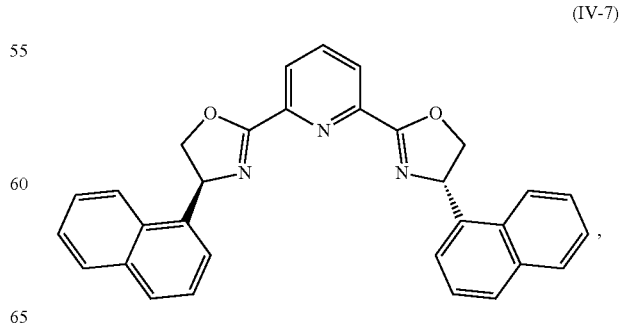

(IV-7)

a chiral ligand of the formula (IV-8), i.e. 2,6-bis((S)-4-(6-methoxynaphthalen-2-yl)-4,5-dihydrooxazol-2-yl)pyridine of the formula (IV-8)

(IV-8)

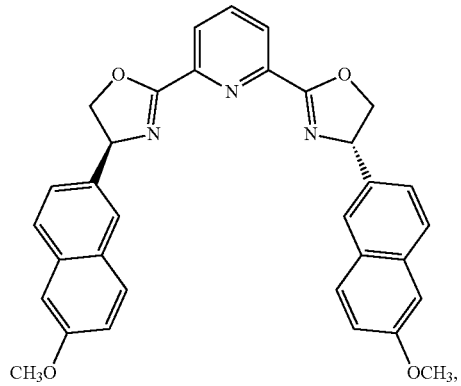

a chiral ligand of the formula (IV-9), i.e. ((4S,4'S,5S,5'S)-pyridine-2,6-diylbis(4,5-diphenyl-4,5-dihydro-1H-imidazole-2,1-diyl))bis(naphthalen-1-ylmethanone) of the formula (IV-9)

(IV-9)

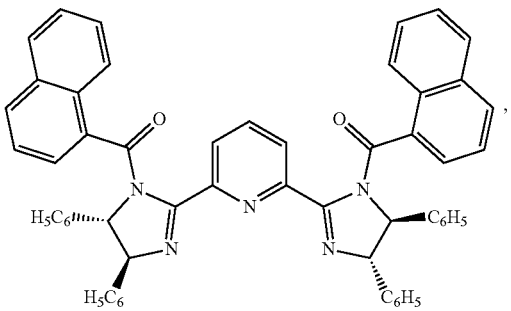

a chiral ligand of the formula (IV-10), i.e. 2,6-Bis((S)-4,5-dihydro-4-phenethyloxazol-2-yl)pyridine of the formula (IV-10)

(IV-10)

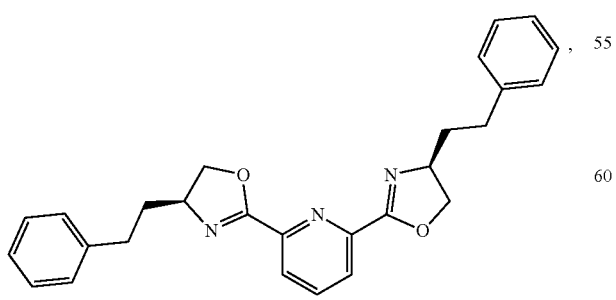

a chiral ligand of the formula (IV-11), i.e. (4R,5R)-2-[6-[(4S,5S)-4,5-diphenyl-4,5-dihydrooxazol2-yl]-2-pyridyl]-4,5-diphenyl-4,5-dihydrooxazole of the formula (IV-11)

(IV-11)

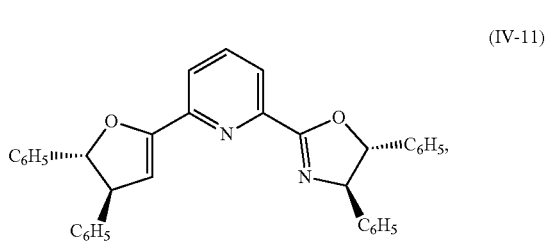

a chiral ligand of the formula (IV-12), i.e. ((4S,4'S,5S,5'S)-(4-chloropyridine-2,6-diyl)bis(4,5-diphenyl-4,5-dihydro-1H-imidazole-2,1-diyl))bis(naphthalen-1-ylmethanone) of the formula (IV-12)

(IV-12)

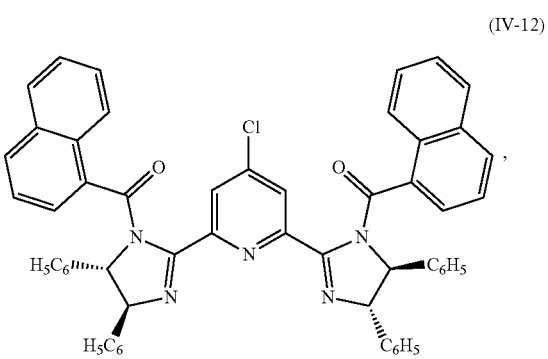

a chiral ligand of the formula (IV-13), i.e. (4S)-4-isopropyl-2-[6-[(4S)-4-isopropyl-4,5-dihydrooxazol-2-yl]-2-pyridyl]-4,5-dihydrooxazole of the formula (IV-13)

(IV-13)

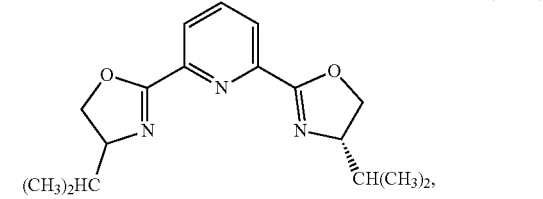

a chiral ligand of the formula (IV-14), i.e. (3aR,8bS)-2-[6-[(3aR,8bS)-4,8b-dihydro-3aH-indeno[1,2-d]oxazol-2-yl]-2-pyridyl]-4,8b-dihydro-3aH-indeno[1,2-d]oxazole of the formula (IV-14)

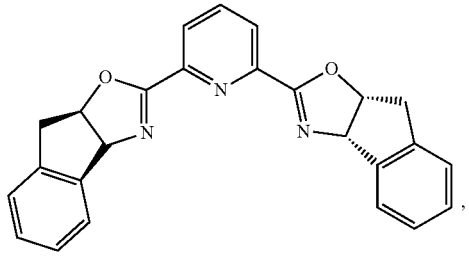

(IV-14)

and a chiral ligand of the formula (IV-15), i.e. (4S)-4-benzyl-2-[6-[(4S)-4-benzyl-4,5-dihydrooxazol-2-yl]-2-pyridyl]-4,5-dihydrooxazole of the formula (IV-15)

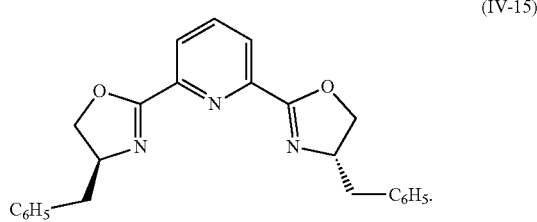

(IV-15)

In a particularly preferred embodiment, the chiral ligand of the formula (IV) is selected from 2,6-bis((S)-4-phenyl-4,5-dihydrooxazol-2-yl)pyridine of the formula (IV-1) and ((4S,4'S,5S,5'S)-pyridine-2,6-diylbis(4,5-diphenyl-4,5-dihydro-1H-imidazole-2,1-diyl))bis(naphthalen-1-ylmethanone) of the formula (IV-9). 2,6-bis((S)-4-phenyl-4,5-dihydrooxazol-2-yl)pyridine of the formula (IV-1) is most preferred.

In another particularly preferred embodiment, the chiral ligand of the formula (IV) is selected from 2,6-bis((R)-4-phenyl-4,5-dihydrooxazol-2-yl)pyridine of the formula (IV-1') and ((4R,4'R,5R,5'R)-pyridine-2,6-diylbis(4,5-diphenyl-4,5-dihydro-1H-imidazole-2,1-diyl))bis(naphthalen-1-ylmethanone) of the formula (IV-9'). 2,6-bis((R)-4-phenyl-4,5-dihydrooxazol-2-yl)pyridine of the formula (IV-1') is most preferred.

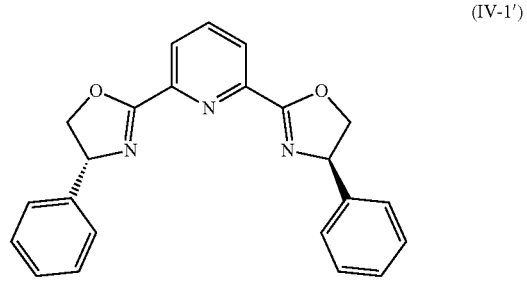

(IV-1')

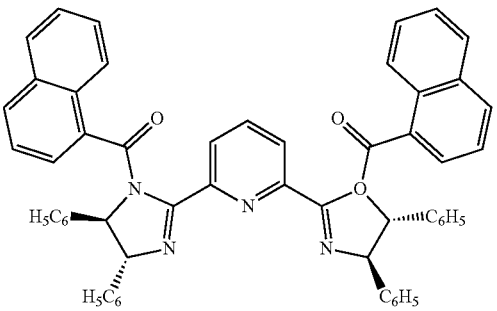

(IV-9')

The chiral ligands of formula (IV) used in the process of this invention are known generally from JP-A Hei 2-36181 or Desimoni et al (Chem. Rev., 2003, 103, 3119-3154), are commercially available and/or can be prepared in a known manner.

Further, 2,6-bis((S)-4-phenyl-4,5-dihydrooxazol-2-yl)pyridine of the formula (IV-1) is known from Schaus, S. E. et al. (Org Lett, 2000, 2, 1001-1004).

2,6-bis((S)-4-(4-bromophenyl)-4,5-dihydrooxazol-2-yl)pyridine of the formula (IV-2), 2,6-bis((S)-4-mesityl-4,5-dihydrooxazol-2-yl)pyridine of the formula (IV-6), 2,6-bis((S)-4-(6-methoxynaphthalen-2-yl)-4,5-dihydrooxazol-2-yl)pyridine of the formula (IV-8) were synthesized from dimethyl pyridine-2,6-bis(carbimidate) and (S)-2-amino-2-(4-bromophenyl)ethan-1-ol, (S)-2-amino-2-mesitylethan-1-ol or (S)-2-amino-2-(6-methoxynaphthalen-2-yl)ethan-1-ol, respectively, according to the general procedure described in Shemet, A. et al (Org. Lett, 2017, 19, 5527).

2,6-bis((S)-4-(4-methoxyphenyl)-4,5-dihydrooxazol-2-yl)pyridine of the formula (IV-3) and 2,6-bis((S)-4-(3,5-dimethoxyphenyl)-4,5-dihydrooxazol-2-yl)pyridine of the formula (IV-5) are both known from the aforementioned reference, i.e. Shemet, A. et al (Org. Lett, 2017, 19, 5527).

2,6-bis((S)-4-(3,5-dimethylphenyl)-4,5-dihydrooxazol-2-yl)pyridine of the formula (IV-4) is known from Lovinger, G. J. et al (J. Am. Chem. Soc., 2017, 139, 17293-17296).

2,6-bis((S)-4-(naphthalen-1-yl)-4,5-dihydrooxazol-2-yl)pyridine of the formula (IV-7) is known from Zhou, Z. et al (Tet. Lett. 2012, 53, 4518-4521)

((4S,4'S,5S,5'S)-pyridine-2,6-diylbis(4,5-diphenyl-4,5-dihydro-1H-imidazole-2,1-diyl))bis(naphthalen-1-ylmethanone) of the formula (IV-9) is known from Bhor, S. et al. (Org. Lett. 2005, 7 (16), 3393-3396).

2,6-Bis((S)-4,5-dihydro-4-phenethyloxazol-2-yl)pyridine of the formula (IV-10) is known from Lou, S et al (Org. Synth, 2010, 87, 310-316).

The chiral ligands of the formulae (IV-11), (IV-13), (IV-14) and (IV-15) are known from Tse, Man Kin; Bhor, Santosh; Klawonn, Markus; Anilkumar, Gopinathan; Jiao, Haijun; Doebler, Christian; Spannenberg, Anke; Maegerlein, Wolfgang; Hugl, Herbert; and Beller, Matthias (2006) Chemistry—A European Journal, 12(7), 1855-1874.

((4S,4'S,5S,5'S)-(4-chloropyridine-2,6-diyl)bis(4,5-diphenyl-4,5-dihydro-1H-imidazole-2,1-diyl))bis(naphthalen-1-ylmethanone) of the formula (IV-12) can be prepared by adapting the procedures of Bhor and coworkers (cf. Bhor, S. et al., Org. Lett. 2005, 7 (16), 3393-3396) as described in more detail in the Examples.

The molar ratio of the chiral ligand of the formula (IV) to the compound of the formula (II) can vary widely and depends on the reactants and reaction conditions used, but is generally from 1:5 to 1:10000, preferably 1:10 to 1:1000, more preferably from 1:10 to 1:200.

Preferably, the catalyst used in the process of this invention is obtained by reacting the metal salt of the formula $[M^{m+}]_n[A^{n-}]_m$ wherein $M^{m+}$ is a m-valent metal cation $M^{m+}$ wherein m is an integer of 1, 2 or 3 and the metal M has the same meaning as described hereinabove and $A^{n-}$ is a n-valent anion wherein n is an integer of 1, 2 or 3 with the chiral ligand of the formula (IV). The catalyst may be prepared by a method analogous to that described in US 2011/034718 for the synthesis of an asymmetric complex obtained by reacting an aluminum halide with an optically active pyridine compound (1). For example, the reaction of the metal salt of the formula $[M^{m+}]_n[A^{n-}]_m$ (V) with the chiral ligand of the formula (IV) is usually carried out in the presence of an organic solvent. Suitable organic solvents that may be used in the preparation of the catalyst are preferably the same as described hereinbelow for the reaction of the compound of formula (II) with the compound of formula (III) including, for example, halogenated aromatic hydrocarbons such as dichloromethane, 1,2-dichloromethane and chloroform, and aromatic hydrocarbon solvents such as benzene, toluene and xylene, and halogenated aromatic hydrocarbons such as chlorobenzene and dichlorobenzene. The reaction the metal salt of the formula $[M^{m+}]_n[A^{n-}]_m$ (V) with the chiral ligand (IV) is carried out preferably in the absence of water. In a preferred embodiment, the reaction is conducted under an atmosphere of an inert gas, preferably an inert gas selected from argon and nitrogen. Most preferably, the inert gas is nitrogen. The reaction temperature is usually in the range from −20° C. to 50° C. The reaction time is usually from 0.5 to 6 hours. Thus, a mixture comprising the catalyst is obtained, and the resultant mixture may be used directly in the reaction of the compound of formula (II) with the compound of formula (III), or the catalyst is first isolated from the mixture by means such as concentration. In a preferred embodiment, the resultant mixture comprising the catalyst is used directly for the reaction of the compound of formula (II) with the compound of formula (III).

The molar ratio of the catalyst to the compound of the formula (II) can vary widely and depends on the nature of the metal salt of the formula $[M^{m+}]_n[A^{n-}]_m$ (V) and of the chiral ligand (IV) used for its preparation and the reaction conditions employed, but is generally from 1:5 to 1:10000, preferably 1:10 to 1:1000 and more preferably from 1:10 to 1:200.

In a preferred embodiment, the process of this invention is carried out in substance.

In another preferred embodiment, the reaction of the compound of formula (II) with the compound of formula (III) is conducted in an organic solvent. In another preferred embodiment, the process of this invention is conducted in a substantially anhydrous (preferably anhydrous) organic solvent. The term "substantially anhydrous" as used herein means that, although anhydrous organic solvents are generally preferred in the reaction mixture, trace amounts of water, such as that often found in commercially available solvents, can be tolerated. Larger amounts of water should be avoided, since there would be an increased consumption of feedstocks.

The organic solvent used in the process of this invention can be selected from a variety of solvents depending upon the reactants and reaction conditions used.

In a preferred embodiment, the organic solvent is selected from hydrocarbons, ethers, nitriles, esters, ketones and any combination thereof.

The term "hydrocarbons" includes aliphatic hydrocarbons, cycloaliphatic hydrocarbons, aromatic hydrocarbons, halogenated aliphatic hydrocarbons, halogenated aromatic hydrocarbons and any combination thereof.

Aliphatic hydrocarbons include straight and branched chain aliphatic hydrocarbons.

Straight chain aliphatic hydrocarbons that can be used in the present invention are those having from 5 to 15 carbon atoms, preferably 5 to 10 carbon atoms. Examples of straight chain aliphatic hydrocarbons include n-pentane, n-hexane, n-heptane, n-octane, n-nonane, n-decane or any combination thereof, preferably n-heptane.

The branched chain aliphatic hydrocarbons which are suitable for use in the present invention are those having from 4 to 15 carbon atoms, preferably 5 to 12 carbon atoms, more preferably 7 to 12 carbon atoms and even more preferably 8 to 11 carbon atoms. Examples of suitable branched chain aliphatic hydrocarbons include 2,3-dimethylbutane, 2-methylpentane, 3-methylpentane, 2,2-dimethylpentane, 2,3-dimethylpentane, 2,4-dimethylpentane, 2,2,4-trimethylpentane, 2-methylhexane, 3-methylhexane, 2,4-dimethylhexane, 2,5-dimethylhexane, 2,2,4-trimethylhexane, 2,3,4-trimethylhexane, 3,3,4-trimethylhexane, 2-methylheptane, 3-methylheptane, 2,3-dimethylheptane, 3,4-dimethylpentane, 2-ethyloctane, 2,3-dimethyloctane, 2-methylnonane, 3,4-dimethylnonane, 3-methyldecane, 2-methylundecane, 2-methyldodecane, 2,2,4 trimethyldodecane and any combination thereof.

Examples of suitable cycloaliphatic hydrocarbons include saturated or unsaturated cycloaliphatic hydrocarbons, such as e.g. cyclopentane, cyclohexane, cyclohexene, cycloheptane, cyclooctane, cyclooctene, 1,5-cyclooctadiene and the like. Preference is given to saturated cycloaliphatic hydrocarbons having from 5 to 10 carbon atoms. Cyclohexane is particularly preferred.

Examples of suitable aromatic hydrocarbons include benzene, toluene, o-xylene, m-xylene, p-xylene, ethylbenzene, 2-propylbenzene (cumene), 2-isopropyltoluene (o-cymene), 3-isopropyltoluene (m-cymene), 4-isopropyltoluene (p-cymene), 1,3,5-trimethylbenzene (mesitylene) and the like. Preference is given to toluene, o-xylene, m-xylene, p-xylene, ethylbenzene, 1,3,5-trimethylbenzene (mesitylene) and any combination thereof. Especially preferred among the aromatic hydrocarbons are toluene, o-xylene, m-xylene, p-xylene, 1,3,5-trimethylbenzene (mesitylene) and any combination thereof, with toluene being the most preferred.

Examples of suitable halogenated aliphatic hydrocarbons include dichloromethane (methylene chloride), chloroform, carbon tetrachloride, 1,2-dichloroethane, 1,1,1,2-tetrachloroethane, 1,1-dichloroethylene, 1,2-dichloroethylene, trichloroethylene, and the like. Preference is given to dichloromethane.

Examples of suitable halogenated aromatic hydrocarbons include chlorobenzene, bromobenzene, o-dichlorobenzene, m-dichlorobenzene, α,α,α-trifluorotoluene (benzotrifluoride) and the like. Preference is given to chlorobenzene.

Examples of suitable ethers include acyclic, cyclic or aromatic ethers such as diethyl ether, diisopropyl ether, n-butyl methyl ether, isobutyl methyl ether, sec-butyl methyl ether, tert-butyl methyl ether, cyclopentyl methyl ether, tetrahydrofuran, 2-methyltetrahydrofuran, 2,5-dimethyltetrahydrofuran, 1,4-dioxane, anisole and the like.

Examples of suitable nitriles include acetonitrile, benzonitrile, and the like.

Examples of suitable esters include ethyl acetate, n-propylacetate, isopropyl acetate, n-butyl acetate, and the like.

Examples of suitable ketones include acetone, methyl ethyl ketone, methyl isopropyl ketone, methyl isobutyl ketone, cyclopropyl methyl ketone and the like.

In a preferred embodiment, the organic solvent is selected from aliphatic hydrocarbons, cycloaliphatic hydrocarbons, aromatic hydrocarbons, halogenated aliphatic hydrocarbons, halogenated aromatic hydrocarbons, ethers, nitriles, esters, ketones and any combination thereof.

In another preferred embodiment, the organic solvent is selected from aliphatic hydrocarbons, cycloaliphatic hydrocarbons, aromatic hydrocarbons, halogenated aliphatic hydrocarbons, halogenated aromatic hydrocarbons, acyclic ethers, cyclic ethers, aromatic ethers, nitriles, esters, ketones and any combination thereof.

In yet another preferred embodiment, the organic solvent is selected from aromatic hydrocarbons, halogenated aliphatic hydrocarbons, halogenated aromatic hydrocarbons, acyclic ethers, cyclic ethers, aromatic ethers, nitriles, esters, ketones and any combination thereof.

In still another preferred embodiment, the organic solvent is selected from hydrocarbons. The hydrocarbon may in principle be selected from aliphatic hydrocarbons, cycloaliphatic hydrocarbons, aromatic hydrocarbons, halogenated aliphatic hydrocarbons and halogenated aromatic hydrocarbons. More preferably, the organic solvent is a hydrocarbon selected from aromatic hydrocarbons, halogenated aliphatic hydrocarbons, halogenated aromatic hydrocarbons and any combination thereof. Even more preferably, the organic solvent is a hydrocarbon selected from halogenated aliphatic hydrocarbons, halogenated aromatic hydrocarbons and any combination thereof. In a particularly preferred embodiment, the organic solvent is a hydrocarbon selected from aromatic hydrocarbons, halogenated aromatic hydrocarbons and any combination thereof. In another particularly preferred embodiment, the organic solvent is a hydrocarbon selected from halogenated aromatic hydrocarbons. In another particularly preferred embodiment, the organic solvent is a hydrocarbon selected from halogenated aliphatic hydrocarbons.

In another especially preferred embodiment, the organic solvent is a hydrocarbon selected from n-heptane, benzene, toluene, o-xylene, m-xylene, p-xylene, ethylbenzene, 1,3,5-trimethylbenzene (mesitylene), dichloromethane, chlorobenzene and any combination thereof.

In yet another especially preferred embodiment, the organic solvent is a hydrocarbon selected from n-heptane, benzene, toluene, o-xylene, m-xylene, p-xylene, ethylbenzene, 1,3,5-trimethylbenzene (mesitylene) and any combination thereof.

In yet another especially preferred embodiment, the organic solvent is a hydrocarbon selected from toluene, o-xylene, m-xylene, p-xylene, ethylbenzene and 1,3,5-trimethylbenzene (mesitylene).

In yet another especially preferred embodiment, the organic solvent is a hydrocarbon selected from dichloromethane, chlorobenzene and a combination thereof.

In yet another especially preferred embodiment, the organic solvent is chlorobenzene.

In yet another especially preferred embodiment, the organic solvent is dichloromethane.

The molar ratio of the organic solvent to the compound of the formula (II) can vary widely and depends on the reactants and reaction conditions used, but is generally from 0.01:1 to 100:1, preferably 0.01:1 to 40:1, more preferably from 0.01:1 to 10:1, even more preferably from 0.01:1 to 2:1 and still more preferably from 0.01:1 to 0.5:1. In another preferred embodiment, the organic solvent is used in an amount sufficient to dissolve the other reagents.

It is preferable to conduct the reaction of the compound of formula (II) with the compound of formula (III) under an atmosphere of an inert gas. Preferably, the inert gas is selected from argon and nitrogen. Most preferably, the inert gas is nitrogen.

In another preferred embodiment, the reaction of the compound of formula (II) with the compound of formula (III) is conducted in the presence of an activated molecular sieve, more preferably an activated molecular sieve having a pore size of from 3 to 5 angstrom (A). For example, an activated 3 Å, 4 Å or 5 Å molecular sieve may be used, with an activated 3 Å molecular sieve being preferred. The 3 Å, 4 Å or 5 Å molecular sieve are either beaded or powdered. Suitable materials for the activated molecular sieve include, for example, metal aluminosilicates such as mixed sodium-potassium aluminosilicates. Such molecular sieves are commercially available.

The process of this invention can be carried out under atmospheric pressure or under slightly elevated or reduced pressure. Typically, the atmospheric pressure is employed. In another embodiment, the process of this invention is conducted under elevated pressure, preferably in a range from 1 to 5 bar and more preferably 1 to 2 bar.

The temperature used in the process of this invention can vary widely and depends on a variety of factors such as, for example, the organic solvent used. Under atmospheric pressure (1 bar), the process of this invention is generally conducted at a temperature in the range from −40° C. to 120° C., preferably from −20° C. to 80° C., more preferably from −20° C. to 50° C. and even more preferably from 0° C. to 50° C.

The reaction time can vary in a wide range and depends on a variety of factors such as, for example, temperature, pressure, or the reagents and auxiliary substances used. Typical reaction times are in the range of from 3 to 72 hours, preferably from 6 to 48 hours and more preferably from 4 to 12 hours.

The non-racemic cyclohexene compound of formula of the formula (I) can be isolated from the final reaction mixture by employing conventional methods, for example by extraction, in particular extraction with a basic or neutral aqueous medium, distillation, column chromatography (i.e. silica gel, alumina), preparatory HPLC (high performance liquid chromatography), preparatory SFC (supercritical fluid chromatography), recrystallization and the like.

In a preferred embodiment, the non-racemic cyclohexene compound of formula (I) is further converted to a non-racemic cyclohexenol compound of formula (VI)

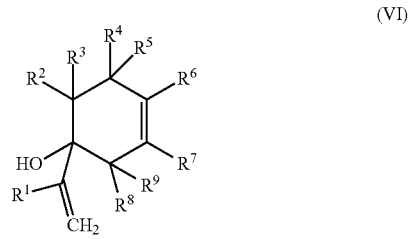

(VI)

wherein $R^1$, $R^2$, $R^3$, $R^4$, $R^5$, $R^6$, $R^7$, $R^8$ and $R^9$ have the same meaning as in formula (I).

For example, the conversion of the non-racemic cyclohexene compound of formula (I) to the non-racemic cyclohexenol compound of formula (VI) can be performed according to methods known in the art, for example by cleavage of the ester group Y=OC(O)R$_A$ to a hydroxyl group —OH followed by a Wittig or other type of olefination reaction to convert the ketone group into an alkene group. The ester cleavage and the Wittig reaction can be carried out according to methods known to one skilled in the art, e.g. in analogy to the methods described in Andrade et al. (Synthetic Communications, 1992, 22, 1603-1609). Preferably, the Wittig reaction is accomplished by employing methyltriphenylphosphonium bromide, a strong base like n-butyllithium and an organic solvent like tetrahydrofuran. The cleavage of the ester group Y=OC(O)R$_A$ to a hydroxyl group —OH can be performed by using a base (e.g. sodium hydroxide, potassium hydroxide, sodium carbonate, potassium carbonate, sodium methoxide, or potassium methoxide) and an organic solvent like methanol or ethanol, optionally including water as a co-solvent. In another embodiment, the ester cleavage is performed after completion of the Wittig or other olefination reaction, for example during work-up of the reaction mixture obtained from the Wittig reaction (e.g. by adding the base to said reaction mixture). Examples of ester cleavage reactions include transesterification, saponification, and hydrolysis. Olefination reactions include any reaction in which a C=O double bond is replaced with a C=CH$_2$ double bond.

In an especially preferred embodiment, there is provided a process for the synthesis of a non-racemic cyclohexenol compound of formula (VI)

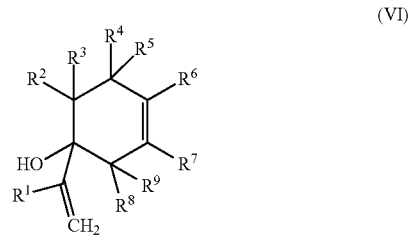

(VI)

wherein $R^1$, $R^2$, $R^3$, $R^4$, $R^5$, $R^6$, $R^7$, $R^8$ and $R^9$ have the same meaning as in formula (I) comprising the steps of:
(i) preparing a non-racemic cyclohexene compound of formula (I) as described herein,
(ii) subjecting the non-racemic cyclohexene compound of formula (I) to ester cleavage to give the non-racemic cyclohexenol compound of formula (VII)

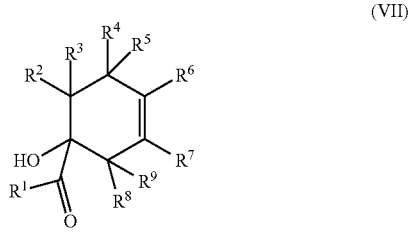

(VII)

wherein $R^1$, $R^2$, $R^3$, $R^4$, $R^5$, $R^6$, $R^7$, $R^8$ and $R^9$ have the same meaning as in formula (I), and
(iii) subjecting the non-racemic cyclohexenol compound of formula (VII) to a Wittig reaction to give the non-racemic cyclohexenol compound of formula (VI).

In another especially preferred embodiment, there is provided a process for the synthesis of a non-racemic cyclohexenol compound of formula (VI)

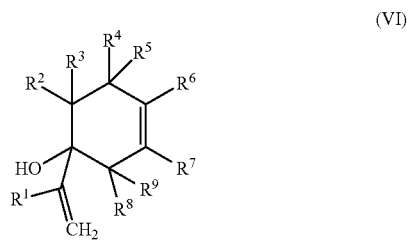

(VI)

wherein $R^1$, $R^2$, $R^3$, $R^4$, $R^5$, $R^6$, $R^7$, $R^8$ and $R^9$ have the same meaning as in formula (I) comprising the steps of:
(i) preparing a non-racemic cyclohexene compound of formula (I) as described herein,
(ii) subjecting the non-racemic cyclohexene compound of formula (I) to a Wittig reaction to give non-racemic cyclohexene compound of formula (VIII)

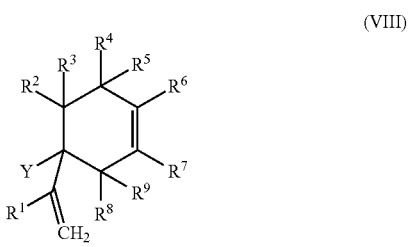

(VIII)

wherein $R^1$, $R^2$, $R^3$, $R^4$, $R^5$, $R^6$, $R^7$, $R^8$, $R^9$ and Y have the same meaning as in formula (I), and
(iii) subjecting the non-racemic cyclohexene compound of formula (VIII) to ester cleavage to give the non-racemic cyclohexenol compound of formula (VI).

A particularly preferred embodiment relates to a process for the synthesis of a non-racemic cyclohexenol compound of formula (VI)
wherein
$R^1$ and $R^6$ are both methyl; and
$R^2$, $R^3$, $R^4$, $R^5$, $R^7$, $R^8$ and $R^9$ are each hydrogen.

Such a compound corresponds to non-racemic limonene-4-ol of the formula (VI-1)

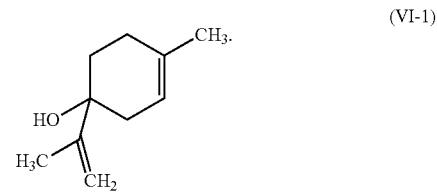

(VI-1)

In an especially preferred embodiment, the non-racemic cyclohexenol compound of formula (VI) is (R)-limonene-4-ol of the formula ((R)-VI-1)

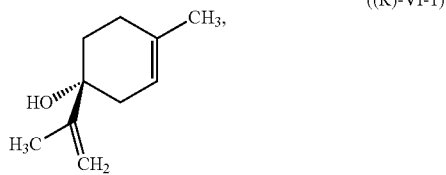

or, in another especially preferred embodiment, (S)-limonene-4-ol of the formula ((S)-VI-1)

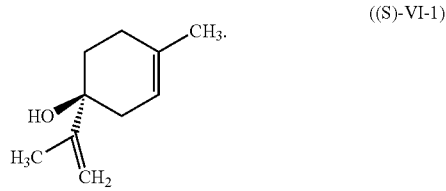

Non-racemic cyclohexene compounds of formula (I) particularly useful as starting material in step (i) of the process for the synthesis of non-racemic limonene-4-ol of the formula (VI-1) are those wherein $R^1$ and $R^6$ are both methyl;

$R^2$, $R^3$, $R^4$, $R^5$, $R^7$, $R^8$ and $R^9$ are each hydrogen;

Y is $OC(O)R_A$ wherein $R_A$ is phenyl or diphenylmethyl.

Such compounds correspond to 1-acetyl-4-methylcyclohex-3-en-1-yl benzoate of the formula (I-1) and 1-acetyl-4-methylcyclohex-3-en-1-yl 2,2-diphenylacetate of the formula (I-2) as described herein above.

Compounds of formulae ((R)-I-1), ((R)-I-2), ((R)-I-3), ((R)-I-4), and ((R)-I-5), in particular (R)-1-acetyl-4-methylcyclohex-3-en-1-yl benzoate of the formula ((R)-I-1) and (R)-1-acetyl-4-methylcyclohex-3-en-1-yl 2,2-diphenylacetate of the formula ((R)-I-2), are useful as starting materials in step (i) of the process for the synthesis of (R)-limonene-4-ol of formula ((R)-VI-1).

Thus, another embodiment of this invention is directed to the use of any of the compounds of formulae ((R)-I-1), ((R)-I-2), ((R)-I-3), ((R)-I-4), and ((R)-I-5), in particular (R)-1-acetyl-4-methylcyclohex-3-en-1-yl benzoate of the formula ((R)-I-1) and (R)-1-acetyl-4-methylcyclohex-3-en-1-yl 2,2-diphenylacetate of the formula ((R)-I-2), as a starting material for the synthesis of (R)-limonene-4-ol of formula ((R)-VI-1).

Compounds of formulae ((S)-I-1), ((S)-I-2), ((S)-I-3), ((S)-I-4), and ((S)-I-5), in particular (S)-1-acetyl-4-methylcyclohex-3-en-1-yl benzoate of the formula ((S)-I-1) and (S)-1-acetyl-4-methylcyclohex-3-en-1-yl 2,2-diphenylacetate of the formula ((S)-I-2), are useful as starting materials in step (i) of the process for the synthesis of (S)-limonene-4-ol of formula ((S)-VI-1).

Yet another embodiment of this invention is directed to the use of any of the compounds of formulae ((S)-I-1), ((S)-I-2), ((S)-I-3), ((S)-I-4), and ((S)-I-5), in particular (S)-1-acetyl-4-methylcyclohex-3-en-1-yl benzoate of the formula ((S)-I-1) and (S)-1-acetyl-4-methylcyclohex-3-en-1-yl 2,2-diphenylacetate of the formula ((S)-I-2), as a starting material for the synthesis of (S)-limonene-4-ol of formula ((S)-VI-1).

The invention is illustrated by the following examples without being limited thereto or thereby.

EXAMPLES

Chemical terms and the definitions below have their usual meanings unless indicated otherwise. For example, "Yb (OTf$_3$" refers to Ytterbium(III) triflate; "Y(OTf)$_3$" refers to Yttrium(III) triflate; "Sc(OTf)$_2$" refers to Scandium(II) triflate; "La(OTf)$_3$" refers to Lanthanum(II) triflate; "Ce (OTf)$_3$" refers to Cerium(III) triflate; "Pr(OTf)$_3$" refers to Praseodymium(II) triflate; "Nd(OTf)$_3$" refers to Neodymium(II) triflate; "Sm(OTf)$_3$" refers to Samarium(III) triflate; "Eu(OTf)$_3$" refers to Europium(III) triflate; "Gd(OTf)$_3$" refers to Gadolinium(II) triflate; "Tb(OTf)$_3$" refers to Terbium(III) triflate; "Dy(OTf)$_3$" refers to Dysprosium(III) triflate; "Ho(OTf)$_3$" refers to Holmium(III) triflate; "Er (OTf)$_3$" refers to Erbium(III) triflate; "Tm(OTf)$_3$" refers to Thulium(II) triflate; "Lu(OTf$_3$" refers to Lutetium(III) triflate; "H$_2$O" refers to water; "THF" refers to tetrahydrofurane; "MeCN" refers to acetonitrile; "Et$_2$O" refers to diethyl ether; "EtOAc" refers to ethyl acetate; "MeOH" refers to methanol; "iPrOH" or "IPA" both refer to isopropanol; "CH$_2$Cl$_2$" or "DCM" both refer to dichloromethane; "PhH" refers to benzene; "PhMe" refers to toluene; "PhCl" refers to chlorobenzene; "DCE" refers to 1,2-dichloroethane; "Et$_3$N" or "NEt$_3$" both refer to triethylamine; "i-Pr$_2$NH" refers to diisopropylamine, "DIPEA" refers to N,N-diisopropylethylamine; "Pyr" refers to pyridine; "Ph" refers to phenyl; "CH(Ph)$_2$" refers to diphenylmethyl; "Me" refers to methyl; "Et" refers to ethyl; "Ad" refers to 1-adamantyl; "Bz" refers to benzoyl; "BzCl" refers to benzoyl chloride; "Ph$_2$CHCO$_2$Cl" refers to diphenylacetyl chloride; "1-Nap" refers to "1-naphthyl"; "2-Nap" refers to "2-naphthyl"; "NaB$_{Ar}$F" refers to sodium tetrakis[3,5-bis(trifluoromethyl)phenyl]borate; "N(n-Bu)$_4$Br" refers to tetra-n-butylammonium bromide; "$^t$Bu" refers to "tert-butyl"; "o-Br-Ph" refers to "2-bromophenyl"; "p-$^t$Bu-Ph" refers to "4-tert-butylphenyl"; "p-NO$_2$-Ph" refers to "4-nitrophenyl"; "MS" refers to molecular sieve; "3 Å MS" refers to 3 Å molecular sieve; "equiv." refers to equivalent; "mmol" refers to millimole or millimoles; "g" refers to gram or grams; "mg" refers to milligram or milligrams; "min" refers to minutes; "h" refers to hours; "l" or "L" refers to liters; "ml" or "mL" refers to milliliter or milliliters; "dr" refers to diasterometric ratio; "ee" refers to enantiomeric excess; "rr" refers to regiomeric ratio; "$^1$H-NMR" refers to proton Nuclear Magnetic resonance; "$^{13}$C-NMR" refers to carbon-13 Nuclear Magnetic resonance; "SFC" refers to supercritical fluid chromatography, "HPLC" refers to high performance liquid chromatography; "HRMS" refers to high resolution mass spectrometry; and "TCL" refers to thin layer chromatography.

Materials and Methods:

Unless otherwise stated, reactions were performed with freshly dried solvents utilizing standard Schlenk techniques. Glassware was oven-dried at 120° C. for a minimum of four hours or flamedried utilizing a Bunsen burner under high vacuum. THF, DCM, MeCN, PhH, and PhMe were dried by passing through activated alumina columns. Pyridinebisimidazoline (PyBim) ligands were synthesized using the procedure reported by Bhor and coworkers (cf. Bhor, S. et al., Org. Lett. 2005, 7 (16), 3393-3396). MeOH (HPLC grade) was purchased from Fisher Scientific. 1,4-dioxane, anhydrous ≥99.9%, was purchased from Millipore Sigma. DCE, Et$_3$N, i-Pr$_2$NH, DIPEA, Pyr, and 2,6-lutidine were distilled from calcium hydride prior to use and stored under N$_2$ or Ar. Commercial reagents were used directly as supplied from commercial sources and without further purification unless otherwise specified. All reactions were monitored by thin layer chromatography using EMD/Merck silica gel 60 F254 pre-coated plates (0.25 mm) and were visualized by UV (254 nm) and $KMnO_4$, p-anisaldehyde, iodine, or CAM staining. Flash column chromatography was performed as described by Still and coauthors (cf. Still, W. C. et al. J. Org. Chem. 1978, 43 (14), 2923-2925) using silica gel (Silia-Flash® P60, particle size 40-63 microns [230 to 400 mesh]) purchased from Silicycle. $^1H$ and $^{13}C$ NMR spectra were recorded on a Bruker Advance III HD with Prodigy Cryoprobe (at 400 MHz and 101 MHz, respectively) or Varian Inova 500 (at 500 MHz and 126 MHz, respectively) and are reported relative to internal $CDCl_3$ ($^1H$, δ=7.26), $CDCl_3$ ($^{13}C$, δ=77.16). Data for $^1H$ NMR spectra are reported as follows: chemical shift (5 ppm) (multiplicity, coupling constant (Hz), integration). Multiplicity and qualifier abbreviations are as follows: s=singlet, d=doublet, t=triplet, q=quartet, p=pentet, hept=heptet, m=multiplet. IR spectra were recorded on a Perkin Elmer Paragon 1000 spectrometer and are reported in frequency of absorption ($cm^{-1}$). Analytical chiral SFC was performed with a Mettler SFC supercritical $CO_2$ analytical chromatography system ($CO_2$=1450 psi, column temperature=40° C.) with a Chiralcel OD-H column (4.6 mm×25 cm). Preparative and analytical chiral HPLC was performed with an S3 Agilent 1100 Series HPLC with a Chiralpak IH column (4.6 mm×25 cm, Daicel Chemical Industries, Ltd.). HRMS were acquired using an Agilent 6200 Series TOF with an Agilent G1978A Multimode source in electrospray ionization (ESI) mode. Molecular formulas of the compounds [M] are given, with the observed ion fragment in brackets, e.g. [M+H]+. Benzoyl chloride, diphenylacetyl chloride, Ytterbium(III) triflate, 2,6-bis[(4S)-4-phenyl-2-oxazolinyl]pyridine of the formula (IV-1), and 2,6-Bis((S)-4,5-dihydro-4-phenethyl-oxazol-2-yl)pyridine of the formula (IV-10) were purchased from Sigma-Aldrich and used as received. Isoprene was purchased from Sigma-Aldrich and distilled prior to use. Diacetyl was purchased from TCI America and used as received. Yttrium(III) triflate, lanthanum(II) triflate, cerium (II) triflate, prasaeodymium(III) triflate, neodymium(III) triflate, europium(III) triflate, gadolinium(III) triflate, terbium (III) triflate, dysprosium(III) triflate, holmium(III) triflate, erbium(III) triflate, and lutetium(III) triflate were purchased from Strem Chemicals, Inc. and used as received. Scandium (II) triflate, samarium(II) triflate, and ytterbium(III) triflate were purchased from Sigma-Aldrich and used as received. Triethylamine was distilled over calcium hydride prior to use. Dichloromethane, toluene, tetrahydrofuran, methyl-tert-butyl ether, and diethyl ether were purchased from Fisher Scientific and dried by passing over an activated alumina column. 1,2-dichloroethane, tetrachloromethane, trichloroethylene, acetonitrile, 1,4-dioxane, 2,5-dimethyl tetrahydrofuran (mixture of cis and trans), cyclopentylmethyl ether, and diisopropyl ether were purchased from Sigma-Aldrich. Deuteriochloroform was purchased from Cambridge Isotope Laboratories. The 3 Å molecular sieve was purchased from Sigma-Aldrich and activated by heating under a flame at reduced pressure (100 mTorr) for 20 minutes prior to use.

Preparation of the Compounds of Formula (II)

General Procedure A for compounds of formula II (see also Scheme A below): To a dry roundbottomed flask, equipped with a magnetic stir bar was charged diacetyl (IX) (1.0 equiv.), triethylamine (1.2 equiv.) and dry dichloromethane. To this solution was added electrophile (1.0 equiv.) at 0° C. under $N_2$. The reaction was allowed to slowly warmed to 23° C. and monitored by TLC. Upon completion, hexanes (35 mL) was added, and the reaction mixture was filtered through a plug of sand. The resulting solution was concentrated under reduced pressure, and the residue was subjected to silica gel chromatography.

Scheme A

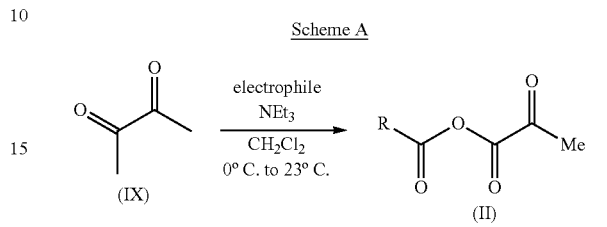

Preparation of 3-oxobut-1-en-2-yl benzoate of the formula (II-1)

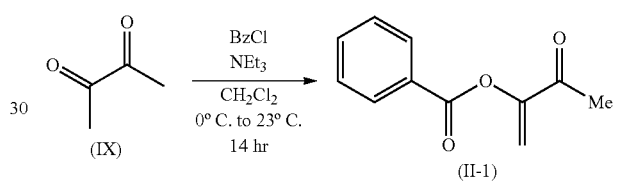

3-oxobut-1-en-2-yl benzoate of the formula (II-1) was prepared from diacetyl (IX) (2.62 mL, 30.0 mmol, 1.0 equiv.), triethylamine (5.02 mL, 36.0 mmol, 1.2 equiv.), benzoyl chloride (3.48 mL, 30.0 mmol, 1.0 equiv), and dry dichloromethane (35 mL) following General Procedure A. The resulting solution was concentrated under reduced pressure, and the residue was subjected to silica gel chromatography (1:20 EtOAc:hexanes→1:10 EtOAc:hexanes) to afford 3-oxobut-1-en-2-yl benzoate of the formula (II-1) (2.38 g, 12.5 mmol, 42%) as a yellow oil which solidifies upon storage at −20° C. Spectroscopic data matched previously reported values (cf. Tamariz, J.; Vogel, P. Helv. Chim. Acta 1981, 64 (1), 188-197).

$^1H$ NMR (500 MHz, $CDCl_3$) δ 8.12 (dt, J=7.0, 1.4 Hz, 2H), 7.74-7.56 (m, 1H), 7.56-7.40 (m, 2H), 6.04 (d, J=2.4 Hz, 1H), 5.74 (d, J=2.4 Hz, 1H), 2.42 (s, 3H).

Preparation of 3-oxobut-1-en-2-yl 2,2-diphenylacetate of the formula (II-2)

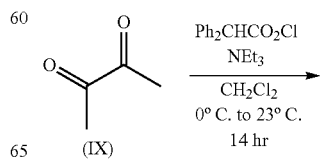

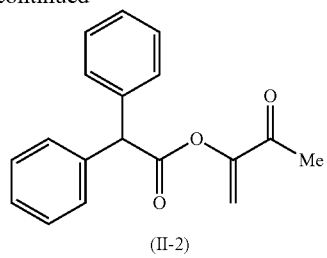

(II-2)

3-oxobut-1-en-2-yl 2,2-diphenylacetate of the formula (II-2) was prepared from diacetyl (IX) (2.19 mL, 25.0 mmol, 1.0 equiv.), triethylamine (4.18 mL, 30.0 mmol, 1.2 equiv.), diphenylacetyl chloride (2.90 mL, 25.0 mmol, 1.0 equiv), and dry dichloromethane (35 mL) following General Procedure A. The resulting solution was concentrated under reduced pressure, and the residue was subjected to silica gel chromatography (1:20 EtOAc:hexanes→1:10 EtOAc:hexanes) to afford 3-oxobut-1-en-2-yl 2,2-diphenylacetate of the formula (II-2) (3.1 g, 12.7 mmol, 74%) as a white solid. Spectroscopic data matched previously reported values (cf. Dominguez, D.; Cava, M. P. Tetrahedron Lett. 1982, 23 (52), 5513-5516)

$^1$H NMR (400 MHz, CDCl$_3$) δ 7.25-7.50 (m, 10H), 5.93 (d, J=2.5 Hz, 1H), 5.57 (d, J=2.5 Hz, 1H), 5.22 (s, 2H), 2.28 (s, 6H).

$^{13}$C NMR (101 MHz, CDCl$_3$) δ 191.54, 170.58, 151.67, 137.88, 128.78, 128.70, 127.53, 113.93, 56.60, 25.48.

Preparation of 3-oxobut-1-en-2-yl (3r,5r,7r)-adamantane-1-carboxylate of the formula (II-3)

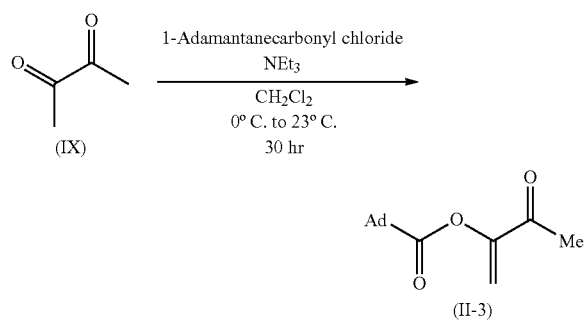

(IX) → (II-3)

3-oxobut-1-en-2-yl (3r,5r,7r)-adamantane-1-carboxylate of the formula (II-3) was prepared from diacetyl (IX) (1.32 mL, 15.0 mmol, 1.0 equiv.), triethylamine (2.51 mL, 18.0 mmol, 1.2 equiv.), 1-adamantanecarbonyl chloride (2.98 g, 15 mmol, 1.0 equiv), and dry dichloromethane (20 mL) following General Procedure A with 30 h at 23° C. The resulting solution was concentrated under reduced pressure, and the residue was subjected to silica gel chromatography (1:20 EtOAc:hexanes→1:10 EtOAc:hexanes) to afford 3-oxobut-1-en-2-yl (3r,5r,7r)-adamantane-1-carboxylate of the formula (II-3) (816 mg, 3.29 mmol, 22%).

$^1$H NMR (500 MHz, CDCl$_3$) δ 5.90 (d, J=2.2 Hz, 1H), 5.54 (d, J=2.2 Hz, 1H), 2.34 (s, 3H), 2.06 (q, J=3.0 Hz, 3H), 2.01 (d, J=2.9 Hz, 6H), 1.75 (dt, J=4.5, 2.9 Hz, 6H).

Preparation of 3-oxobut-1-en-2-yl 1-naphthoate of the formula (II-4)

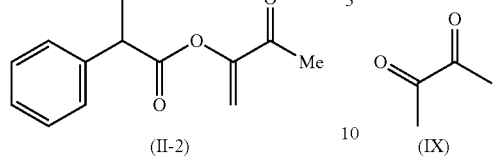

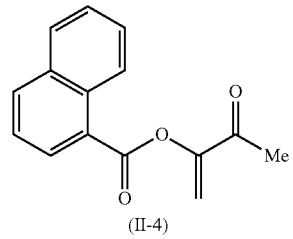

(II-4)

3-oxobut-1-en-2-yl 1-naphthoate of the formula (II-4) was prepared from diacetyl (IX) (1.32 mL, 15.0 mmol, 1.0 equiv.), triethylamine (2.51 mL, 18.0 mmol, 1.2 equiv.), 1-napthoyl chloride (2.26 mL, 15.0 mmol, 1.0 equiv), and dry dichloromethane (18 mL) following General Procedure A. The resulting solution was concentrated under reduced pressure, and the residue was subjected to silica gel chromatography (1:20 EtOAc:hexanes→1:10 EtOAc:hexanes) to afford 3-oxobut-1-en2-yl 1-naphthoate of the formula (II-4) (1.54 g, 6.4 mmol, 43%). Spectroscopic data matched previously reported values (cf. Tamariz, J.; Vogel, P. Helv. Chim. Acta 1981, 64 (1), 188-197).

$^1$H NMR (500 MHz, CDCl$_3$) δ 8.94 (dq, J=8.7, 0.8 Hz, 1H), 8.39 (dd, J=7.3, 1.3 Hz, 1H), 8.09 (ddt, J=8.2, 1.3, 0.6 Hz, 1H), 7.91 (ddt, J=8.2, 1.3, 0.6 Hz, 1H), 7.64 (ddd, J=8.6, 6.8, 1.4 Hz, 1H), 7.60-7.51 (m, 2H), 6.09 (d, J=2.4 Hz, 1H), 5.81 (d, J=2.4 Hz, 1H), 2.47 (s, 3H).

Preparation of 3-oxobut-1-en-2-yl 2-naphthoate of the formula (II-5)

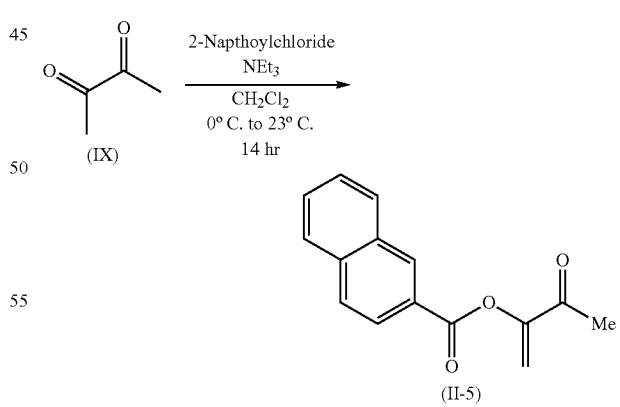

(II-5)

3-oxobut-1-en-2-yl 2-naphthoate of the formula (II-5) was prepared from diacetyl (IX) (1.32 mL, 15.0 mmol, 1.0 equiv.), triethylamine (2.51 mL, 18.0 mmol, 1.2 equiv.), 2-napthoyl chloride (2.26 mL, 15.0 mmol, 1.0 equiv), and dry dichloromethane (18 mL) following General Procedure A. The resulting solution was concentrated under reduced pressure, and the residue was subjected to silica gel chromatography (1:20 EtOAc:hexanes→1:10 EtOAc:hexanes) to afford 3-oxobut-1-en-2-yl 2-naphthoate of the formula (II-5) (1.54 g, 6.4 mmol, 43%). Spectroscopic data matched previously reported values (cf. Tamariz, J.; Vogel, P. *Helv. Chim. Acta* 1981, 64 (1), 188-197).

Preparation of 3-oxobut-1-en-2-yl 4-nitrobenzoate of the formula (II-10)

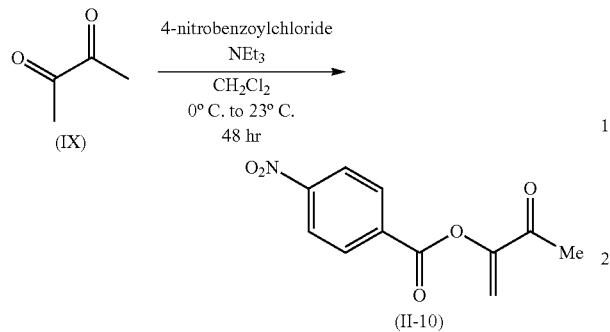

3-oxobut-1-en-2-yl 4-nitrobenzoate of the formula (II-10) was prepared from diacetyl (IX) (1.30 mL, 15.0 mmol, 1.0 equiv), triethylamine (2.5 mL, 18.0 mmol, 1.2 equiv), 4-nitrobenzoyl chloride (2.78 g, 15.0 mmol, 1.0 equiv), and dry dichloromethane (20 mL) following General Procedure A. The resulting solution was concentrated under reduced pressure, and the residue was subjected to silica gel chromatography (1:2 EtOAc/hexanes) to afford 3-oxobut-1-en-2-yl 4-nitrobenzoate of the formula (II-10) (2.16 g, 9.2 mmol, 61%) as a white solid.

$^1$H NMR (500 MHz, CDCl$_3$) δ 8.35-8.32 (m, 2H), 8.31-8.27 (m, 2H), 6.10 (d, J=2.7 Hz, 1H), 5.85 (d, J=2.8 Hz, 1H), 2.45 (s, 3H).

Preparation of the chiral ligand of formula (IV)

Preparation of ((4S,4'S,5S,5'S)-pyridine-2,6-diylbis (4,5-diphenyl-4,5-dihydro-1H-imidazole-2,1-diyl)) bis(naphthalen-1-ylmethanone) of the formula (IV-9)

The chiral ligand of the formula (IV-9) was prepared following the procedures of Bhor and coworkers (cf. Bhor, S. et al., Org. Lett. 2005, 7 (16), 3393-3396) as illustrated in the Scheme below and described in more detail hereinafter.

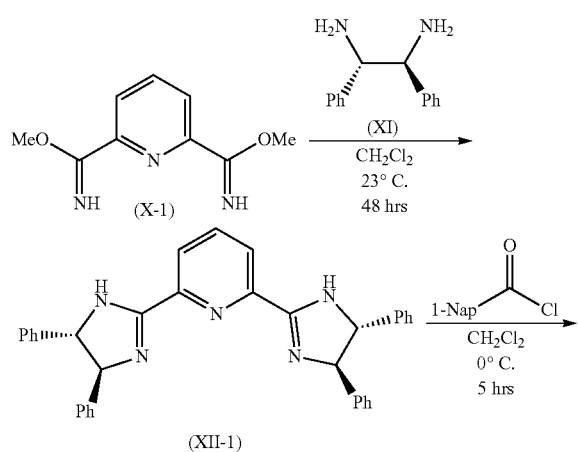

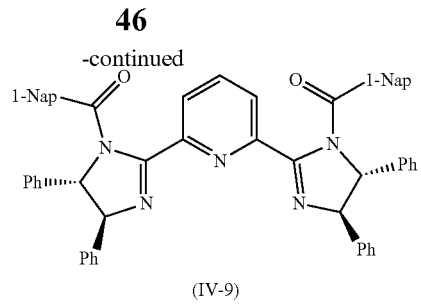

Procedure: A 50 ml pressure tube was charged with dimethyl pyridine-2,6-dicarboximidate of formula (X-1) (483 mg, 2.50 mmol, 1.0 equiv), (S,S)-1,2-diphenylethane-1,2-diamine of the formula (XI) (1.11 g, 5.25 mmol, 2.1 equiv) and dry dichloromethane (50 ml). After the resulting mixture was stirred at refluxing temperature for two days, water (20 ml) was added and the phases were separated. The aqueous phase was extracted with dichloromethane (20 ml×2). The combined organic layer was dried over MgSO$_4$ and the solvent was removed in vacuo to give a light yellow solid, which was purified by crystallization (ethylacetate) to give 2-[(4S,5S)4,5-diphenyl-4,5-dihydro-1H-imidazol-2-yl]-6-[(4R,5R)-4,5-diphenyl-4,5-dihydro-1H-imidazol-2-yl]pyridine of formula (XII-1) as a white solid (1.04 g, 2.00 mmol, 80%). Spectroscopic data matched previously reported values (cf. Bhor, S. et al., Org. Lett. 2005, 7 (16), 3393-3396).

To an oven-dried 250 mL round bottom flask, equipped with a stir bar, was charged 2-[(4S,5S)4,5-diphenyl-4,5-dihydro-1H-imidazol-2-yl]-6-[(4R,5R)-4,5-diphenyl-4,5-dihydro-1H-imidazol-2-yl]pyridine of formula (XII-1) (1.58 g, 3.04 mmol, 1.0 equiv), 4-dimethylaminopyridine (1.11 g, 9.12 mmol, 3.0 equiv), and dry dichloromethane (63.1 mL). The resulting mixture was cooled to 0° C., and 1-naphthoyl chloride (1.01 mL, 6.69 mmol, 2.20 equiv) added neat via syringe. The ice bath was then removed and the reaction mixture was stirred at room temp for 5 hours. The solvent was removed in vacuo, the residue was partitioned between saturated NH$_4$Cl (50 ml) and ethyl acetate (50 ml), and the aqueous phase was re-extracted with ethyl acetate (50 ml×2). The combined organic layer was dried (over MgSO$_4$), and the solvent was removed in vacuo. The residue was crystallized (ethyl acetate/hexane) to give ((4S,4'S,5S,5'S)-pyridine-2,6-diylbis(4,5-diphenyl-4,5-dihydro-1H-imidazole-2,1-diyl))bis(naphthalen-1-ylmethanone) of the formula (IV-9) as a white solid (2.46 g, 2.97 mmol, 98%). Spectroscopic data matched previously reported values (cf. Bhor, S. et al., Org. Lett. 2005, 7 (16), 3393-3396).

Preparation of ((4S,4'S,5S,5'S)-(4-chloropyridine-2, 6-diyl)bis(4,5-diphenyl-4,5-dihydro-1H-imidazole-2, 1-diyl))bis(naphthalen-1-ylmethanone) of the formula (IV-12)

The synthesis of the chiral ligand of the formula (IV-12) was adapted from the procedures of Bhor and coworkers (cf. Bhor, S. et al., Org. Lett. 2005, 7 (16), 3393-3396) as illustrated in the Scheme below and described in more detail hereinafter.

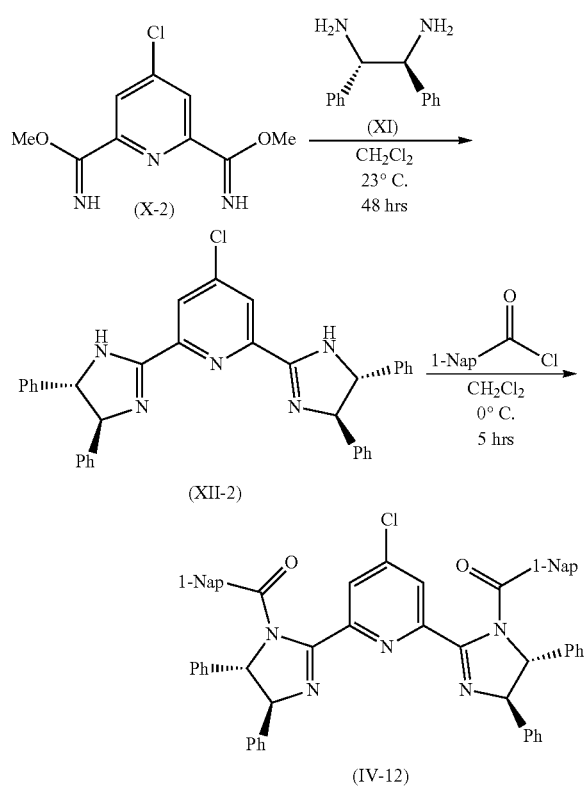

Procedure: A 15 ml pressure tube was charged with dimethyl 4-chloropyridine-2,6-dicarboximidate of formula (X-2) (150 mg, 0.659 mmol, 1.0 equiv), (S,S)-1,2-diphenylethane-1,2-diamine of the formula (XI) (294 mg, 1.38 mmol, 2.1 equiv) and dry dichloromethane (4 ml). After the resulting mixture was stirred at refluxing temperature for two days, water (20 ml) was added and the phases were separated. The aqueous phase was extracted with dichloromethane (20 ml×2). The combined organic layer was dried over MgSO$_4$ and the solvent was removed in vacuo to give a light yellow solid, which was used directly in the next step without further purification. To an oven-dried 25 mL round bottom flask, equipped with a stir bar, was charged 4-chloro-2-[(4S,5S)-4,5-diphenyl-4,5-dihydro-1H-imidazol-2-yl]-6-[(4R,5R)-4,5-diphenyl-4,5-dihydro-1H-imidazol-2-yl]pyridine of formula (XII-2) (111 mg, 0.2 mmol, 1.0 equiv), 4-dimethylaminopyridine (73.3 mg, 0.6 mmol, 3.0 equiv), and dry dichloromethane (8 mL). The resulting mixture was cooled to 0° C., and 1-naphthoyl chloride (66.3 µL, 0.44 mmol, 2.20 equiv) added neat via microsyringe. The ice bath was then removed and the reaction mixture was stirred at room temp for 5 hours. The solvent was removed in vacuo, the residue was partitioned between saturated NH$_4$Cl (50 ml) and ethyl acetate (50 ml), and the aqueous phase was re-extracted with ethyl acetate (50 ml×2). The combined organic layer was dried (over MgSO$_4$), and the solvent was removed in vacuo. The residue was crystallized (ethyl acetate/hexane) to give ((4S,4'S,5S,5'S)-(4-chloropyridine-2,6-diyl)bis(4,5-diphenyl-4,5-dihydro-1H-imidazole-2,1-diyl))bis(naphthalen-1-ylmethanone) of the formula (IV-12) as a white solid (128 mg, 0.149 mmol, 74%).

$^1$H NMR (300 MHz, CDCl$_3$) δ 7.84-6.92 (m, 36H), 5.49 (bs, 2H), 5.20 (bs, 2H).

Example 1: Preparation of 1-acetyl-4-methylcyclohex-3-en-1-yl benzoate of the formula (I-1) and 1-acetyl-4-methylcyclohex-3-en-1-yl 2,2-diphenylacetate of the formula (I-2) with a catalyst comprising Yb$^{3+}$ or Y$^{3+}$ and 2,6-Bis[(4S)-4-phenyl-2-oxazolinyl]pyridine of the formula (IV-1) or 2,6-Bis ((S)-4,5-dihydro-4-phenethyloxazol-2-yl)pyridine of the formula (IV-10) as chiral ligand Example 1.1: Preparation of 3-oxobut-1-en-2-yl benzoate of the Formula (II-1)

To a solution of diacetyl (2.19 mL, 25.0 mmol, 1.0 equiv.) and triethylamine (4.18 mL, 30.0 mmol, 1.2 equiv.) in dry dichloromethane (35 mL) was added benzoyl chloride at 0° C. under N$_2$. The reaction was allowed to slowly warm to 23° C. After 14 h, hexanes (35 mL) was added, and the reaction mixture was filtered through a plug of sand. The resulting solution was concentrated under reduced pressure, and the residue was subjected to silica gel chromatography (1:20 EtOAc:hexanes→1:10 EtOAc:hexanes) to afford 3-oxobut-1-en-2-yl benzoate of the formula (II-1) (2.21 g, 11.6 mmol, 46%) as a yellow oil which solidifies upon storage at −20° C. Spectroscopic data matched previously reported values (cf. Tamariz, J.; Vogel, P. Helv. Chim. Acta 1981, 64 (1), 188-197).

Example 1.2: Preparation of 3-oxobut-1-en-2-yl 2,2-diphenylacetate of the formula (II-2)

To a solution of diacetyl (1.32 mL, 15.0 mmol, 1.0 equiv.) and triethylamine (2.51 mL, 18.0 mmol, 1.2 equiv.) in dry dichloromethane (20 mL) was added technical grade diphenylacetyl chloride (3.46 g, 15.0 mmol, 1.0 equiv.) at 23° C. under N$_2$. After 24 h, hexanes (20 mL) was added, and the reaction mixture was filtered through a plug of sand, eluting with 1:1 dichloromethane:hexanes. The resulting solution was concentrated under reduced pressure, and the residue was subjected to silica gel chromatography (1:20 EtOAc:hexanes→1:10 EtOAc:hexanes→1:5 EtOAc:hexanes) to afford 3-oxobut-1-en-2-yl 2,2-diphenylacetate of the formula (II2) (3.55 g, 12.7 mmol, 85%) as a pale yellow solid. $^1$H NMR (300 MHz, CDCl$_3$): δ=7.33 (m, 10H), 5.92 (d, J=2.5 Hz, 1H), 5.58 (d, J=2.5 Hz, 1H), 5.22 (s, 1H), 5.28 (s, 3H).

Examples 1.3 to 1.7: Preparation of 1-acetyl-4-methylcyclohex-3-en-1-yl benzoate of the formula (I-1) and 1-acetyl-4-methylcyclohex-3-en-1-yl 2,2-diphenylacetate of the formula (I-2) by using varying of amounts of 2-methyl-1,3-butadiene of the formula (III-1) (hereinafter referred to as "isoprene"), Yb$^{3+}$ or Y$^{3+}$ as metal cation and 2,6-Bis [(4S)-4-phenyl-2-oxazolinyl]pyridine of the formula (IV-1) or 2,6-Bis((S)-4,5-dihydro-4-phenethyloxazol-2-yl)pyridine of the formula (IV-10) as chiral ligand 1-acetyl-4-methylcyclohex-3-en-1-yl benzoate of the formula (I-1) and 1-acetyl-4-methylcyclohex-3-en-1-yl 2,2-diphenylacetate of the formula (I-2) were prepared as shown in Scheme 1 below and described in more detail in the general procedure below.

Scheme 1

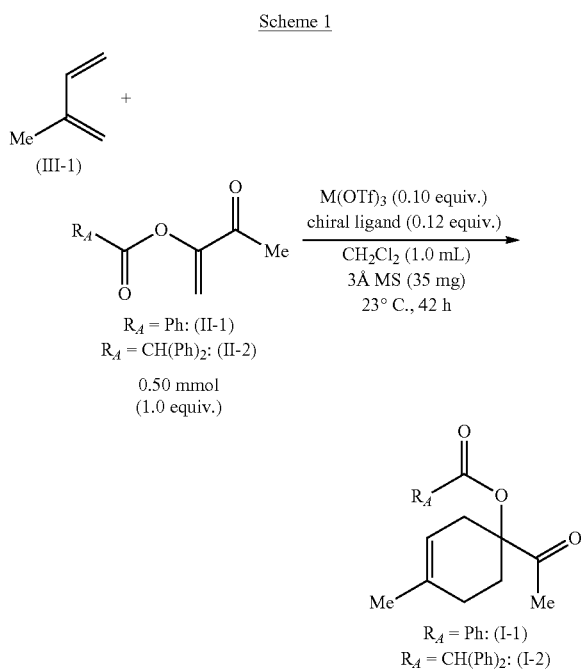

General procedure for examples 1.3 to 1.7: Yttrium (III) triflate or ytterbium (III) triflate (0.05 mmol, 0.10 equiv.) was added to an oven-dried 1-dram vial in an $N_2$-filled glovebox and capped with a Teflon-lined cap. The reaction vessel was then removed from the glovebox, and a stirbar, activated 3 Å molecular sieves (35 mg), and a solution of ligand in the organic solvent, i.e. dry dichloromethane (1.0 mL, 0.06 M), subsequently added. The mixture was stirred at 23° C. for 3 h, and then the diene, i.e. isoprene of the formula (III-1) (2.5 mmol or 5.0 mmol, 5.0 equiv. or 10.0 equiv.) was added, followed by the respective dienophile, i.e. 3-oxobut-1-en-2-yl benzoate of the formula (II-1) or 3-oxobut-1-en-2-yl 2,2-diphenylacetate of the formula (II-2) (0.50 mmol, 1.0 equiv.). The reaction mixture was then capped and sealed with electrical tape. After stirring at 23° C. for 42 h, the reaction mixture was filtered through a plug of silica gel, eluting with dichloromethane. The resulting solution was then concentrated, and dimethyl sulfone was added to the residue as an internal standard for $^1$H NMR. The entire residue was taken up in $CDCl_3$ and conversion/yield were determined by $^1$H NMR spectroscopy. 1-acetyl-4-methylcyclohex-3-en-1-yl benzoate of the formula (I-1): $^1$H NMR (300 MHz, $CDCl_3$): δ=8.02 (m, 2H), 7.58 (m, 1H), 7.46 (m, 2H), 5.34 (br s, 1H), 2.65 (m, 1H), 2.40 (m, 2H), 2.19 (s, 3H), 2.01 (m, 2H), 1.71 (s, 3H).

1-acetyl-4-methylcyclohex-3-en-1-yl 2,2-diphenylacetate of the formula (I-2): $^1$H NMR (300 MHz, $CDCl_3$): δ=7.32 (m, 10H), 5.23 (br s, 1H), 5.04 (s, 1H), 2.46 (m, 1H), 2.30 (m, 1H), 2.14 (m, 1H), 2.00 (s, 3H), 1.81 (m, 3H), 1.59 (br s, 3H).

The NMR sample was then loaded onto an EMD/Merck silica gel 60 F254 pre-coated plate (0.25 mm) and subjected to preparatory thin-layer chromatography, eluting with 1:5 EtOAc:hexanes. The isolated desired product was subjected to SFC analysis for determination of enantiomeric excess (ee).

SFC analysis was performed using a Mettler SFC supercritical $CO_2$ analytical chromatography system ($CO_2$=1450 psi, column temperature=40° C.) with Chiralcel AD-H or IC columns (4.6 mm×25 cm).

1-acetyl-4-methylcyclohex-3-en-1-yl benzoate of the formula (I-1): Chiralcel IC column, 2.5 mL/min, 7% iPrOH/$CO_2$, $t_{minor}$=11.3 min, $t_{major}$=12.3 min.

1-acetyl-4-methylcyclohex-3-en-1-yl 2,2-diphenylacetate of the formula (I-2): Chiralcel AD-H column, 2.5 mL/min, 7% iPrOH/$CO_2$, $t_{major}$=11.2 min, $t_{minor}$=13.3 min.

The results are summarized in the following Table I:

TABLE I

| Ex. | Amount isoprene of (equiv.) | Final product | $R_A$ | $M^{m+}$ | Chiral ligand | Conversion (%) | Yield (%) | ee (%) |
|---|---|---|---|---|---|---|---|---|
| 1.3 | 5.0 | (I-1) | Ph | $Yb^{3+}$ | (IV-1) | 30 | 29 | 67 |
| 1.4 | 5.0 | (I-1) | Ph | $Y^{3+}$ | (IV-1) | 23 | 23 | 70 |
| 1.5 | 5.0 | (I-1) | Ph | $Yb^{3+}$ | (IV-10) | 25 | 23 | 43 |
| 1.6 | 5.0 | (I-2) | $CH(Ph)_2$ | $Yb^{3+}$ | (IV-1) | 36 | 36 | 68 |
| 1.7 | 10.0 | (I-1) | Ph | $Yb^{3+}$ | (IV-1) | 48 | 46 | 68 |

Example 2: Preparation of 1-acetyl-4-methylcyclohex-3-en-1-yl benzoate of the formula (I-1) by using varying organic solvents 1-acetyl-4-methylcyclohex-3-en-1-yl benzoate of the formula (I-1) was prepared as shown in Scheme 2 below. The general procedure for Examples 1.3 to 1.7 was used, except that ytterbium (III) triflate was used in all cases, the temperature was 35° C. and varying organic solvents listed in Table II were used (i.e. dichloromethane and further organic solvents).

Scheme 2

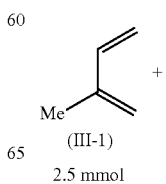

(III-1)
2.5 mmol

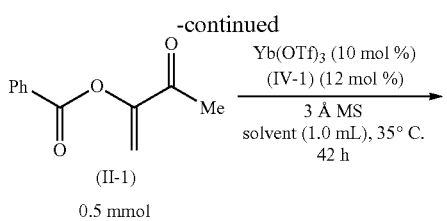

(II-1)
0.5 mmol

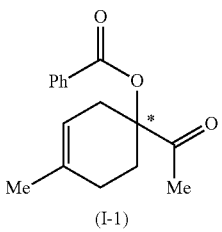

(I-1)

The results are summarized in the following Table II:

TABLE II

| Ex. | Organic solvent | Conversion (%) | ee (%) |
|---|---|---|---|
| 2.1 | dichloromethane | 65 | 63 |
| 2.2 | 1,2-dichloroethane | 50 | 50 |
| 2.3 | deuteriochloroform (CDCl$_3$) | 46 | 66 |
| 2.4 | tetrachloromethane | 22 | 27 |
| 2.5 | trichloroethylene | 33 | 40 |
| 2.6 | acetonitrile | — | −5 |
| 2.7 | toluene | — | 25 |
| 2.8 | tetrahydrofuran | — | 29 |
| 2.9 | Methyl-tert-butyl ether | 54 | 58 |
| 2.10 | Diethylether | 46 | 53 |
| 2.11 | 1,4-dioxane | 34 | 58 |
| 2.12 | 2,5-dimethyl tetrahydrofuran (mixture of cis and trans) | 29 | 49 |
| 2.13 | Cyclopentyl-methylether | 48 | 50 |
| 2.14 | diisopropylether | 10 | 35 |

Example 3: Preparation of 1-acetyl-4-methylcyclohex-3-en-1-yl benzoate of the Formula (I-1) by Using Varying Metal Salts 1-acetyl-4-methylcyclohex-3-en-1-yl benzoate of the formula (I-1) was prepared as shown in Scheme 3 below. The general procedure for Examples 1.3 to 1.7 was used, except that the temperature was 35° C. and varying metal salts listed in Table III were used (i.e. ytterbium (III) triflate and further metal salts).

Scheme 3

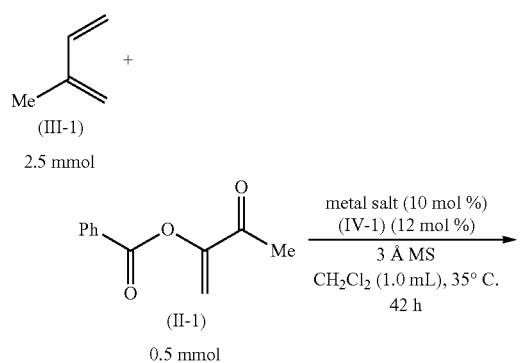

(I-1)

The results are summarized in the following Table III:

TABLE III

| Ex. | Metal salt | Conversion (%) | ee (%) |
|---|---|---|---|
| 3.1 | Sc(OTf)$_3$ | 17 | <2 |
| 3.2 | La(OTf)$_3$ | 9 | 11 |
| 3.3 | Ce(OTf)$_3$ | 18 | 19 |
| 3.4 | Pr(OTf)$_3$ | 29 | 43 |
| 3.5 | Nd(OTf)$_3$ | 22 | 39 |
| 3.6 | Sm(OTf)$_3$ | 35 | 46 |
| 3.7 | Eu(OTf)$_3$ | 24 | 36 |
| 3.8 | Gd(OTf)$_3$ | 40 | 58 |
| 3.9 | Tb(OTf)$_3$ | 49 | 62 |
| 3.10 | Dy(OTf)$_3$ | 35 | 41 |
| 3.11 | Ho(OTf)$_3$ | 39 | 56 |
| 3.12 | Er(OTf)$_3$ | 21 | 28 |
| 3.13 | Yb(OTf)$_3$ | 65 | 63 |
| 3.14 | Lu(OTf)$_3$ | 47 | 47 |

Example 4: Preparation of 1-acetyl-4-methylcyclohex-3-en-1-yl benzoate of the formula (I-1), 1-acetyl-4-methylcyclohex-3-en-1-yl 2,2-diphenylacetate of the formula (I-2) and 1-acetyl-4-methylcyclohex-3-en-1-yl adamantane-2-carboxylate of the formula (I-3) by using varying chiral ligands 1-acetyl-4-methylcyclohex-3-en-1-yl benzoate of the formula (I-1), 1-acetyl-4-methylcyclohex-3-en-1-yl 2,2-diphenylacetate of the formula (I-2) and 1-acetyl-4-methylcyclohex-3-en-1-yl adamantane-2-carboxylate of the formula (I-3) were prepared as shown in Scheme 4 below. The general procedure for Examples 1.3 to 1.7 was used, except that varying chiral ligands, namely 2,6-bis((S)-4-phenyl-4,5-dihydrooxazol-2-yl)pyridine of the formula (IV-1), 2,6-bis((S)-4-(4-bromophenyl)-4,5-dihydrooxazol-2-yl)pyridine of the formula (IV-2) and ((4S,4'S,5S,5'S)-pyridine2,6-diylbis(4,5-diphenyl-4,5-dihydro-1H-imidazole-2,1-diyl))bis(naphthalen-1-ylmethanone) of the formula (IV-9), were used as shown in Table IV below. Further, oxobut-1-en-2-yl adamantane-2-carboxylate of the formula (II-3) was used as an additional dienophile of formula (II).

Scheme 4

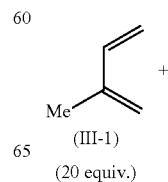

(III-1)
(20 equiv.)

-continued

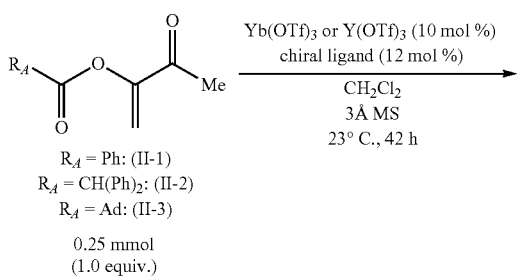

R_A = Ph: (II-1)
R_A = CH(Ph)_2: (II-2)
R_A = Ad: (II-3)

0.25 mmol
(1.0 equiv.)

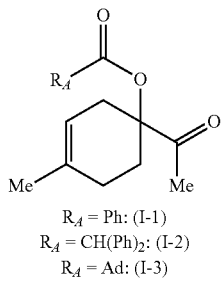

R_A = Ph: (I-1)
R_A = CH(Ph)_2: (I-2)
R_A = Ad: (I-3)

The results are summarized in the following Table IV:

TABLE IV

| Ex. | Chiral ligand | Metal salt | Dienophile (II) | Final compound (I) | Conversion (%) | ee (%) |
|---|---|---|---|---|---|---|
| 4.1 | (IV-1) | Yb(OTf)$_3$ | (II-2) | (I-2) | >98 | 74 |
| 4.2 | (IV-2) | Yb(OTf)$_3$ | (II-2) | (I-2) | 25 | 60 |
| 4.3 | (IV-9) | Yb(OTf)$_3$ | (II-2) | (I-2) | 83 | 77 |
| 4.4 | (IV-1) | Yb(OTf)$_3$ | (II-3) | (I-3) | 81 | 86 |
| 4.5 | (IV-9) | Y(OTf)$_3$ | (II-1) | (I-1) | >98 | 86 |

Example 5: Preparation of 1-acetyl-4-methylcyclohex-3-en-1-yl benzoate of the formula (I-1) by using varying temperatures 1-acetyl-4-methylcyclohex-3-en-1-yl benzoate of the formula (I-1) was prepared as shown in Scheme 5 below. The general procedure for Examples 1.3 to 1.7 was used, except that the temperature was varied, as shown in Table V below.

Scheme 5

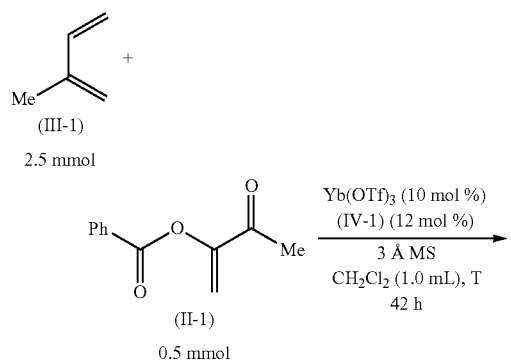

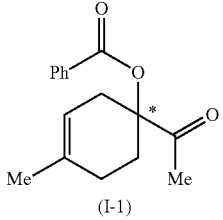
(I-1)

The results are summarized in the following Table V:

TABLE V

| Ex. | Temperature T (° C.) | Conversion (%) | ee (%) |
|---|---|---|---|
| 5.1 | 23 | 30 | 67 |
| 5.2 | 35 | 65 | 63 |

Example 6: Preparation of 1-acetyl-3,4-dimethylcyclohex-3-en-1-yl benzoate of the formula (I-6) and 1-acetyl-3,4-dimethylcyclohex-3-en-1-yl 2,2-diphenylacetate of the formula (I-7) by using 2,3-dimethyl-1,3-butadiene of the formula (III-2) as the diene 1-acetyl-3,4-dimethylcyclohex-3-en-1-yl benzoate of the formula (I-6) and 1-acetyl-3,4-dimethylcyclohex-3-en-1-yl 2,2-diphenylacetate of the formula (I-7) were prepared as shown in Scheme 6 below. The general procedure for Examples 1.3 to 1.7 was used, except that 2,3-dimethyl-1,3-butadiene of the formula (III-2) was used as the diene (see also Table VI below).

Scheme 6

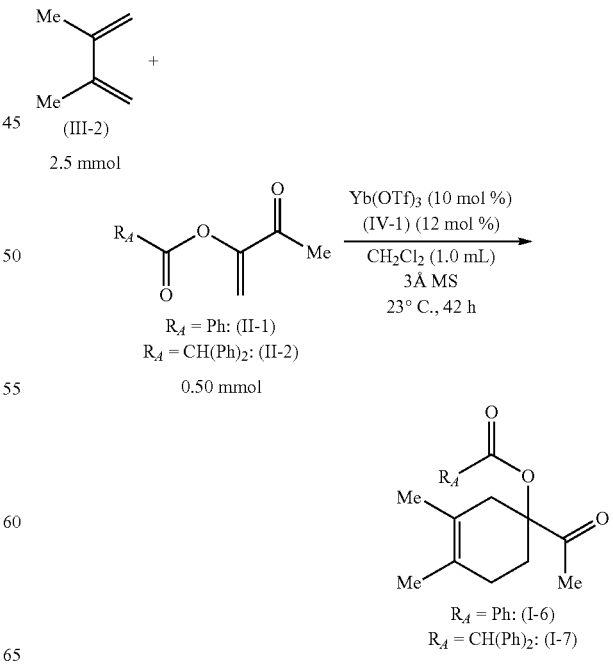

R_A = Ph: (I-6)
R_A = CH(Ph)_2: (I-7)

The results are summarized in the following Table VI:

TABLE VI

| Ex. | Dienophile (II) | Diene (III) | Final compound (I) | Conversion (%) | Ee (%) |
|---|---|---|---|---|---|
| 6.1 | (II-1) | (III-2) | (I-6) | 52 | 68 |
| 6.2 | (II-2) | (III-2) | (I-7) | 60 | 67 |

Example 7: Preparation of 2-acetylbicyclo[2.2.2]oct-5-en-2-yl benzoate of the formula (I-8), 2-acetylbicyclo[2.2.2]oct-5-en-2-yl 2,2-diphenylacetate of the formula (I-9) and 2-acetylbicyclo[2.2.2]oct-5-en-2-yl adamantane-2-carboxylate of the formula (I-10) by using 1,3-cyclohexadiene of the formula (III-3) as the diene 2-acetylbicyclo[2.2.2]oct-5-en-2-yl benzoate of the formula (I-8), 2-acetylbicyclo[2.2.2]oct-5-en2-yl 2,2-diphenylacetate of the formula (I-9) and 2-acetylbicyclo[2.2.2]oct-5-en-2-yl adamantane2-carboxylate of the formula (I-10) were prepared as shown in Scheme 7 below. The general procedure for Examples 1.3 to 1.7 was used, except that 1,3-cyclohexadiene of the formula (III3) was used as the diene. Further, oxobut-1-en-2-yl adamantane-2-carboxylate of the formula (II-3) was used as an additional dienophile of formula (II).

Scheme 7

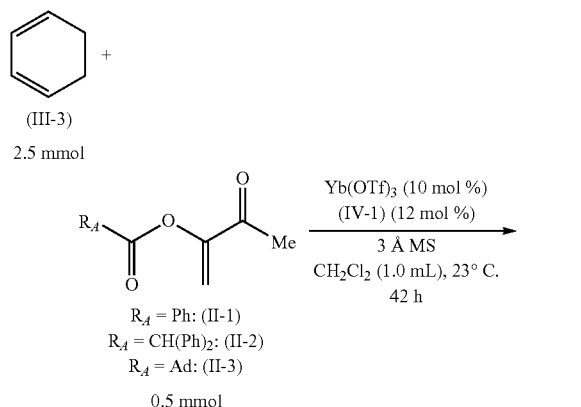

$R_A$ = Ph: (II-1)
$R_A$ = CH(Ph)$_2$: (II-2)
$R_A$ = Ad: (II-3)

0.5 mmol

Yb(OTf)$_3$ (10 mol %)
(IV-1) (12 mol %)
3 Å MS
CH$_2$Cl$_2$ (1.0 mL), 23° C.
42 h

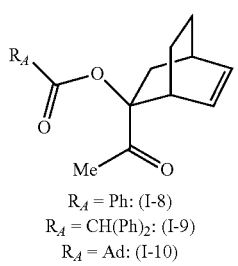

$R_A$ = Ph: (I-8)
$R_A$ = CH(Ph)$_2$: (I-9)
$R_A$ = Ad: (I-10)

The results are summarized as follows:

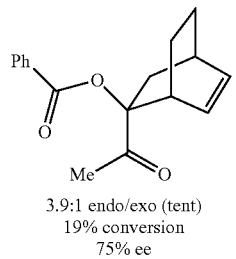

(I-8)

3.9:1 endo/exo (tent)
19% conversion
75% ee

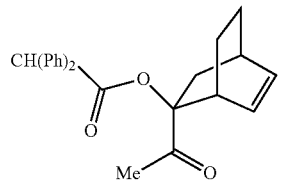

(I-9)

6:1 endo/exo (tent)
24% conversion
88% ee

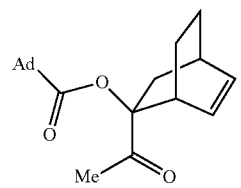

(I-10)

5.6:1 endo/exo (tent)
29% conversion
91% ee

Example 8: Preparation of 1-acetyl-4-methylcyclohex-3-en-1-yl benzoate of the formula (I-1) and 1-acetyl-4-methylcyclohex-3-en-1-yl 2,2-diphenylacetate of the formula (I-2)

General procedure for examples 8.1 to 8.8: metal salt (0.05 mmol, 0.10 equiv.) was added to an oven-dried 1-dram vial in an N$_2$-filled glovebox and capped with a Teflon-lined cap. The reaction vessel was then removed from the glovebox, and a stirbar, and a solution of the chiral ligand (IV) in the dry organic solvent (1.0 mL, 0.06 M), was subsequently added. The mixture was stirred at 23° C. for 3 h, and then the diene, i.e. isoprene of the formula (III-1) (2.5 mmol or 5.0 mmol, 5.0 equiv. or 10.0 equiv.) was added, followed by the respective dienophile, i.e. 3-oxobut-1-en-2-yl benzoate of the formula (II-1) or 3-oxobut-1-en-2-yl 2,2-diphenylacetate of the formula (II-2) (0.50 mmol, 1.0 equiv.). The reaction mixture was then capped and sealed with electrical tape. After stirring at 23° C. for 42 h, the reaction mixture was filtered through a plug of silica gel, eluting with dichloromethane. The resulting solution was then concentrated, and dimethyl sulfone was added to the residue as an internal standard for $^1$H NMR. The entire residue was taken up in CDCl$_3$ and conversion/yield were determined by $^1$H NMR spectroscopy. The NMR sample was then loaded onto an EMD/Merck silica gel 60 F254 pre-coated plate 10 (0.25 mm) and subjected to preparatory thin-layer chromatography, eluting with 1:5 EtOAc:hexanes. The isolated desired product was subjected to SFC analysis for determination of enantiomeric excess (ee). SFC analysis was performed using a Mettler SFC supercritical $CO_2$ analytical chromatography 15 system ($CO_2$=1450 psi, column temperature=40° C.) with Chiralcel AD-H or IC columns (4.6 mm×25 cm). 1-acetyl-4-methylcyclohex-3-en-1-yl benzoate of the formula (I-1): Chiralcel IC column, 2.5 mL/min, 7% iPrOH/$CO_2$, $t_{minor}$=11.3 min, $t_{major}$=12.3 min. 1-acetyl-4-methylcyclohex-3-en-1-yl 2,2-diphenylacetate of the formula (I-2): Chiralcel AD-H column, 2.5 mL/min, 7% iPrOH/$CO_2$, $t_{minor}$=11.2 min, $t_{major}$=13.3 min.

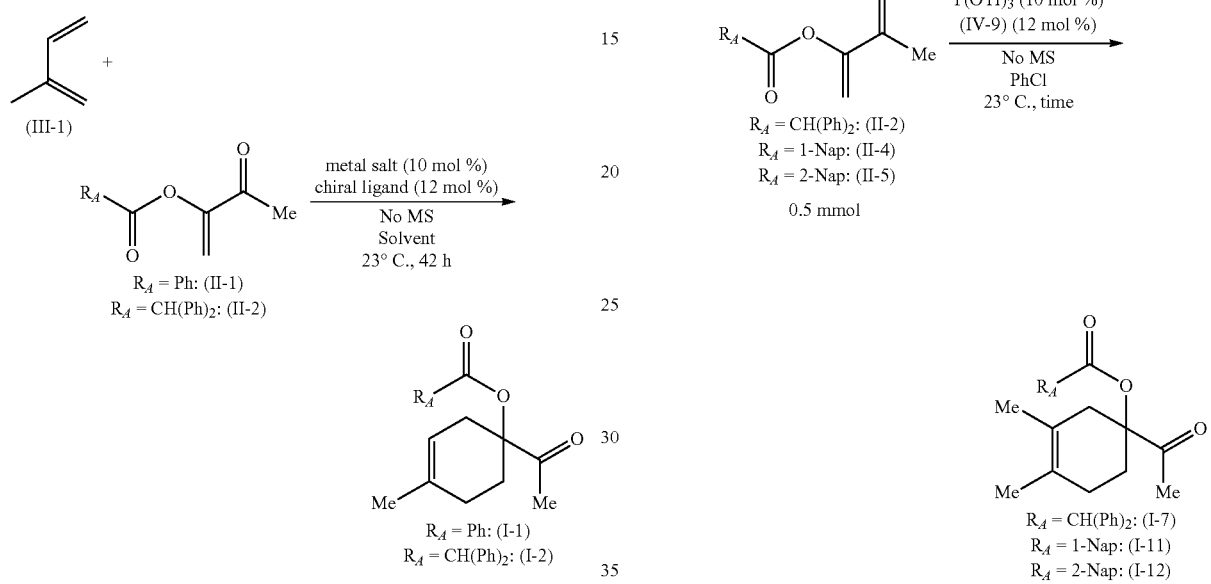

The results are summarized in the following Table VII:

TABLE VII

| Ex. | Metal salt | Dienophile (II) | Chiral ligand (IV) | Organic solvent | Solvent amount | Conversion (%) | Ee (%) |
|---|---|---|---|---|---|---|---|
| 8.1 | Y(OTf)$_3$ | (II-1) | IV-9 | DCM | 0.25 mL | 94 | 89 |
| 8.2 | Y(OTf)$_3$ | (II-1) | (IV-9) | PhCl | 0.25 mL | >98 | 91 |
| 8.3 | Sc(OTf)$_3$ | (II-1) | (IV-9) | DCM | 1 mL | 24 | 40 |
| 8.4 | Y(OTf)$_3$ | (II-1) | (IV-9) | DCM | 1 mL | 45 | 84 |
| 8.5 | Yb(OTf)$_3$ | (II-1) | (IV-9) | DCM | 1 mL | 18 | 65 |
| 8.6 | Y(OTf)$_3$ | (II-1) | (IV-1) | DCM | 1 mL | 37 | 67 |
| 8.7 | Yb(OTf)$_3$ | (II-1) | (IV-1) | DCM | 1 mL | 13 | 63 |
| 8.8 | Y(OTf)$_3$ | (II-2) | (IV-9) | PhCl | 0.25 mL | >98 | 86 |

Example 9: Preparation of 1-acetyl-3,4-dimethylcyclohex-3-en-1-yl 2,2-diphenylacetate of the formula (I-7), 1-acetyl-3,4-dimethylcyclohex-3-en-1-yl 1-napthoate of the formula (I-11), and 1-acetyl-3,4-dimethylcyclohex-3-en-1-yl 2-napthoate of the formula (I12) by using 2,3-dimethyl-1,3-butadiene of the formula (III-2) as the diene 1-acetyl-3,4-dimethylcyclohex-3-en-1-yl 2,2-diphenylacetate of the formula (I-7), 1-acetyl-3,4-dimethylcyclohex-3-en-1-yl 1-napthoate of the formula (I-11), and 1-acetyl-3,4-dimethylcyclohex-3-en-1-yl 2-napthoate of the formula (I-12) were prepared as shown in Scheme 9 below. The general procedure for Examples 8.1 to 8.8 was used, except that 2,3-dimethyl-1,3-butadiene of the formula (III-2) was used as the diene (see also Table VIII below).

The results are summarized in the following Table VIII:

TABLE VIII

| Ex. | Dienophile (II) | Diene equiv | Solvent amount | Conversion (%) | Ee (%) |
|---|---|---|---|---|---|
| 9.1 | (II-4) | 5.0 | 0.25 mL | 89 | 95 |
| 9.2 | (II-5) | 5.0 | 0.25 mL | 88 | 95 |
| 9.3 | (II-2) | 2 | 0.25 mL | >98 | 95.5 |
| 9.4 | (II-2) | 3 | 0.25 mL | >98 | 95.5 |
| 9.5 | (II-2) | 5 | 0.25 mL | >98 | 96 |
| 9.6 | (II-2) | 2 | 0.4 mL | >98 | 95.5 |
| 9.7 | (II-2) | 3 | 0.4 mL | >98 | 95.5 |
| 9.8 | (II-2) | 5 | 0.4 mL | >98 | 96 |
| 9.9 | (II-2) | 2 | 0.6 mL | >98 | 95.5 |
| 9.10 | (II-2) | 3 | 0.6 mL | >98 | 96 |
| 9.11 | (II-2) | 5 | 0.6 mL | >98 | 96 |

SFC analysis was performed using a Mettler SFC supercritical CO₂ analytical chromatography 15 system (CO₂=1450 psi, column temperature=40° C.) with Chiralcel AD-H or IC columns (4.6 mm×25 cm).

1-acetyl-3,4-dimethylcyclohex-3-en-1-yl 1-napthoate of the formula (I-11): Chiralcel IC column, 2.5 mL/min, 15% iPrOH/CO₂, $t_{minor}$=9.8 min, $t_{major}$=10.5 min. 1-acetyl-3,4-dimethylcyclohex-3-en-1-yl 2-napthoate of the formula (I-12): Chiralcel IC column, 2.5 mL/min, 15% iPrOH/CO₂, $t_{minor}$=10.4 min, $t_{major}$=12.0 min.

1-acetyl-3,4-dimethylcyclohex-3-en-1-yl 1-naphthoate (I-11):

$^1$H NMR (300 MHz, CDCl₃) δ 8.94-8.70 (m, 1H), 8.16 (dd, J=7.3, 1.3 Hz, 1H), 8.05 (dt, J=8.2, 1.1 Hz, 1H), 7.95-7.83 (m, 1H), 7.67-7.43 (m, 3H), 2.72 (d, J=17.9 Hz, 1H), 2.50-2.33 (m, 2H), 2.27 (d, J=0.4 Hz, 3H), 2.25-2.15 (m, 1H), 2.13-1.89 (m, 2H), 1.74-1.68 (m, 6H).

1-acetyl-3,4-dimethylcyclohex-3-en-1-yl 2-naphthoate (1-12):

$^1$H NMR (300 MHz, CDCl₃) δ 8.65-8.52 (m, 1H), 8.08-7.94 (m, 2H), 7.91-7.84 (m, 2H), 7.69-7.44 (m, 2H), 2.70 (d, J=17.9 Hz, 1H), 2.49-2.29 (m, 2H), 2.23 (s, 3H), 2.29-2.14 (m, 1H), 2.09-1.81 (m, 2H), 1.68 (s, 6H).

Example 10: Preparation of 1-acetyl-4-methylcyclohex-3-en-1-yl 2,2-diphenylacetate of the formula (I-2)

1-acetyl-4-methylcyclohex-3-en-1-yl 2,2-diphenylacetate of the formula (I-2) was prepared as shown in Scheme 10 below. The general procedure for Examples 8.1 to 8.8 was used except that, in certain examples, an additive was added following addition of the dienophile (see also Table IX below).

Scheme 10

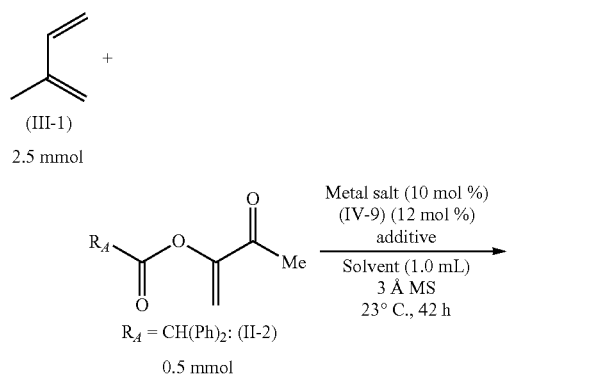

The results are summarized in the following Table IX:

TABLE IX

| Ex. | Metal salt | additive | Organic solvent | Conversion (%) | ee (%) |
|---|---|---|---|---|---|
| 10.1 | Y(OTf)₃ | — | PhCl | 93 | 87 |
| 10.2 | Y(OTf)₃ | — | DCM | 56 | 72 |
| 10.3 | YCl₃ | — | DCM | 6 | 11 |
| 10.4 | YCl₃ | NaB$_{Ar}$F (10 mol %) | DCM | 16 | 0 |
| 10.5 | YCl₃ | NaB$_{Ar}$F (30 mol %) | DCM | Nd | Nd |
| 10.6 | Y(OTf)₃ | N(n-Bu)₄Br (20 mol %) | DCM | >98 | 54 |
| 10.7 | Y(OTf)₃ | N(n-Bu)₄Br (10 mol %) | DCM | 91 | 65 |

Example 11: Preparation of 1-acetyl-4-methylcyclohex-3-en-1-yl 1-napthoate of the formula (I13) and 1-acetyl-4-methylcyclohex-3-en-1-yl 2-napthoate of the formula (I-14)

1-acetyl-4-methylcyclohex-3-en-1-yl 1-napthoate of the formula (I-13) and 1-acetyl-4-methylcyclohex-3-en-1-yl 2-napthoate of the formula (I-14) were prepared as shown in Scheme 11 below. The general procedure for Examples 8.1 to 8.8 was used, except that activated 3 Å molecular sieves (35 mg) were added before the ligand (see also Table X below).

Scheme 11

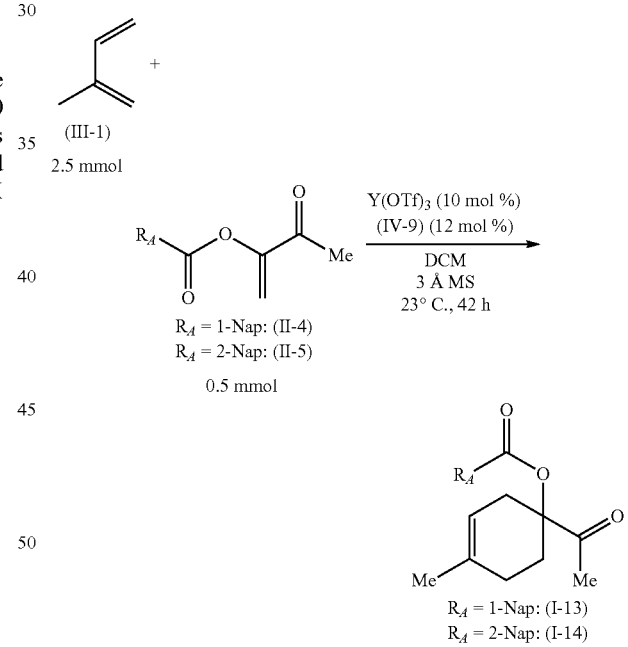

The results are summarized in the following Table X:

TABLE X

| Ex. | Dienophile (II) | Final product (I) | Conversion (%) | Ee (%) |
|---|---|---|---|---|
| 11.1 | (II-4) | (I-13) | >98 | 81 |
| 11.2 | (II-5) | (I-14) | >98 | 87 |

SFC analysis was performed using a Mettler SFC supercritical CO₂ analytical chromatography 15 system ($CO_2$=1450 psi, column temperature=40° C.) with Chiralcel AD-H or IC columns (4.6 mm×25 cm).

1-acetyl-4-methylcyclohex-3-en-1-yl 1-napthoate of the formula (I-13): Chiralcel IC column, 2.5 mL/min, 20% iPrOH/$CO_2$, $t_{minor}$=6.7 min, $t_{major}$=7.2 min. 1-acetyl-4-methylcyclohex-3-en-1-yl 2-napthoate of the formula (I-14): Chiralcel IC column, 3.0 mL/min, 15% iPrOH/$CO_2$.

Example 12: Preparation of 1-acetyl-4-methylcyclohex-3-en-1-yl pivalate of the formula (I-5), 1-acetyl-4-methylcyclohex-3-en-1-yl 2-bromobenzoate of the formula (I-15), 1-acetyl-4-methylcyclohex-3-en-1-yl 4-(tert-butyl)benzoate of the formula (I-16), 1-acetyl-4-methylcyclohex-3-en-1-yl 4-nitrobenzoate of the formula (I-17), 1-acetyl-4-methylcyclohex-3-en-1-yl 1-naphthoate of the formula (I-13) and 1-acetyl-4-methylcyclohex-3-en-1-yl 2-naphthoate of the formula (I-14)

1-acetyl-4-methylcyclohex-3-en-1-yl pivalate of the formula (I-5), 1-acetyl-4-methylcyclohex-3-en-1-yl 2-bromobenzoate of the formula (I-15), 1-acetyl-4-methylcyclohex-3-en-1-yl 4-(tert-butyl)benzoate of the formula (I-16), 1-acetyl-4-methylcyclohex-3-en-1-yl 4-nitrobenzoate of the formula (I-17), 1-acetyl-4-methylcyclohex-3-en-1-yl 1-naphthoate of the formula (I-13) and 1-acetyl-4-methylcyclohex-3-en-1-yl 2-naphthoate of the formula (I-14) were prepared as shown in Scheme 12 below. The general procedure for Examples 8.1 to 8.8 was used.

Scheme 12

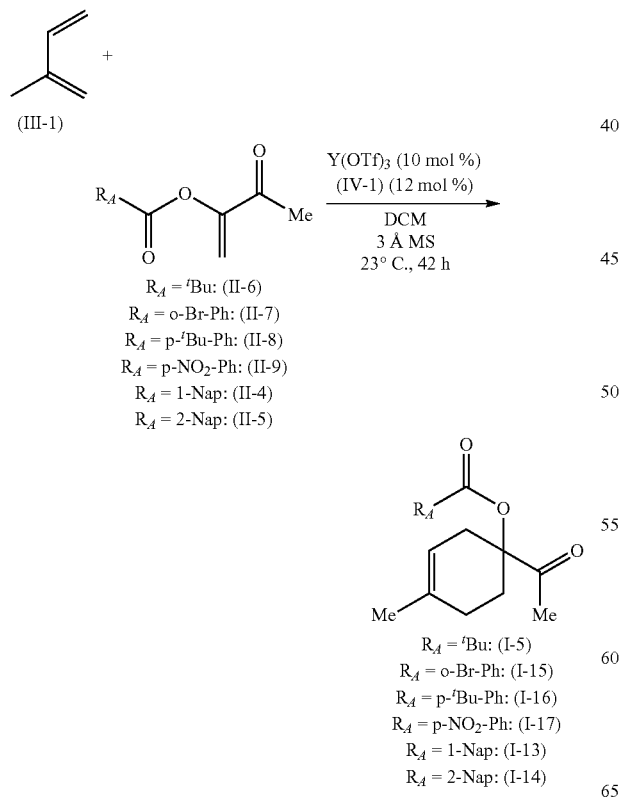

Results are as summarized below:

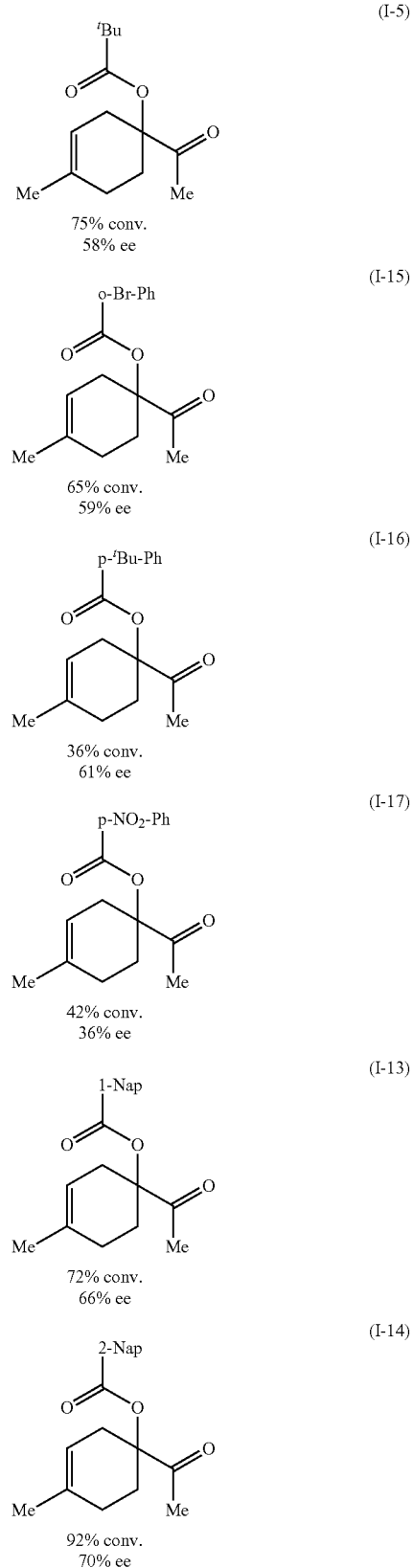

SFC analysis was performed using a Mettler SFC supercritical CO$_2$ analytical chromatography system (CO$_2$=1450 psi, column temperature=40° C.) with Chiralcel AD-H or IC columns (4.6 mm×25 cm).

1-acetyl-4-methylcyclohex-3-en-1-yl pivalate of the formula (I-5): Chiralcel AD-H column, 2.5 mL/min, 4% iPrOH/CO$_2$, t$_{minor}$=3.0 min, t$_{major}$=3.4 min, 1-acetyl-4-methylcyclohex-3-en-1-yl 2-bromobenzoate of the formula (I-15): Chiralcel IC column, 3.0 mL/min, 15% iPrOH/CO$_2$, 1-acetyl-4-methylcyclohex-3-en-1-yl 4-(tert-butyl)benzoate of the formula (I-16): Chiralcel IC column, 2.5 mL/min, 10% iPrOH/CO$_2$, t$_{minor}$=9.4 min, t$_{major}$=10.7 min, 1-acetyl-4-methylcyclohex-3-en1-yl 4-nitrobenzoate of the formula (I-17): Chiralcel IC column, 3.0 mL/min, 15% iPrOH/CO$_2$, t$_{minor}$=9.3 min, t$_{major}$=10.1 min.

1-acetyl-4-methylcyclohex-3-en-1-yl pivalate (1-5):
$^1$H NMR (500 MHz, CDCl$_3$) δ 5.47 (s, 1H), 2.51 (d, J=18.2 Hz, 1H), 2.40 (s, 1H), 2.28 (d, J=18.1 Hz, 1H), 2.24-2.16 (m, 1H), 2.13 (s, 3H), 2.04 (d, J=11.0 Hz, 1H), 2.01-1.90 (m, 1H), 1.68 (s, 3H), 1.21 (s, 9H).

1-acetyl-4-methylcyclohex-3-en-1-yl 2-bromobenzoate (1-15):
$^1$H NMR (500 MHz, CDCl$_3$) δ 7.80-7.72 (m, 1H), 7.72-7.63 (m, 1H), 7.42-7.30 (m, 2H), 5.35 (dp, J=4.7, 1.5 Hz, 1H), 2.73-2.63 (m, 1H), 2.48 (d, J=18.4 Hz, 1H), 2.44-2.35 (m, 1H), 2.26 (s, 3H), 2.23-2.14 (m, 1H), 2.07-1.93 (m, 2H), 1.74-1.69 (m, 3H).

1-acetyl-4-methylcyclohex-3-en-1-yl 4-(tert-butyl)benzoate (1-16):
$^1$H NMR (300 MHz, CDCl$_3$) δ 8.05 (s, 2H), 7.94 (d, J=8.1 Hz, 2H), 5.59 (d, J=1.5 Hz, 1H), 2.62 (d, J=18.4 Hz, 1H), 2.30 (t, J=16.0 Hz, 1H), 2.18 (s, 3H), 2.16-1.90 (m, 4H), 1.69 (s, 3H), 1.34 (dd, J=3.9, 1.5 Hz, 9H).

1-acetyl-4-methylcyclohex-3-en-1-yl 4-nitrobenzoate (1-17):
$^1$H NMR (500 MHz, CDCl$_3$) δ 8.31-8.26 (m, 2H), 8.21-8.15 (m, 2H), 5.47 (s, 1H), 2.67 (d, J=18.1 Hz, 1H), 2.50 (s, 1H), 2.43-2.36 (m, 1H), 2.22 (s, 3H), 2.16-1.92 (m, 3H), 1.71 (d, J=1.6 Hz, 3H).

1-acetyl-4-methylcyclohex-3-en-1-yl 1-naphthoate (1-13):
$^1$H NMR (500 MHz, CDCl$_3$) δ 8.85 (d, J=8.6 Hz, 1H), 8.17 (dd, J=7.3, 1.3 Hz, 1H), 8.05 (d, J=8.2 Hz, 1H), 7.90 (dt, J=8.0, 1.0 Hz, 1H), 7.57-7.46 (m, 3H), 5.42 (d, J=4.0 Hz, 1H), 2.70 (d, J=18.2 Hz, 1H), 2.55 (d, J=18.3 Hz, 1H), 2.43 (ddd, J=13.5, 5.3, 2.5 Hz, 1H), 2.27 (s, 3H), 2.21 (d, J=14.2 Hz, 1H), 2.12-1.95 (m, 2H), 1.76 (s, 3H).

1-acetyl-4-methylcyclohex-3-en-1-yl 2-naphthoate (1-14):
$^1$H NMR (500 MHz, CDCl$_3$) δ 8.61-8.55 (m, 1H), 8.02 (dd, J=8.6, 1.7 Hz, 1H), 8.00-7.95 (m, 1H), 7.94-7.86 (m, 2H), 7.59 (dddd, J=25.8, 8.1, 6.9, 1.3 Hz, 2H), 5.39 (tt, J=3.6, 1.6 Hz, 1H), 2.73-2.65 (m, 1H), 2.53 (d, J=17.9 Hz, 1H), 2.42 (ddt, J=10.4, 5.1, 2.6 Hz, 1H), 2.23 (s, 3H), 2.17 (s, 1H), 2.09-1.99 (m, 2H), 1.73 (t, J=1.7 Hz, 3H).

Example 13: Preparation of 1-acetyl-3,4-dimethylcyclohex-3-en-1-yl benzoate (1-1) and 1-ace-tyl-3,4-dimethylcyclohex-3-en-1-yl 2,2-diphenylacetane of the formula (I-2)

1-acetyl-3,4-dimethylcyclohex-3-en-1-yl benzoate (1-1) and 1-acetyl-3,4-dimethylcyclohex-3-en1-yl 2,2-diphenylacetane of the formula (I-2) were prepared as shown in Scheme 13 below. The general procedure for Examples 8.1 to 8.8 was used except that the amount of diene was varied (see Table XI below).

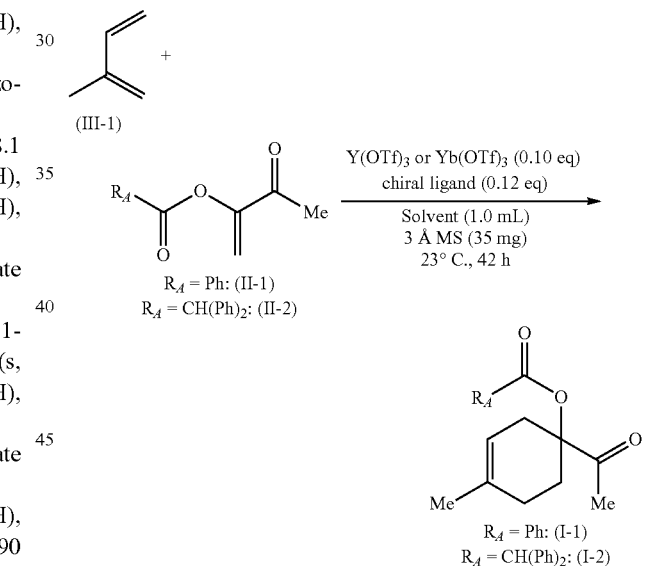

Scheme 13

TABLE XI

| Ex. | Dienophile (II) | Diene equiv | Metal salt | Chiral ligand | organic solvent | Conversion (%) | ee (%) |
|---|---|---|---|---|---|---|---|
| 13.1 | (II-2) (0.25 mmol) | 20 | Yb(OTf)$_3$ | (IV-8) | DCM | 79 | 65 |
| 13.2 | (II-1) (0.25 mmol) | 5 | Y(OTf)$_3$ | (IV-12) | PhCl | 38 | 65 |
| 13.3 | (II-1) (0.5 mmol) | 5 | Yb(OTf)$_3$ | (IV-13) | DCM | 29 | 26 |
| 13.4 | (II-1) (0.5 mmol) | 5 | Yb(OTf)$_3$ | (IV-14) | DCM | 38 | 12 |
| 13.5 | (II-1) (0.5 mmol) | 5 | Yb(OTf)$_3$ | (IV-10) | DCM | 25 | 30 |
| 13.6 | (II-1) (0.2 mmol) | 5 | Y(OTf)$_3$ | (IV-15) | DCM | 16 | 38 |

The invention claimed is:

1. A process for the synthesis of a non-racemic cyclohexene compound of formula (I)

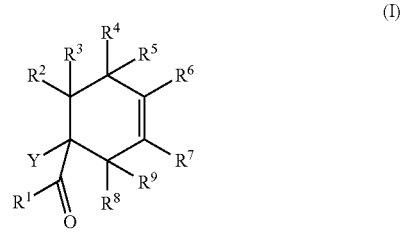

(I)

wherein
R$^1$ is selected from C$_1$-C$_8$-alkyl, C$_3$-C$_{12}$-cycloalkyl, unsubstituted or substituted C$_6$-C$_{20}$-aryl and unsubstituted or substituted C$_3$-C$_{20}$-heteroaryl,
R$^2$, R$^3$, R$^4$, R$^5$, R$^6$, R$^7$, R$^8$ and R$^9$ are each independently selected from hydrogen, C$_1$-C$_8$-alkyl, C$_3$-C$_6$-cycloalkyl, unsubstituted or substituted C$_6$-C$_{20}$-aryl and unsubstituted or substituted C$_3$-C$_{20}$-heteroaryl, or R$^5$ and R$^8$ together form a bridging moiety selected from —O—, —OH$_2$—, and —CH$_2$—CH$_2$— between the carbon atoms to which they are connected;
Y is OC(O)R$_A$ wherein R$_A$ is selected from C$_1$-C$_8$-alkyl, C$_3$-C$_{12}$-cycloalkyl, unsubstituted or substituted C$_6$-C$_{20}$-aryl, C$_6$-C$_{20}$-aryl-C$_1$-C$_4$-alkyl, di(C$_6$-C$_{20}$-aryl)-C$_1$-C$_4$-alkyl, unsubstituted or substituted C$_3$-C$_{20}$-heteroaryl, C$_1$-C$_8$-alkoxy, C$_3$-C$_6$-cycloalkyloxy, C$_6$-C$_{20}$-aryloxy, and NR$_B$R$_{B'}$, where R$_B$ and R$_{B'}$ are independently selected from hydrogen, C$_1$-C$_8$-alkyl, and C$_3$-C$_{12}$-cycloalkyl;
which process comprises reacting a compound of formula (II)

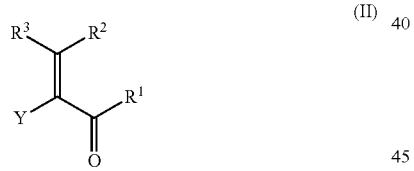

(II)

wherein R$^1$, R$^2$, R$^3$ and Y have the same meaning as in formula (I) with a compound of formula III,

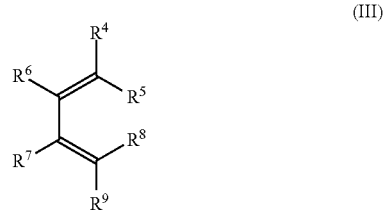

(III)

wherein R$^4$, R$^5$, R$^6$, R$^7$, R$^8$ and R$^9$ have the same meaning as in formula (I);
in the presence of a catalyst comprising at least one m-valent metal cation M$^{m+}$ wherein the metal M is selected from Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Gallium (Ga) and Indium (In), and m is an integer of 1, 2 or 3, and a chiral ligand of the formula (IV)

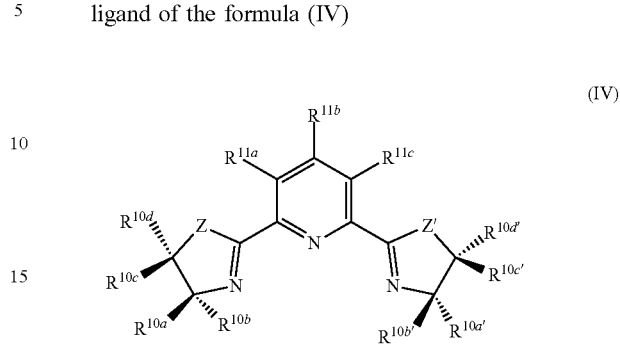

(IV)

wherein R$^{10a}$, R$^{10b}$, R$^{10c}$, R$^{10d}$, R$^{10a'}$, R$^{10b'}$, R$^{10c'}$ and R$^{10d'}$ are each independently selected from hydrogen, C$_1$-C$_8$-alkyl, C$_3$-C$_6$-cycloalkyl, unsubstituted or substituted C$_6$-C$_{20}$-aryl, C$_6$-C$_{20}$-aryl-C$_1$-C$_4$-alkyl and unsubstituted or substituted C$_3$-C$_{20}$-heteroaryl, or two or more of R$^{10a}$, R$^{10b}$, R$^{10c}$ and R$^{10d}$ and/or two or more of R$^{10a'}$, R$^{10b'}$, R$^{10c'}$ and R$^{10d'}$ together form an unsubstituted or substituted ring selected from C$_3$-C$_6$-cycloalkyl, C$_6$-C$_{20}$-aryl and C$_3$-C$_{20}$-heteroaryl;
provided that at least one of R$^{10a}$, R$^{10b}$, R$^{10c}$ and R$^{10d}$ and at least one of R$^{10a'}$, R$^{10b'}$, R$^{10c'}$ and R$^{10d'}$ are not hydrogen;
R$^{11a}$, R$^{11b}$ and R$^{11c}$ are each independently selected from hydrogen, halogen, cyano, C$_1$-C$_8$-alkyl, C$_1$-C$_4$-haloalkyl, C$_3$-C$_6$-cycloalkyl, unsubstituted or substituted C$_6$-C$_{20}$-aryl, unsubstituted or substituted C$_3$-C$_{20}$-heteroaryl, C$_1$-C$_5$-alkoxy, C$_3$-C$_6$-cycloalkyloxy, C$_6$-C$_2$O-aryloxy, C(O)—O—C$_1$-C$_6$-alkyl and O—C(O)—C$_1$-C$_6$-alkyl, and
Z and Z' are the same or different and selected from —O—, —O—CH$_2$—,

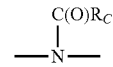

wherein R$_C$ is selected from C$_1$-C$_8$-alkyl, C$_3$-C$_8$-cycloalkyl, C$_1$-C$_8$-haloalkyl, and unsubstituted or substituted C$_6$-C$_{13}$ aryl.

2. The process according to claim 1 wherein, in the formulae (I) and (II), R$^1$ is C$_1$-C$_4$-alkyl and R$^2$ and R$^3$ are both hydrogen.

3. The process according to claim 1 wherein, in the formulae (I) and (II), R$^1$ is methyl and R$^2$ and R$^3$ are both hydrogen.

4. The process according to claim 1 wherein, in the formulae (I) and (III), R$^6$ is C$_1$-C$_4$-alkyl and R$^4$, R$^5$, R$^7$, R$^8$ and R$^9$ are each hydrogen.

5. The process according to claim 1 wherein, in the formulae (I) and (III), R$^6$ is methyl and R$^4$, R$^5$, R$^7$, R$^8$ and R$^9$ are each hydrogen.

6. The process according to claim 1 wherein, in the formulae (I) and (II), Y is OC(O)R$_A$ wherein R$_A$ is selected from C$_6$-C$_{20}$-aryl and di(C$_6$-C$_{20}$-aryl)-C$_1$-C$_4$-alkyl.

7. The process according to claim 1 wherein, in the formulae (I) and (II), Y is OC(O)R$_A$ wherein R$_A$ is selected from phenyl and diphenylmethyl.

8. The process according to claim 1 wherein the metal M is selected from Scandium (Sc), Yttrium (Y), Terbium (Tb) and Ytterbium (Yb).

9. The process according to claim 1 wherein the metal M is Yttrium (Y) or Ytterbium (Yb).

10. The process according to claim 1 wherein the metal M is Yttrium (Y).

11. The process according to claim 1 wherein the metal M is Ytterbium (Yb).

12. The process according to claim 1 wherein the catalyst additionally comprises at least one n-valent anion $A^{n-}$ wherein n is an integer of 1, 2 or 3.

13. The process according to claim 1 wherein the catalyst is obtained by reacting a metal salt of the formula $[M^{m+}]_n$ $[A^{n-}]_m$ (V) wherein $M^{m+}$ is a m-valent metal cation $M^{m+}$ wherein m is an integer of 1, 2 or 3 and the metal M has the same meaning as in claim 1, and $A^{n-}$ is a n-valent anion wherein n is an integer of 1, 2 or 3 with the chiral ligand of the formula (IV).

14. The process according to claim 12 wherein the n-valent anion $A^{n-}$ is independently selected from halide, tetrafluoroborate ($BF_4^-$), tetrakis[3,5-bis(trifluoromethyl)phenyl]borate ($[\{3,5-(CF_3)_2C_6H_3\}_4B]^-$), perchlorate ($ClO_4^-$), hexafluorophosphate ($PF_6^-$), antimony hexafluoride ($SbF_6^-$), nitrate ($NO_3^-$), a sulfonate anion of the formula $R^{12}SO_3^-$ wherein $R^{12}$ is selected from $C_1$-$C_4$-alkyl, $C_1$-$C_4$-haloalkyl and unsubstituted or substituted $C_6$-$C_{20}$-aryl, a carboxylate ion of the formula $R^{13}COO^-$ wherein $R^{13}$ is selected from hydrogen, $C_1$-$C_8$-alkyl, $C_3$-$C_{12}$-cycloalkyl, $C_1$-$C_8$-haloalkyl and unsubstituted or substituted $C_6$-$C_{20}$-aryl, sulfate ($SO_4^{2-}$), and a bis(sulfonyl)imide anion of the formula $(R^{14}SO_2)_2N^-$, wherein $R^{14}$ is selected from $C_1$-$C_4$-alkyl, $C_1$-$C_4$-haloalkyl and unsubstituted or substituted $C_6$-$C_{20}$-aryl.

15. The process according to claim 12 wherein the n-valent anion $A^{n-}$ is selected from halide and a sulfonate anion of the formula $R^{12}SO_3^-$ wherein $R^{12}$ is selected from $C_1$-$C_4$-alkyl and $C_1$-$C_4$-haloalkyl.

16. The process according to claim 12 wherein the n-valent anion $A^{n-}$ is triflate (trifluoromethanesulfonate).

17. The process according to claim 1 wherein, in the formula (IV), $R^{10a}$ and $R^{10a'}$ are independently selected from $C_1$-$C_8$-alkyl, $C_3$-$C_6$-cycloalkyl, unsubstituted or substituted $C_6$-$C_{20}$-aryl and unsubstituted or substituted $C_3$-$C_{20}$-heteroaryl, and $R^{10b}$, $R^{10c}$, $R^{10d}$, $R^{10b'}$, $R^{10c'}$ and $R^{10d'}$ are each hydrogen.

18. The process according to claim 1 wherein, in the formula (IV), $R^{10b}$ and $R^{10b'}$ are independently selected from $C_1$-$C_8$-alkyl, $C_3$-$C_6$-cycloalkyl, unsubstituted or substituted $C_6$-$C_{20}$-aryl and unsubstituted or substituted $C_3$-$C_{20}$-heteroaryl, and $R^{10a}$, $R^{10a'}$, $R^{10d}$, $R^{10a'}$, $R^{10c'}$ and $R^{10d'}$ are each hydrogen.

19. The process according to claim 1 wherein, in the formula (IV), Z and Z' are the same and selected

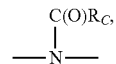

and $R^{10a}$, $R^{10b}$, $R^{10c}$, $R^{10d}$, $R^{10a'}$, $R^{10b'}$, $R^{10c'}$ and $R^{10d'}$ are each independently selected from hydrogen or unsubstituted or substituted $C_6$-$C_{20}$-aryl.

20. The process according to claim 1 wherein, in the formula (IV), Z and Z' are the same and selected from

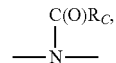

and $R^{10a}$, $R^{10b}$, $R^{10c}$, $R^{10d}$, $R^{10a'}$, $R^{10b'}$, $R^{10c'}$ and $R^{10d'}$ are each independently selected from hydrogen or phenyl.

21. The process according to claim 1 wherein, in the formula (IV), Z and Z' are the same and selected from

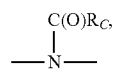

and $R_C$ is selected from unsubstituted or substituted $C_6$-$C_{13}$ aryl.

22. The process according to claim 1 wherein, in the formula (IV), $R^{11a}$, $R^{11b}$ and $R^{11c}$ are each hydrogen.

23. The process according to claim 1 wherein, in the formula (IV), $R^{11a}$ and $R^{11c}$ are both hydrogen, and $R^{11b}$ is halogen.

24. The process according to claim 1 wherein, in the formula (IV), $R^{11a}$ and $R^{11c}$ are both hydrogen, and $R^{11b}$ is chlorine.

25. The process according to claim 1 wherein, in the formula (IV), $R^{10a}$ and $R^{10a'}$ are both phenyl and $R^{10b}$, $R^{10c}$, $R^{10d}$, $R^{10b'}$, $R^{10c'}$, $R^{10d'}$, $R^{11a}$, $R^{11b}$ and $R^{11c}$ are each hydrogen.

26. The process according to claim 1 wherein the reaction is conducted in an organic solvent.

27. The process according to claim 26 wherein the organic solvent is selected from hydrocarbons, ethers, nitriles, esters, ketones and any combination thereof.

28. The process according to claim 26 wherein the organic solvent is selected from hydrocarbons.

29. The process according to claim 26 wherein the organic solvent is a hydrocarbon selected from aliphatic hydrocarbons, cycloaliphatic hydrocarbons, aromatic hydrocarbons, halogenated aliphatic hydrocarbons, halogenated aromatic hydrocarbons and any combination thereof.

30. The process according to claim 29 wherein the organic solvent is a hydrocarbon selected from aromatic hydrocarbons, halogenated aliphatic hydrocarbons, halogenated aromatic hydrocarbons and any combination thereof.

31. The process according to claim 29 wherein the organic solvent is a hydrocarbon selected from halogenated aliphatic hydrocarbons, halogenated aromatic hydrocarbons and any combination thereof.

32. The process according to claim 1 wherein the reaction is conducted at a temperature in the range from −20° C. to 50° C.

33. The process according to claim 1 wherein the non-racemic cyclohexene compound of formula (I) is further converted to a non-racemic cyclohexenol compound of formula (VI)

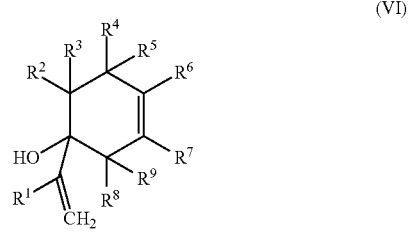

wherein $R^1$, $R^2$, $R^3$, $R^4$, $R^5$, $R^6$, $R^7$, $R^8$ and $R^9$ have the same meaning as in formula (I).

\* \* \* \* \*